(12) United States Patent
Rudey et al.

(10) Patent No.: US 12,103,914 B2
(45) Date of Patent: Oct. 1, 2024

(54) COMPOSITIONS OF BIOLOGICALLY ACTIVE MENAQUINOL DERIVATIVES AND METHODS OF TREATMENT

(71) Applicant: Epizon Pharma, Inc., New York, NY (US)

(72) Inventors: John M. Rudey, New York, NY (US); Eric Stephen Gruff, Poway, CA (US); Sam L. Nguyen, Dana Point, CA (US)

(73) Assignee: Epizon Pharma, Inc., New York, NY (US)

( * ) Notice: Subject to any disclaimer, the term of this patent is extended or adjusted under 35 U.S.C. 154(b) by 80 days.

(21) Appl. No.: 17/564,079

(22) Filed: Dec. 28, 2021

(65) Prior Publication Data

US 2022/0213021 A1    Jul. 7, 2022

Related U.S. Application Data

(60) Provisional application No. 63/132,045, filed on Dec. 30, 2020.

(51) Int. Cl.
*C07D 323/00* (2006.01)
*C07C 69/017* (2006.01)

(52) U.S. Cl.
CPC .......... *C07C 69/017* (2013.01); *C07D 323/00* (2013.01)

(58) Field of Classification Search
CPC ........................... C07D 320/00; C07C 69/017
See application file for complete search history.

(56) References Cited

U.S. PATENT DOCUMENTS

2007/0072940 A1 * 3/2007 Abraham ............... A61K 8/355
514/458

FOREIGN PATENT DOCUMENTS

EP    2060256 A1 *    5/2009 ............. A61K 31/05

OTHER PUBLICATIONS

Berge et al. J. Pharm. Sci. 1997, 66, pp. 1-19 (Year: 1997).*
Flowers et al. J. Am. Chem. Soc. 1993, 115, 9409-9416 (Year: 1993).*

* cited by examiner

*Primary Examiner* — Matthew P Coughlin

(57) ABSTRACT

The present application discloses, in part, isolated, stable and biologically active menaquinol derivatives and their methods of use for the treatment of various diseases.

6 Claims, 16 Drawing Sheets

In vivo plasma protein carbonyl formation. *$P < 0.05$ vs. normal volunteers ($N = 10$ in each group).

COMPOSITIONS OF BIOLOGICALLY ACTIVE MENAQUINOL DERIVATIVES AND METHODS OF TREATMENT

CROSS-REFERENCE TO RELATED APPLICATION

This application claims the benefit under 35 USC 119(e) of Provisional Patent Application No. 63/132,045 filed on Dec. 30, 2020, the entire content of which is incorporated into this application by reference.

FIELD OF INVENTION

The present invention relates to biologically active menaquinol derivatives, compositions and formulations, and combinations thereof, for the treatment of diseases associated with vitamin K, its reduced and bioactive form menaquinol and salts thereof, including osteoporosis and osteopenia.

BACKGROUND OF THE INVENTION

Vitamin K is known as a group of structurally similar, fat-soluble vitamins. Vitamin $K_2$ or menaquinone has nine related compounds that can be subdivided into the short-chain menaquinones (such as menaquinone-4 or MK-4) and the long-chain menaquinones, such as MK-7, MK-8 and MK-9 to MK-12. The vitamins include phylloquinone (K1), menaquinones (K2) and menadione (K3). Plants synthesize vitamin K1 while bacteria can produce a range of vitamin K2 forms, including the conversion of K1 to K2 by bacteria in the small intestines. Vitamin K3 is a synthetic version of the vitamin, and due to its toxicity, has been banned in by the US Food and Drug Administration for human uses.

It has been established that taking broad-spectrum antibiotics can reduce vitamin K production in the gut by nearly 74% in people compared to those not taking these antibiotics. Diets that are low in vitamin K also decrease the body's vitamin K concentration. Vitamin K1 is preferentially used by the liver as a clotting factor. Vitamin K2 is used preferentially in the brain, vasculature, breasts and kidneys. Vitamin K2 contributes to production of myelin and sphingolipids (fats essential for brain health) and protects against oxidative damage in the brain. Vitamin K2, such as MK-4, promotes bone health by stimulating connective tissue production in bone.

Vitamin K2, which is the main storage form in animals, has several subtypes, which differ in chain length of the isoprenoid group or residue in the side chains. These vitamin K2 homologues are called menaquinones, and are characterized by the number of isoprenoid residues in their side chains. For example, MK-4 has four isoprene residues in its side chain, and is the most common type of vitamin K2 in animal products. MK-4 is normally synthesized from vitamin $K_1$ in certain animal tissues (arterial walls, pancreas and testes) by replacement of the phytyl group with an unsaturated geranyl group containing four isoprene units. Unlike MK-4, MK-7 is not produced by human tissue. MK-7 may be converted from phylloquinone ($K_1$) in the colon by *E. coli* bacteria. MK-4 and MK-7 are sold in the U.S. in dietary supplements for bone health. MK-4 has been shown to decrease the incidence of fractures. MK-4, at a dose of 45 mg daily, has been approved by the Ministry of Health in Japan since 1995 for the prevention and treatment of osteoporosis.

Osteoporosis is a disease of bone that leads to an increased risk of fracture. In osteoporosis the bone mineral density (BMD) is reduced, bone micro architecture is disrupted, and the amount and variety of non-collagenous proteins in bone is altered. The World Health Organization define osteoporosis (in women) as a bone mineral density 2.5 standard deviations below peak bone mass, that is, for an average 30-year-old healthy female. Osteoporosis is most common in women after menopause (referred to as postmenopausal osteoporosis). Osteoporosis may also develop in men, and may occur in anyone in the presence of particular hormonal disorders and other chronic diseases or as a result of medications, specifically glucocorticoids, when the disease is called steroid- or glucocorticoid-induced osteoporosis and as a result of nutritional deficiency states or other metabolic disorders, for example, hyponatremia or as a secondary consequence of cancer. Osteopenia is a condition where bone mineral density is lower than normal, and is considered by many doctors to be a precursor to osteoporosis.

The underlying mechanism in most cases of osteoporosis is an imbalance between bone resorption and bone formation. The three main mechanisms by which osteoporosis develops include an inadequate peak bone mass (the skeleton develops insufficient mass and strength during growth), excessive bone resorption and inadequate formation of new bone during remodelling. Hormonal factors strongly determine the rate of bone resorption; lack of estrogen (e.g., as a result of menopause) increases bone resorption as well as decreasing the deposition of new bone that normally takes place in weight-bearing bones. In addition to estrogen, calcium metabolism plays a significant role in bone turn-over, and deficiency of calcium and vitamin D leads to impaired bone deposition; in addition, the parathyroid glands react to low calcium levels by secreting parathyroid hormone, which increases bone resorption to ensure sufficient calcium in the blood. Medications used for the treatment of osteoporosis includes calcium, vitamin D, vitamin K, bisphosphonates, Calcitonin, Teriparatide, strontium ranelate, hormone replacement and selective estrogen receptor modulators.

It has been established that cardiovascular disease (CVD) is the most frequent cause of death in patients with chronic kidney disease (CKD). When compared to the general population, the cause of death attributed to CVD is about 10-20 times higher in CKD patients when they are being treated with hemodialysis. In addition, it has been demonstrated that vascular calcification and the correlated arterial stiffness is prevalent in the incidence of CVD. In addition, patient with CKD undergoing dialysis treatment have a 3 times higher risk of bone fractures, such as vertebral fractures and other type of bone fractures.

Vitamin K, including MK-7, are present in low concentrations in a typical diet. It has also been established that there exists a direct correlation between the level of vitamin K in a patient's blood and the incidence of vascular calcification, bone density and bone strength. Accordingly, the supplemental use of vitamin K, such as MK-7 and its also fat-soluble hydroquinone (menaquinol) derivatives as disclosed herein, may provide significant clinical benefit for reducing vascular calcification noted, in part, by arterial stiffness, and increase bone mineralization or increase in bone mineral density, that will help treat or prevent CVD, and treat or prevent bone diseases in patients with CKD.

It has also been established that in food products, vitamin K1 is bound to the chloroplast membrane of leafy green vegetables. MK-4, which is derived from the conversion of menadione, a synthetic analog of vitamin K, is found in animal products such as eggs and meats. Long chain menaquinones such as MK-7, MK-8 and MK-9, are found in fermented foods such as cheese, curd and sauerkraut. It has also been established that the effects of long chain MK-n such as MK-7 on normal blood coagulation is greater and longer lasting than vitamin K1 and MK-4. MK-7 has also been shown to have a long half-life in serum when compared to MK-4, providing a better carboxylation-grade of osteocalcin compared to Vitamin K1. See Sato et al., *Nutrition Journal,* 2012, 11:93.

Nutritional doses of MK-7 can be established to be well absorbed in humans, and as a consequence, provide a significant increase in the serum for MK-7 levels. However, very little information is known of MK-7, and menaquinol-7, primarily because MK-7 and menaquinol-7, are not readily available nor commercially accessible via standard synthetic methods.

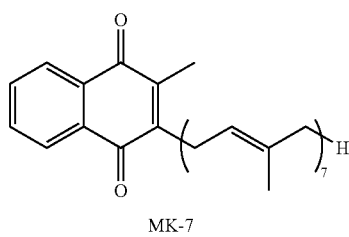

MK-7

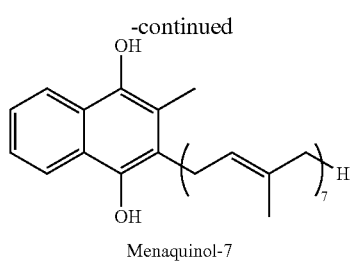

Menaquinol-7

In one embodiment, the present application discloses novel and biologically effective menaquinol derivatives, including salts, and their method of use for the treatment of various diseases.

The foregoing examples of the related art and limitations are intended to be illustrative and not exclusive. Other limitations of the related art will become apparent to those of skill in the art upon a reading of the specification and a study of the drawings or figures as provided herein.

SUMMARY OF THE INVENTION

The inventors recognize a continuing need for designing novel compounds and their formulations that are effective for these indications. The following embodiments, aspects and variations thereof are exemplary and illustrative are not intended to be limiting in scope.

In one embodiment, the present application discloses an isolated, stable and biologically active menaquinol derivative of the formula I, Ia to Ii, II, III, IV, V, VI, VII or VIII, or mixtures thereof;

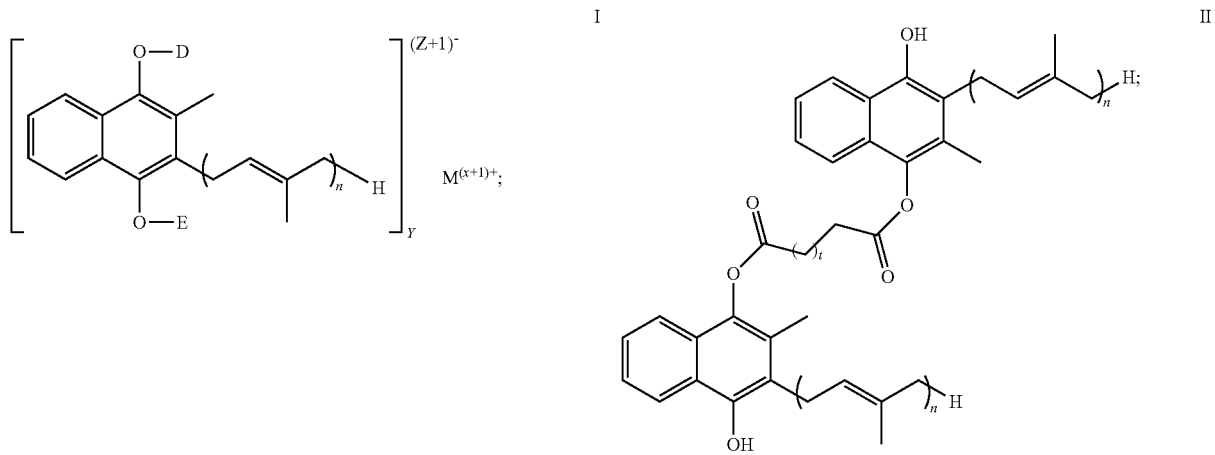

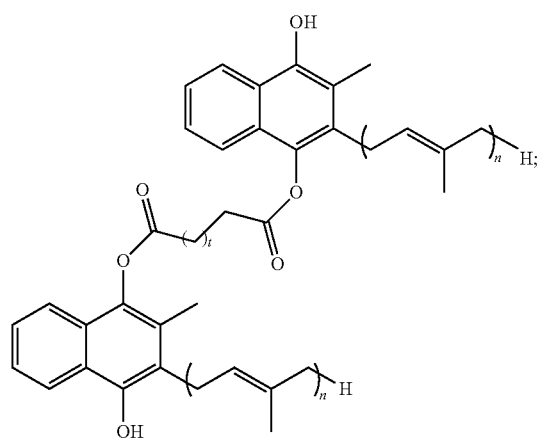
III
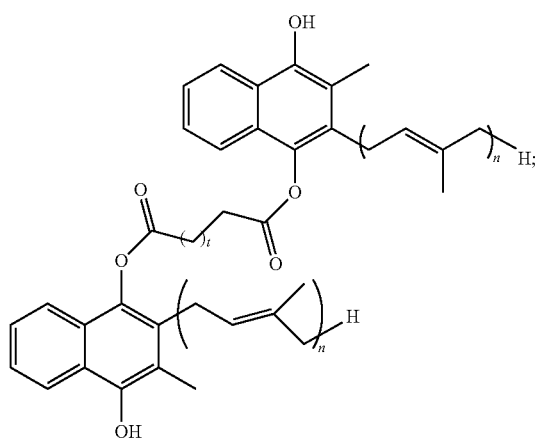
IV
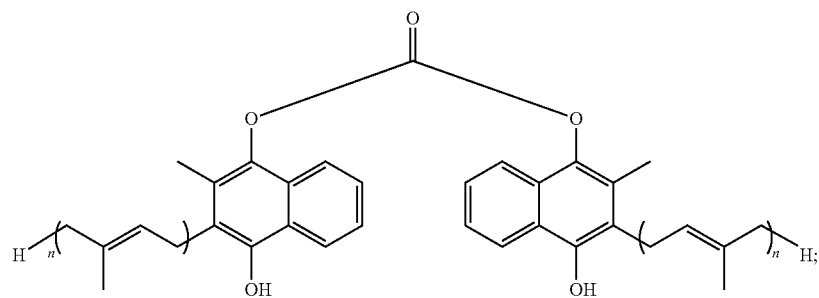
V
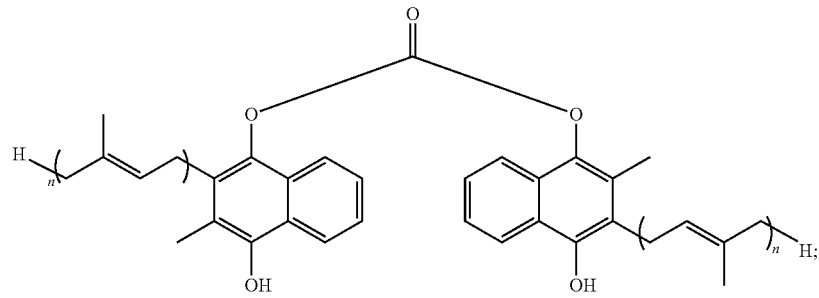
VI
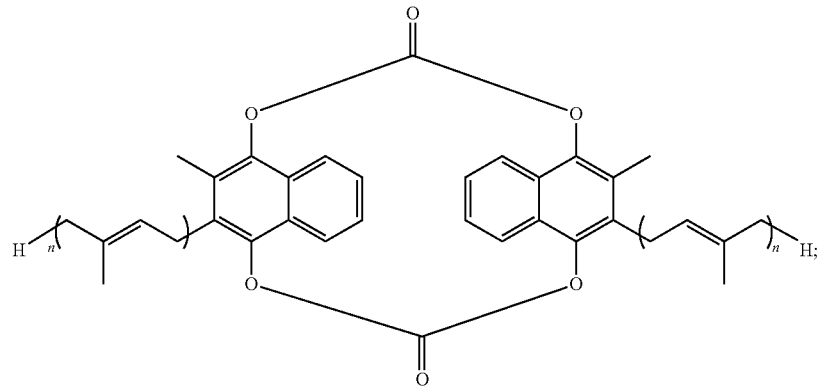
VII

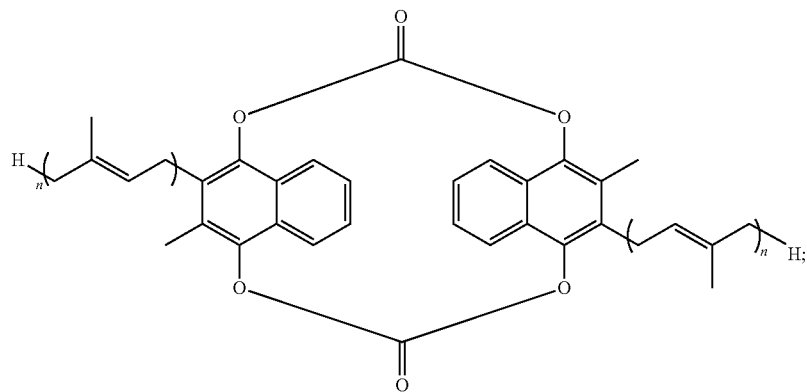

VIII wherein:

each D and E is independently − (a negative charge) or H;

M, where present, is a metal ion or an amine salt selected from the group consisting of $Li^+$, $Na^+$, $K^+$, $Mg^{2+}$, $Ca^{2+}$, $Al^{3+}$ and $Zn^{2+}$, and arginine, benzathine, chloroprocaine, choline, diethanolamine, ethanolamine, ethylenediamine, lysine, histidine, meglumine, procaine and triethylamine;

X is 0, 1 or 2; Y is 0.5, 1, 2 or 3; Z is 0 or 1; n is 7, 8, 9 or 10; and t is 0, 1, 2 or 3; and the hydrates thereof.

As representative examples, the salt may include the following compounds:

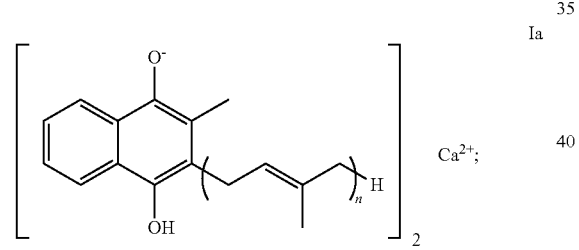

Ia

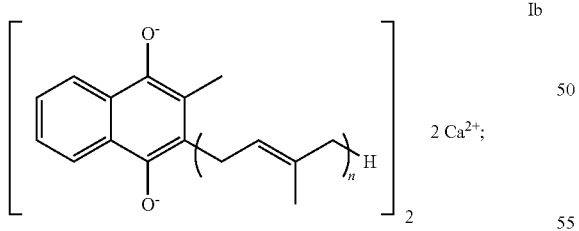

Ib

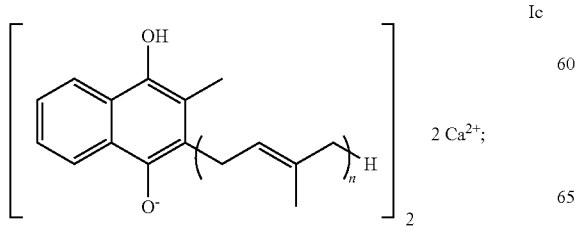

Ic

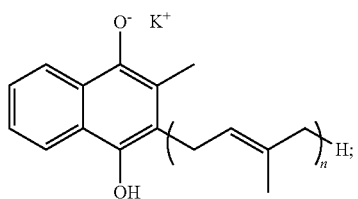

Id

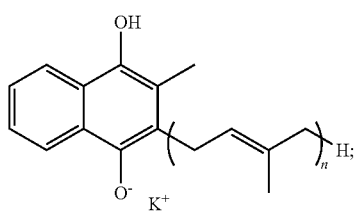

Ie

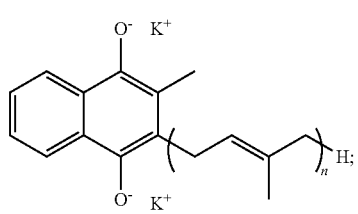

If

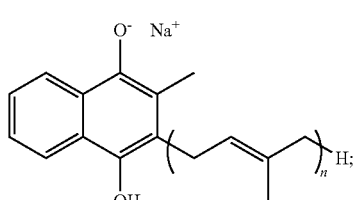

Ig

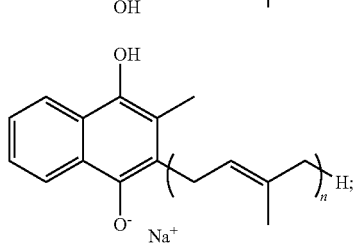

Ih

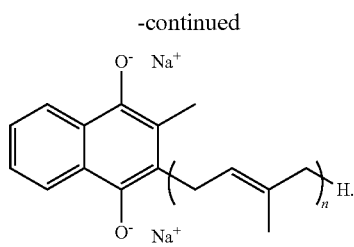

As shown in the salt of the formula I the number (Y) of the menaquinol ion in the salt is a function of the nature and charge of the metal counterion (M) as well as the number of the menaquinol molecules with the —OH group or the corresponding phenoxide group, —O⁻, which may be ionically bound to the metal counterion (or cation), M; as well as the method and reaction condition for preparing the salt. For example, where Y is 0.5, then there are stoichiometrically 2 metal ions M ionically bonded to the 2 phenoxide groups of a single menaquinol molecule. Similarly, where there is a stoichiometry equal to 2 equivalents or in excess of greater than 2 equivalents of the metal salt that is used to prepare the salt I, then both of the —OH groups would form the corresponding phenoxide ion (—O⁻) along with the metal salt, M, depending on the charge and valency of the metal. For example, when the salt is formed using a stoichiometric molar amount of NaOH, then the corresponding phenoxide salt may be a mono-phenoxide ionically bonded to one sodium ion. And when an excess or more than 2 mole equivalents of NaOH is employed, then the menaquinol product is a "di-phenoxide" with two sodium counterions ionically bonded to the two phenoxide ions. Similarly, when a half molar equivalent of $Ca(OH)_2$ salt is employed, depending on the reaction method and conditions, the di-valent calcium ion ($Ca^{2+}$) may be ionically bonded to two different menaquinol molecules via their phenoxide groups. In one variation of the above, M is a metal selected from the group consisting of $Li^+$, $Na^+$, $K^+$, $Mg^{2+}$, $Ca^{2+}$, $Al^{3+}$ and $Zn^{2+}$. In one variation, M is $Ca^{+2}$.

In one variation, the menaquinol compounds of the formulae II to VI may be covalently bonded as the trimer, tetramer, pentamer or oligomer of the compounds, or mixtures thereof, forming three, four, five or multiple menaquinol units bonded by the free phenol —OH groups where available, with the carbonyl linkers as noted in formulae II to VI. The menaquinol derivatives disclosed herein may be obtained as isolatable and stable menaquinol derivatives.

In another aspect, the application discloses a menaquinol derivative that is a dimer salt of the formula:

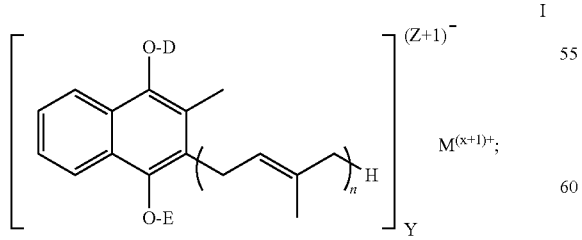

wherein:
each D and E is independently – (a negative charge) or H;
M is a metal or a salt selected from the group consisting of $Li^+$, $Na^+$, $K^+$, $Mg^{2+}$, $Ca^{2+}$, $Al^{3+}$ and $Zn^{2+}$; and arginine, benzathine, chloroprocaine, choline, diethanolamine, ethanolamine, ethylenediamine, lysine, histidine, meglumine, procaine and triethylamine;
X is 0, 1 or 2; Y is 0.5, 1, 2 or 3; Z is 0 or 1; and n is 7, 8, 9 or 10.

In one variation, M is a metal selected from the group consisting of lithium ($Li^+$), sodium ($Na^+$), potassium ($K^+$), magnesium ($Mg^+$), calcium ($Ca^{+2}$) and aluminum ($Al^{+3}$). As provided herein, the charged variables designated in formula I as, for example "$(X+1)^+$" means that when X is 0, then the metal "M" is a $M^{1+}$ or $M^+$, such as $Li^+$, $Na^+$, $K^+$, etc. . . . . . And when X is 1, then the metal "M" is a $M^{2+}$, such as $Ca^{2+}$, $Mg^{2+}$ etc. In one variation, M is $Ca^{2+}$. In one variation of the compound of the formula I, n is 7.

In another aspect, the application discloses a menaquinol derivative that is a dimer of the formula:

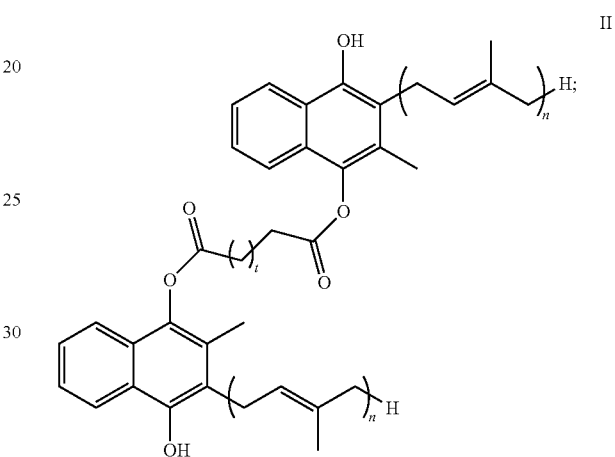

wherein: n is 7, 8, 9 or 10; and t is 0, 1, 2 or 3. In one variation of the compound of the formula II, n is 7. In another variation of the compound of the formula II, n is 9.

In another aspect, the application discloses a menaquinol derivative that is a dimer of the formula:

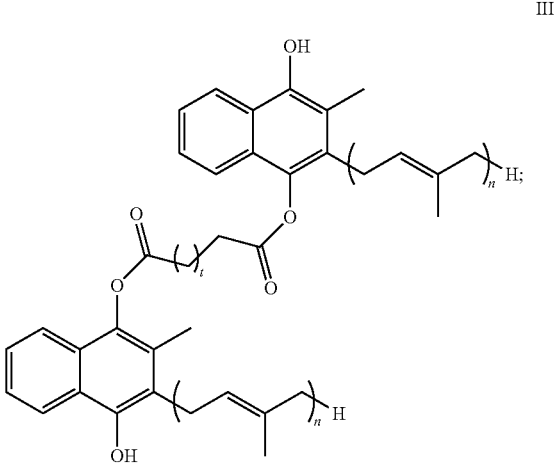

wherein: n is 7, 8, 9 or 10; and t is 0, 1, 2 or 3. In one variation of the compound of the formula III, n is 7. In another variation of the compound of the formula III, n is 9.

In another aspect, the application discloses a menaquinol derivative that is a dimer of the formula:

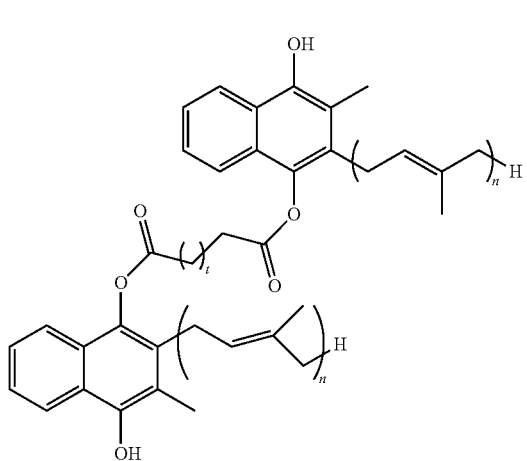

IV wherein: n is 7, 8, 9 or 10; and t is 0, 1, 2 or 3. In one variation of the compound of the formula IV, n is 7. In another variation of the compound of the formula IV, n is 9.

In another aspect, the application discloses a menaquinol derivative that is a dimer of the formula:

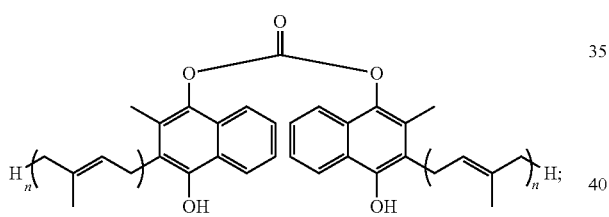

V wherein n is 7, 8, 9 or 10. In one variation of the compound of the formula V n is 7. In another variation of the compound of the formula V, n is 9.

In yet another aspect, the application discloses a menaquinol derivative that is a dimer (forming an acyclic carbonate) of the formula:

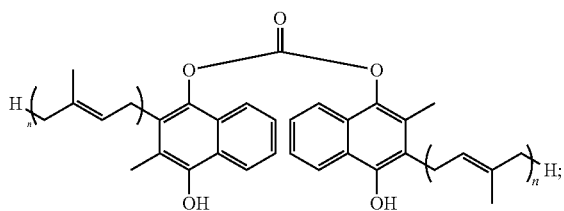

VI wherein n is 7, 8, 9 or 10. In one variation of the compound of the formula VI, n is 7. In another variation of the compound of the formula VI, n is 9.

In yet another aspect, the application discloses a menaquinol derivative that is a dimer (forming a cyclic dicarbonate) of the formula:

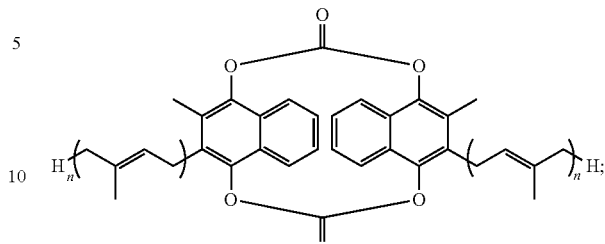

VII and

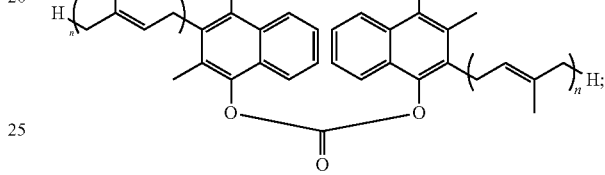

VIII wherein n is 7, 8, 9 or 10. In one variation of the compound of the formula VII, n is 7. In another variation of the compound of the formula VII, n is 9.

In another aspect, the application discloses a menaquinol derivative that is a dimer (forming a cyclic dicarbonate) of the formula:

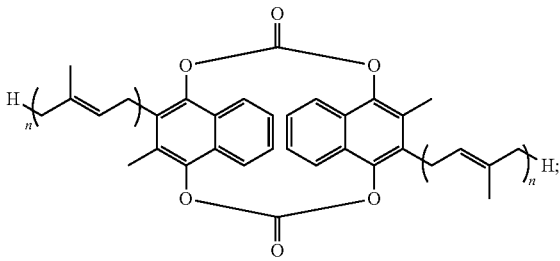

VIII wherein n is 7, 8, 9 or 10. In one variation of the compound of the formula VIII, n is 7. In another variation of the compound of the formula VII, n is 9.

In another aspect, the application discloses a menaquinol derivative that is a carbonate dimer of the formula VIIIa. The preparation of VIIIa, wherein n is 7, 8 or 10, is shown below:

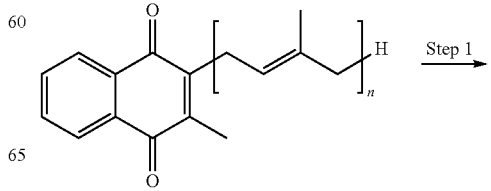

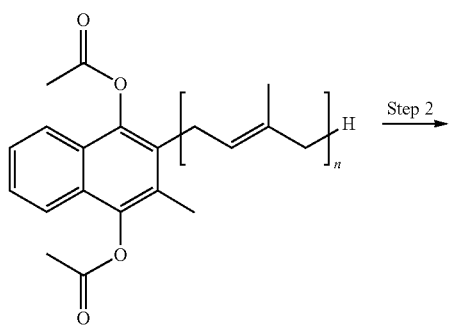

IXa

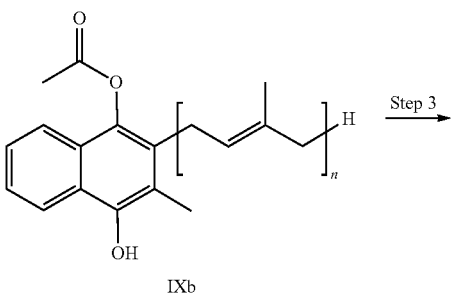

IXb

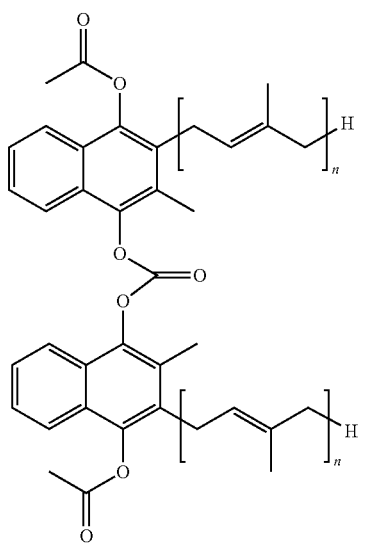

VIIIa

In another aspect, the application discloses a menaquinol derivative that is a carbonate dimer of the formula VIIIb, wherein n is 7, 8 or 10. The preparation of VIIIb is shown below:

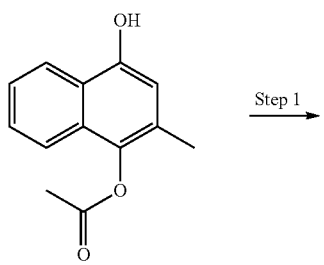

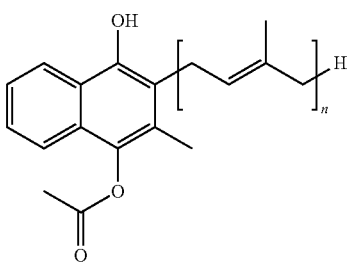

IXc

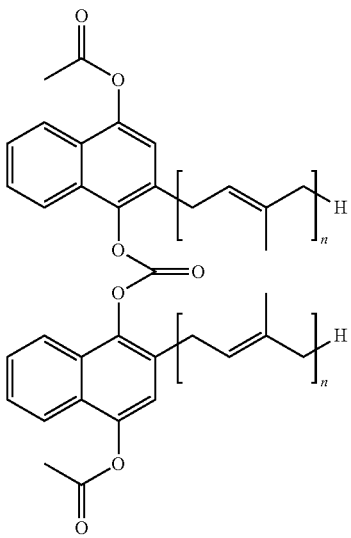

VIIIb

The mono-acetate starting material in Step 1, above, for the preparation of IXc and then the preparation of VIIIb may be prepared as shown below:

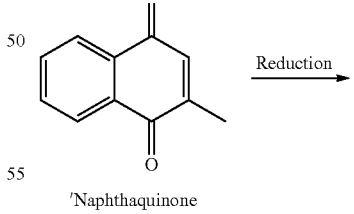

Naphthaquinone

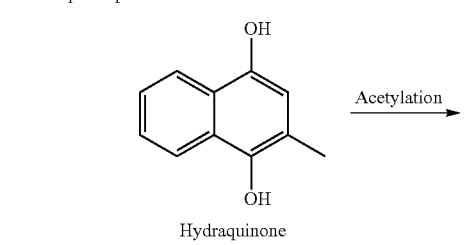

Hydraquinone

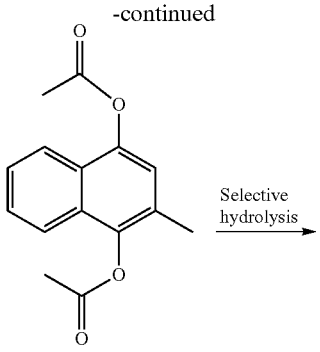

Di-acetate

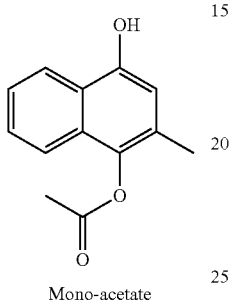

Mono-acetate

The naphthoquinone may be reduced to the corresponding hydroquinone, which may be acylated, such as using acetic anhydride and acetyl chloride, to provide the di-acetate in high yield. The diacetate may be selectively de-acetylated selectively to the corresponding mono-acetate in high yield and with high selectivity, providing >99% of the desired mono-acetate.

In another aspect, the application discloses a menaquinol derivative that is a carbonate dimer of the formula VIIIc, wherein n is 7, 8 or 10. In one variation, n is 7.

VIIIc

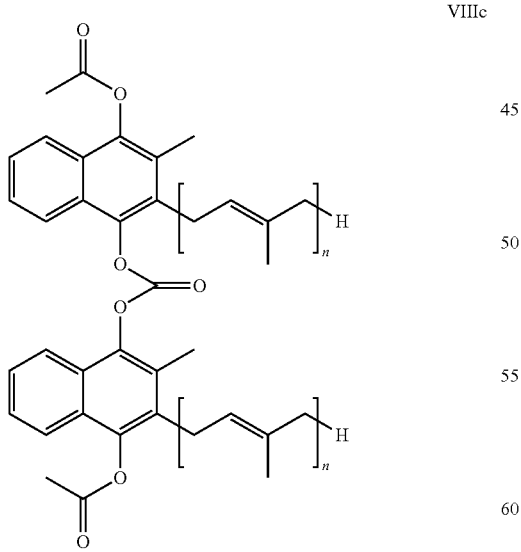

In another aspect, the application discloses a compound of the formulae VIIIa.1, VIIIb.1 and VIIIc.1, wherein each $R^1$ and $R^2$ is independently $C_1$-$C_6$alkyl, or independently methyl, ethyl, propyl, isopropyl, butyl, iso-butyl, pentyl, iso-pentyl, hexyl and iso-hexyl; and each n is independently 7, 8 or 10. In one variation, n is 7. In another variation, $R^1$ and $R^2$ are both methyl.

VIIIa.1

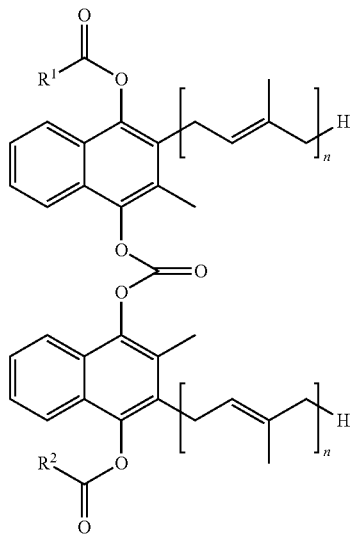

VIIIb.1

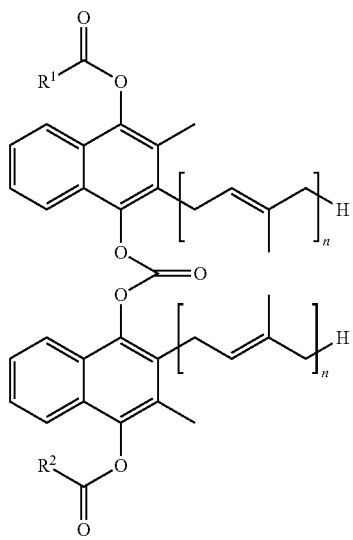

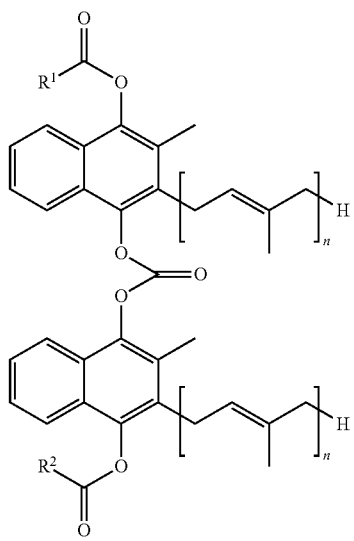
VIIIc.1
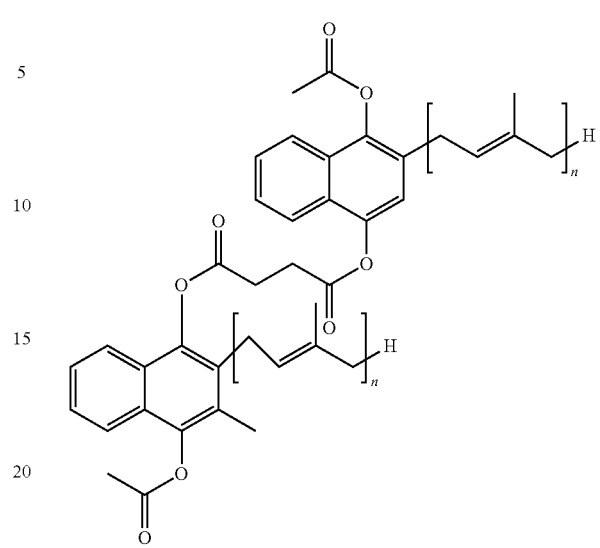
IX.01
In another aspect, the application discloses a menaquinol derivative of the formulae IX, IX.01 and IX.0a wherein each n is independently 7, 8 or 10. In one variation, n is 7.
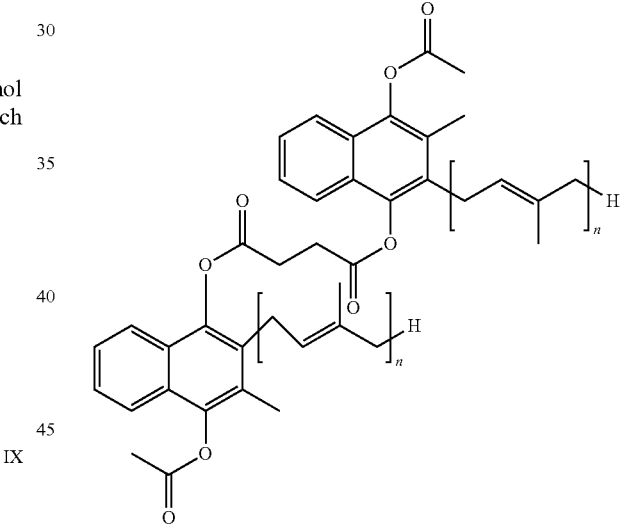
IX.0a
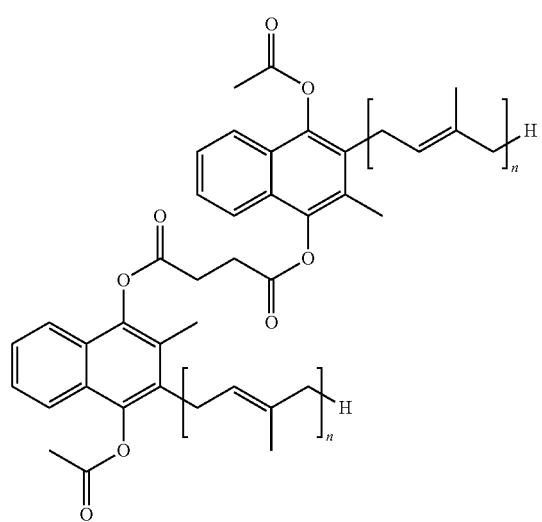
IX
In one variation, the application discloses a process for the preparation of the compound of the formulae IXa, IXb, IXc, IXd and IX:
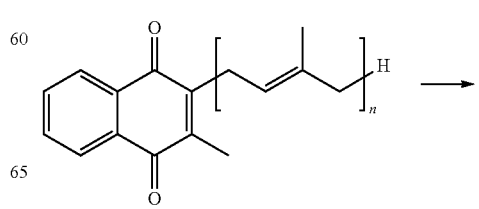

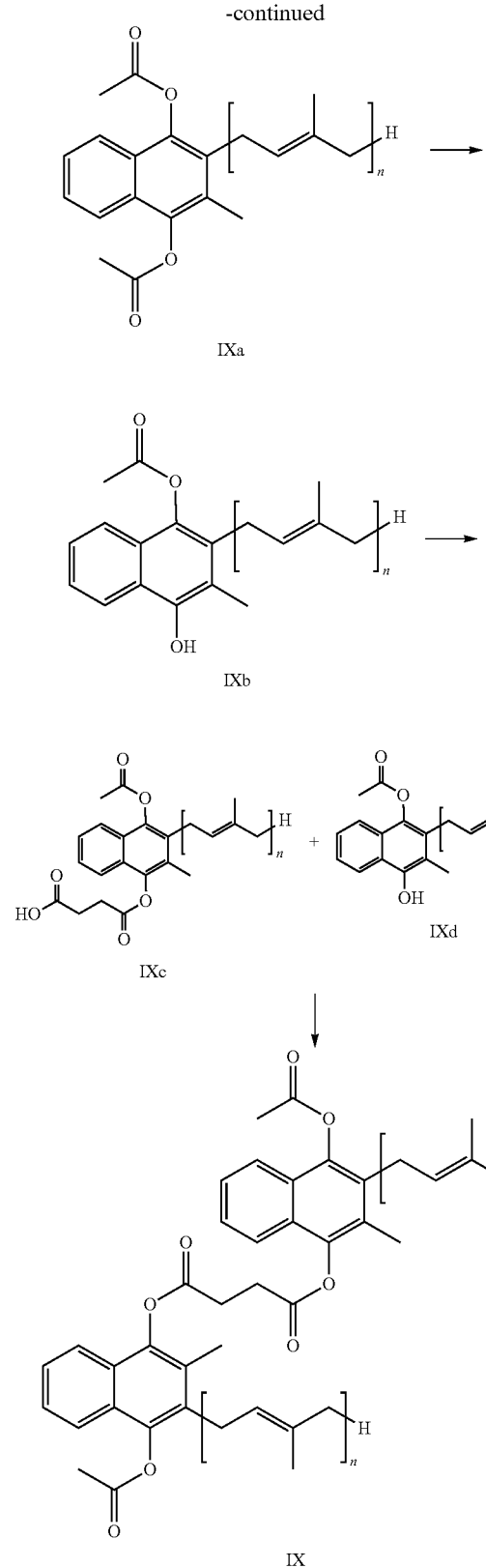
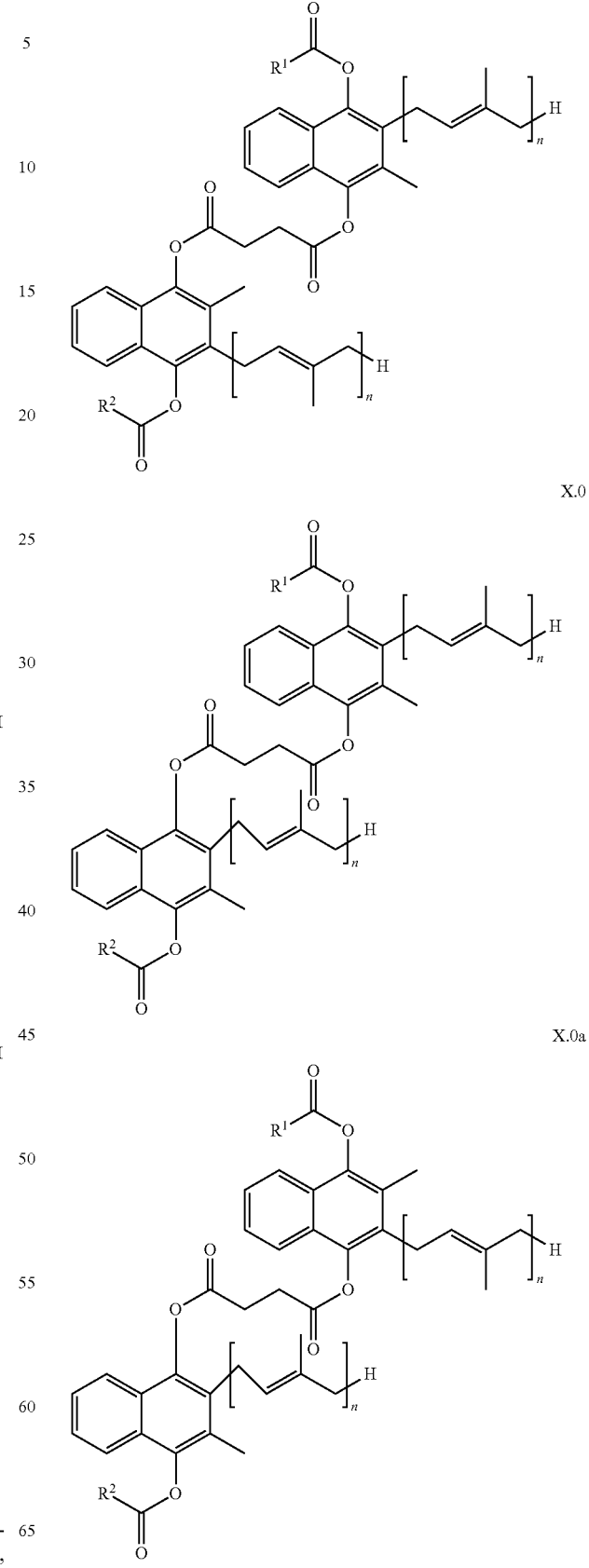
wherein n is 7, 8 or 10. In one variation, n is 7.
In another variation, the application discloses the compound of the formulae IX.0, X.0, X.0a, IX.1, IX.2, X.0b, X.1, X.2, and X.2a.

-continued
IX.1
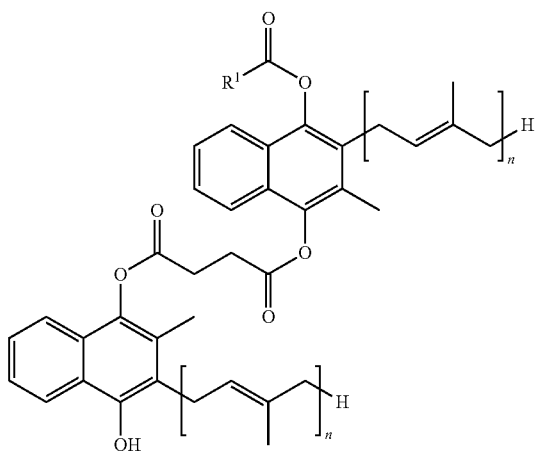
IX.2
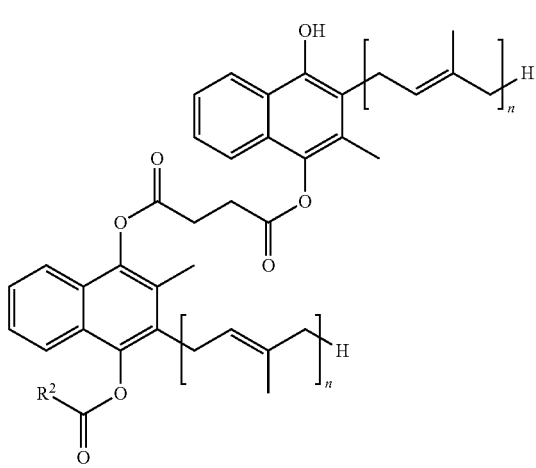
X.0b
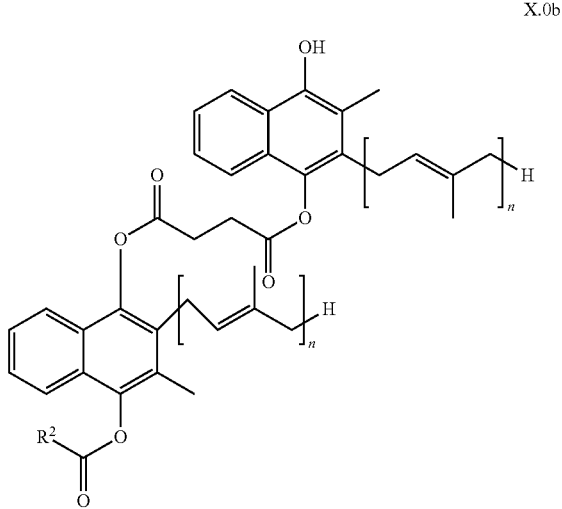
-continued
X.1
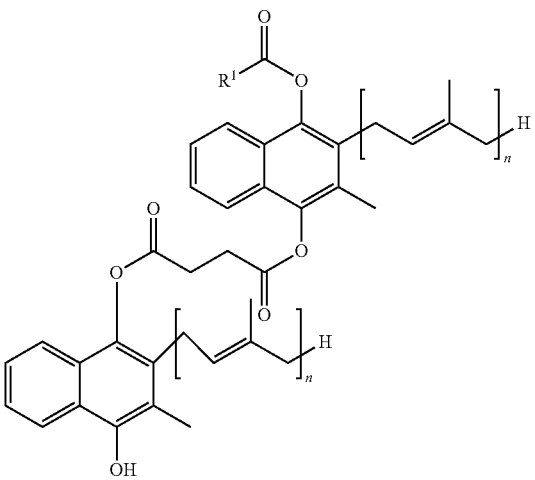
X.2
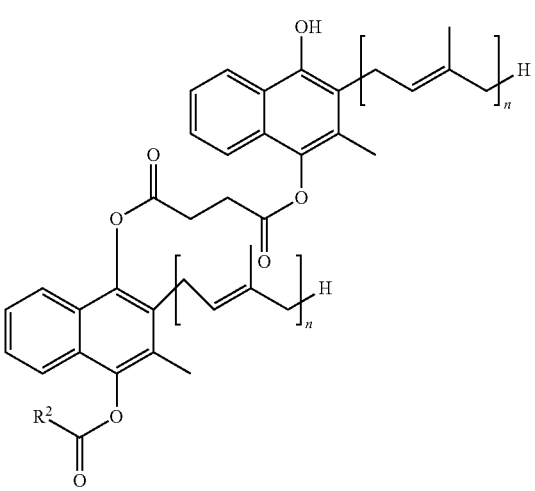
X.2a
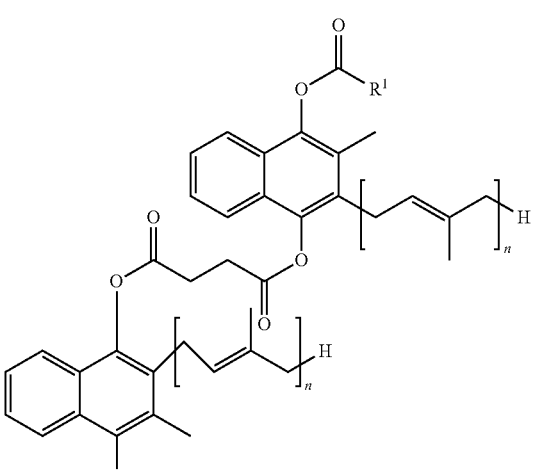
wherein for compounds IX.0, X.0 and X.0_a each $R^1$ and $R^2$ is independently $C_1$-$C_6$alkyl, or independently methyl, ethyl, propyl, isopropyl, butyl, iso-butyl, pentyl, iso-pentyl, hexyl and iso-hexyl. In one variation of the compounds IX.0, X.0 and X.0a, $R^1$ and $R^2$ are both —$CH_3$. In one variation of the compounds IX.1, X.1 and X.2a, $R^1$ is $C_1$-$C_6$alkyl. In one variation of the compounds IX.2, X.0b and X.2, $R^2$ is $C_1$-$C_6$alkyl. In another variation of the compounds IX.1, X.1 and X.2a, $R^1$ is —$CH_3$ (methyl). In another variation of the compounds IX.2, X.0b and X.2, $R^2$ is —$CH_3$. In one aspect, n is 7, 8 or 10. In another variation, n is 7.
In another variation, the application discloses the compound of the formulae XI.0 to XI.8:
XI.0
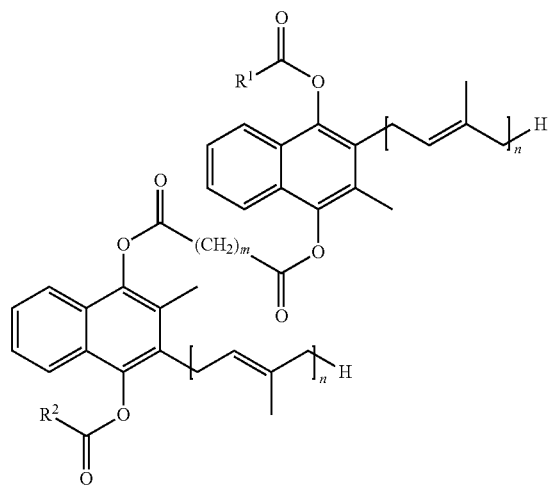
XI.1
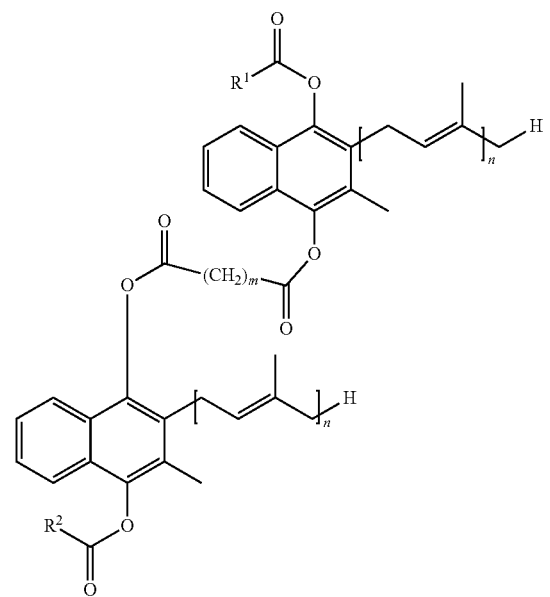
-continued
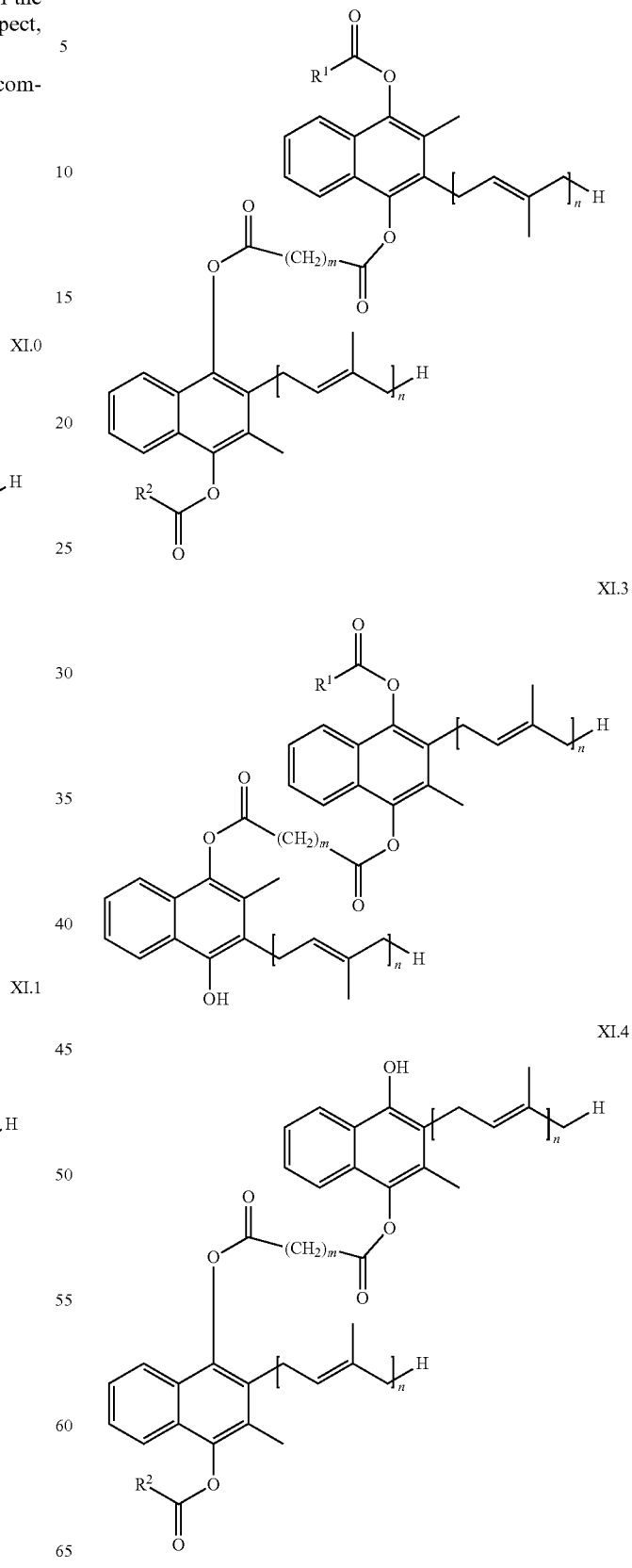

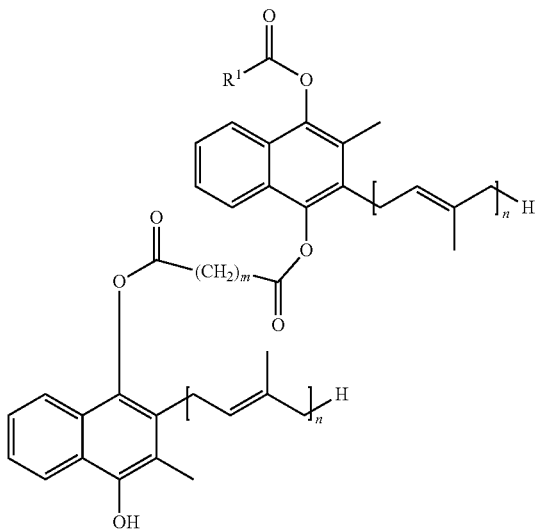

XI.5

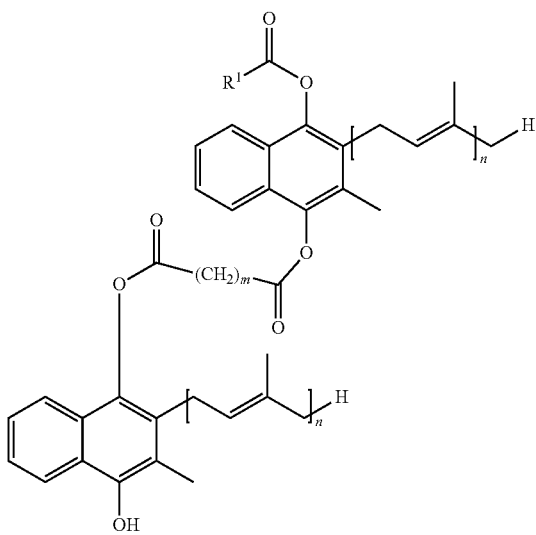

XI.6

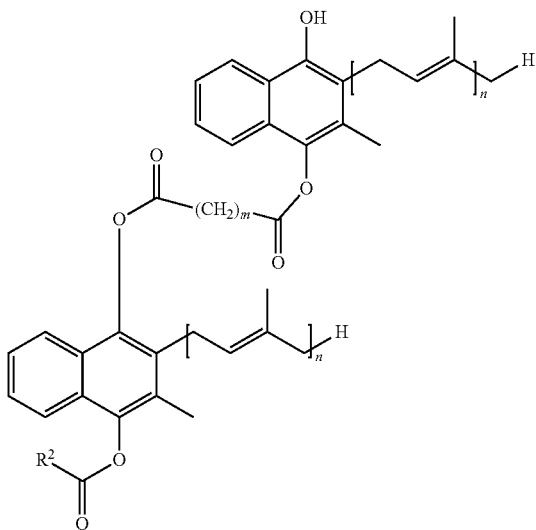

XI.7

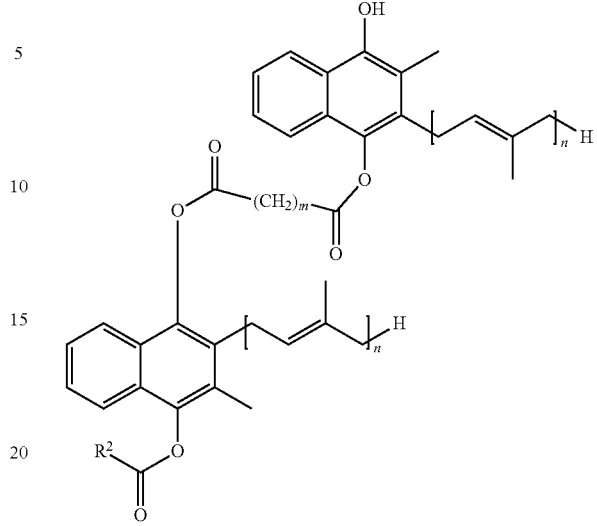

XI.8 wherein for compounds XI.0, XI.1 and XI.2, each $R^1$ and $R^2$ is independently $C_1$-$C_6$alkyl, or independently methyl, ethyl, propyl, isopropyl, butyl, iso-butyl, pentyl, iso-pentyl, hexyl and iso-hexyl. In one variation of the compounds XI.0, XI.1 and XI.2, $R^1$ and $R^2$ are both —$CH_3$. In one variation of the compounds XI.3, XI.5 and XI 6 $R^1$ is $C_1$-$C_6$alkyl. In one variation of the compounds XI.4, XI.7 and XI.8, $R^2$ is $C_1$-$C_6$alkyl. In another variation of the compounds XI.3, XI.5 and XI.6, $R^1$ is —$CH_3$ (methyl). In another variation of the compounds XI.4, XI.7 and XI.8, $R^2$ is —$CH_3$. In one aspect of the above compounds, m is 1, 2, 3, 4 or 5, and n is 7, 8 or 10. In one variation, m is 1; or m is 2. In another variation of each of the above menaquinol derivatives, n is 7.

In another variation of the above menaquinol derivatives, $R^1$, where present, is $C_1$-$C_6$ alkyl. In another variation of the above, $R^2$, where present, is $C_1$-$C_6$ alkyl. In another variation, each of $R^1$ and $R^2$ where present in a single molecule, is independently $C_1$-$C_6$ alkyl. As used herein, for example, $C_1$-$C_6$ alkyl include methyl, ethyl, propyl, isopropyl, butyl, iso-butyl, pentyl, iso-pentyl, hexyl and iso-hexyl. In another variation of the above, $R^1$ is methyl, and $R^2$ is methyl.

Preparation of MK-7, MK-8 and MK-10 Via an Allylation Reaction and Retro-Diels-Alder Reaction:

The preparation of MK-7 may be performed in the general scheme as shown below. Depending on the desired process and optimized processing parameters, the synthesis or reaction process may be performed neat, or in the absence of any organic solvents. Similarly, the preparation of the corresponding MK-8 and MK-10 may be prepared starting with the appropriate side chain to form the desired product. Accordingly, the ketone-cyclopendiene adduct may be alkylated with an excess of a selected allyl derivative, such as the allyl halide, such as an allyl bromide, or an allyl tosylate derivate or an allyl mesylate derivative, in at least about 1.2 equivalent, or at least 1.5, 2.0 or 2.5 equivalent. The reaction may be conducted in the presence of a base sufficient to deprotonate the bridge hydrogen, such as a metal alkoxide, such as sodium tert-butoxide or potassium tert-butoxide. While the reaction may be conducted in a solvent, such as THF or diethyl ether, the reaction may be performed neat, or in the absence of any solvent to provide the desired product in about 1 hour. Optionally, the desired product may be diluted with a solvent, such as THF, diethyl ether, hexanes or mixtures thereof, and then filtered and isolated from residual salts and by-products. Filtration of the crude product may be conducted with a short column or plug of silica gel. Removal of the solvent in vacuo provides the desired product. The desired intermediate product may be used as is, or further purified, if desired. The intermediate product may be placed under vacuum, such as 15 torr or less, and then heated to about 85° C., optionally in the absence of stirring. Once the reaction is determined to be complete over at least 5 hours or about 12 hours, using TLC or HPLC, the resulting product was purified, such as using flash column chromatography, in a solvent, such as 4%-10% diethyl ether in hexanes, and then the solvents are removed under vacuo to provide the desired MK-7 product (MK-8 or MK-10) in about 80% yield over the two reaction steps.

pH-5) at 0, 30, 60, 120 and 240 minutes. The % of the compound disappearing over time was calculated by comparing to peak areas of analyte at '0' minute by HPLC/LCMS analysis. Formation of menaquinone-7 from the tested was observed.

Stability in Human and Rat Plasma:

A Table 4 noting the stability of the disclosed compounds as tested is determined in Human and Rat plasma ($K_2EDTA$) at 0, 15, 30, 60 and 120 minutes. The % of compound disappearing over time is calculated by comparing to 0 minute by HPLC/LC-MS-MS analysis. Formation of menaquinone-7 from the tested compounds was observed at time intervals of t=0, 30 mins, 60 mins and 120 mins.

A Table 5 noting the stability of the disclosed compounds as tested is determined in Human and Rat plasma ($K_2EDTA$) at 0, 15, 30, 60 and 120 minutes. The formation of mena-

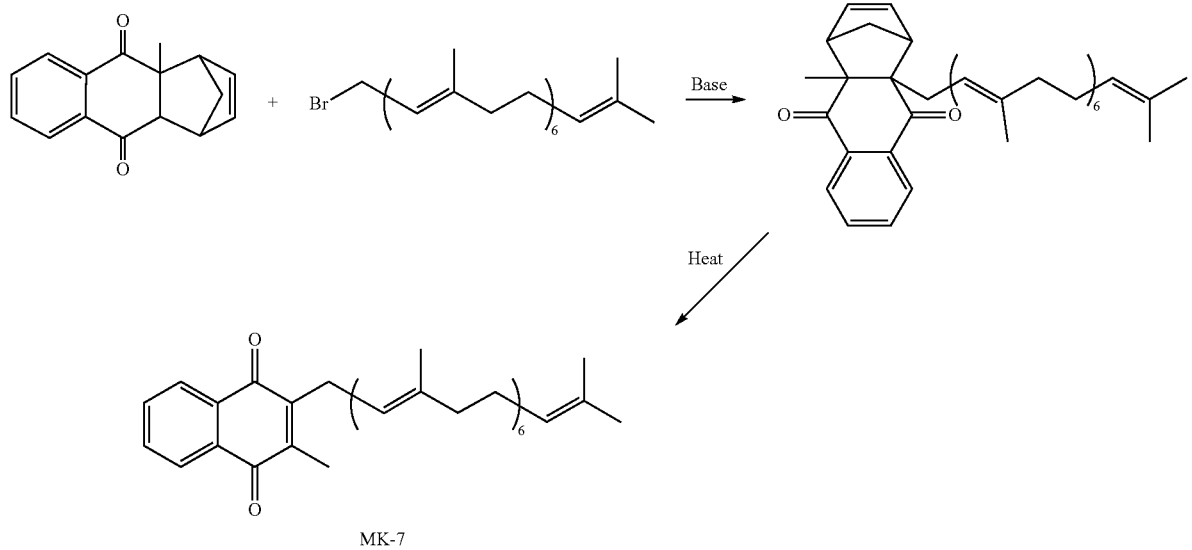

MK-7

Stability of the Compounds in SGF, FaSSIF and FeSSIF:

Stability of the disclosed compounds, such as the disclosed compounds as tested may be determined in Simulated gastric fluid (SGF, pH-1.2), Fasted state simulated intestinal fluid (FaSSIF, pH-6.5) and Fed state simulated intestinal fluid (FeSSIF, pH-5) at 0, 30, 60, 120 and 240 minutes. The % of compound disappearing over time may be calculated by comparing to peak areas of analyte at '0' minute by HPLC/LCMS analysis. Formation of the menaquinone, such as menaquinone-7 from the compounds tested, as disclosed herein, was observed.

A Table 1 is prepared to summarize the stability of the disclosed compounds as tested, noting SGF (pH 1.2); FaSSIF (pH 6.5) and FeSSIF (pH 5.0) noting the % compounds remaining as compared to 0 min, at time intervals of t=0, 30 mins, 60 mins, 120 mins and 240 mins.

A Table 2 is prepared to summarize the stability of the disclosed compounds as tested, noting SGF (pH 1.2); FaSSIF (pH 6.5) and FeSSIF (pH 5.0) noting the formation of menaquinone-7, in terms of Fold change compared to 0 min, at time intervals of t=0, 30 mins, 60 mins, 120 mins and 240 mins.

A Table 3 noting the stability of the disclosed compounds as tested is determined in Simulated gastric fluid (SGF, pH-1.20), Fasted state simulated intestinal fluid (FaSSIF, pH-6.5) and Fed state simulated intestinal fluid (FeSSIF, quinone-7, based on Fold change compared to 0 mins, is calculated by comparing to 0 minute by HPLC/LC-MS-MS analysis. The % of the tested compound remaining is observed at time intervals of t=0, 30 mins, 60 mins and 120 mins.

A Table 6 noting the stability of the disclosed compounds as tested is determined in Human and Rat plasma ($K_2EDTA$) at 0, 15, 30, 60 and 120 minutes. The stability of the tested compounds, based on the formation of menaquinone-7 and based on Fold change compared to 0 mins, is calculated by comparing to 0 minute by HPLC/LC-MS-MS analysis, and is observed at time intervals of t=0, 30 mins, 60 mins and 120 mins.

A Table 7 noting the stability of the disclosed compounds as tested, was determined in Human and Rat plasma ($K_2EDTA$) at 0, 15, 30, 60 and 120 minutes. The % of compound disappearing over time was calculated by comparing to 0 minute by HPLC/LC-MS-MS analysis. Formation of menaquinone-7 from the tested compounds was observed.

In Vivo Testing:

Brief Procedure:

Male Sprague Dawley rats aged 8-10 weeks and weighing around 202-223 grams are used for in vivo testing. Animals are fasted overnight with free access to water. Animals are split into 4 groups G1 to G4, each group containing 3 rats.

To determine the bioavailability, the test items Are separately dissolved in corn oil to obtain homogenous formulations. Animals are administered with test items by oral gavage, animals of G1 received 1088 µg, G2 received 1073 µg, G3 and G4 received 1000 µg per kg body weight dose of VIIIb (n=7) (G1), of VIIIb (n=9) (G2), menaquinone-7 (G3) and menaquinone-9 (G4) respectively. The doses of VIIIb (n=7) (G1), of VIIIb (n=9) were adjusted for the menaquinol content. Blood samples were collected at various time points during the next 48 hours post dose.

Blood samples were collected and transferred to tubes containing $K_2EDTA$ and immediately placed on ice for plasma preparations. Plasma was prepared by centrifugation at 3500 g for 10 min, aliquots were frozen at −80° C. until analysis. Quantification of analyte in plasma was determined by LC-MS-MS analysis. Plasma PK parameters were calculated using WinNonlin software.

In another embodiment, the application discloses a pharmaceutical composition comprising a therapeutically effective amount of a menaquinol derivative of any one of the above embodiments and aspects, or a mixture thereof; and a pharmaceutically acceptable excipient, wherein the composition is effective for the treatment of a condition associated with vitamin K selected for the treatment of osteoporosis, arteriosclerosis, calciphylaxis or tissue calcification.

In another embodiment, the application discloses a method for increasing the tissue concentration of menaquinol as a co-factor for gamma glutamate carboxylase (GGCX) for catalyzing the carboxylation of vitamin K dependent proteins that is associated with the treatment or prevention of osteoporosis, arteriosclerosis, calciphylaxis or tissue calcification in a patient in need thereof, the method comprising an administration of a therapeutically effective amount of a menaquinol derivative or a pharmaceutical composition comprising an effective amount of a menaquinol derivative as disclosed above, or a mixture thereof.

In one variation of the method, the administration of the menaquinol derivative overcomes the oxidative block in patients with CKD and in patients receiving hemodialysis and provides maximal levels of menaquinol and maximal benefits at the tissue level. In one variation, the tissue is the skin or dermis tissue. In another variation, the tissue is at least of of the patient's mitral valve, the patient's artic valve and blood vessels. In another variation of the method, the menaquinol is menaquinol-7. In another variation, the menaquinol is menaquinol-9. In another variation, the method increases the tissue concentration of menaquinol by at least 20%, 30%, 40%, 50%, 100%, 150%, 200%, 250%, 300%, 400% or 500% or more when compared to the administration of menaquinone.

In another embodiment, the application discloses a method for the treatment of a disease in a mammal selected from the group consisting of neurodegenerative diseases, retinopathy, rheumatoid polyarthritis, atherosclerosis, amyotrophic lateral sclerosis, cerebral ischemia, cataracts, systemic infections, pathologies associated with cutaneous aging and with senescence in tissues, pathologies associated with mitochondrial dysfunction, cachexia associated with under nutrition, wherein the treatment is associated with the increase in the longevity of mammals, the method comprises the administration of a therapeutically effective amount of a compound or composition comprising a menaquinol derivative of the formulae formulae I to XI.8, inclusive of all disclosed compounds, or a mixture thereof.

In another aspect, the application discloses a method for treating a mammal with a disease selected from the group consisting of vitamin K deficiency, osteoporosis, a proliferative disease, and a cardiovascular disease, comprising administering to the mammal a therapeutically effective amount of a menaquinol derivative as disclosed above, or a mixture thereof. In another aspect of the method, the proliferative disease is selected from the group consisting of cancer, leukemia and an inflammatory disease. In another aspect, the application discloses a method for the treatment or prevention of osteoporosis and/or osteopenia, the method comprising administering to a patient in need of treatment, a therapeutically effective amount of a composition comprising a menaquinol derivative of the formulae I to XI.8 or a mixture thereof.

In another aspect, the application discloses a method of treating, preventing, slowing the progression of, arresting, and/or reversing calciphylaxis in a mammal in need thereof, the method comprising administering to the mammal a therapeutically effective amount of a composition comprising substantially pure menaquinol derivative of the formulae I to XI.8 or a mixture thereof, and a pharmaceutically acceptable excipient, to prevent, slow the progression of, arrest, or reverse calciphylaxis. In another aspect of the method, the mammal has distal calciphylaxis and/or central calciphylaxis. In another aspect of the method, the mammal has diabetes, chronic kidney disease or end stage renal disease. In another aspect of the method, the mammal has stage 3, stage 4 or stage 5 chronic kidney disease. In another aspect of the methods, the mammal is undergoing hemodialysis. In yet another aspect of the method, the mammal is receiving non-warfarin-based anti-coagulant therapy. In another aspect of the method, the anti-coagulant therapy is oral anti-coagulation therapy. In yet another aspect of the method, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigatran or argatroban.

In another aspect of the above methods, the mammal has chronic obstructive pulmonary disease (COPD). In another aspect of the methods, the mammal has a calciphylaxis-related dermal lesion. In another aspect, the administration of the composition reduces the total surface area of the dermal lesion by at least 10%, 20%, 30%, 40%, 50%, 60%, 70%, 80%, 90% or 100%. In another aspect of the method, the administration of the compound of the formulae I to XI.8 or a mixture thereof, to the mammal increases the mammal's serum T50 value by at least 10%, 20%, 30%, 40%, 50%, 60%, 70%, 80%, 90% or 100% relative to the mammal's serum T50 value prior to administration of the above compound, or a mixture thereof. In yet another aspect of the method, the administration of the compound of the formulae I to XI.8 or a mixture thereof, increases a ratio of a carboxylated to a non-carboxylated of a Vitamin K dependent protein in plasma of the mammal after administration of the composition is greater than prior to administration of the composition.

In another embodiment, there is provided a method of treating, preventing, slowing the progression of, arresting and/or reversing tissue calcification in a pre-diabetic mammal (or subject) with diabetes, chronic kidney disease or a combination thereof, and in need thereof, the method comprising administering to the mammal at least 50 mg of a compound of the formulae I to XI.8 or a mixture thereof per day, to prevent, slow the progression of, and/or arrest tissue calcification, wherein the above compound, or a mixture thereof, is administered in a pharmaceutical composition.

In each of the above recited methods, the specification also discloses the recited compounds or compositions thereof, for use as a medicament in the treatment of the recited medical conditions or diseases; and the specification discloses the use of the recited compounds in the manufacture of a formulation or medicament for the treatment of the disclosed medical conditions or diseases.

In one variation, the menaquinol derivative is administered at a dose of at least 5 mg, 10 mg, 20 mg, 30 mg, 40 mg or 50 mg. In another variation, the menaquinol derivative is administered at a dose of at least 100 mg, 150 mg, 200 mg, 25 mg, 300 mg, 350 mg, 400 mg 450 mg or 500 mg. In another variation, the menaquinol derivative is administered at a dose of at least 500 mg, 600 mg, 700 mg, 800 mg, 900 mg or 1,000 mg or more.

In one aspect of the above method, the mammal has diabetes. In another aspect, the mammal has type II diabetes. In another aspect, the mammal has been diagnosed as pre-diabetic. In another aspect of the above method, the mammal has chronic kidney disease. In yet another aspect of the method, the mammal has stage 4 or 5 chronic kidney disease/end stage renal disease. In another aspect of the method, the mammal is undergoing hemodialysis. In another aspect of the method, the mammal is receiving non-warfarin based anti-coagulant therapy. In another aspect of the method, the anti-coagulant therapy is oral anti-coagulation therapy. In yet another aspect of the method, anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban.

In another embodiment, the application discloses a method of treating, preventing, slowing the progression of, arresting, and/or reversing tissue calcification in a mammal undergoing hemodialysis, and in need thereof, the method comprising administering to the mammal at least 5 mg of the compound of the formulae I to XI.8 or a mixture thereof, per day, thereby to prevent, slow the progression, arrest, and/or reverse tissue calcification, wherein the above compound, or a mixture thereof is administered in a pharmaceutical composition.

In one variation, the menaquinol derivative is administered at a dose of at least 5 mg, 10 mg, 20 mg, 30 mg, 40 mg or 50 mg. In another variation, the menaquinol derivative is administered at a dose of at least 100 mg, 150 mg, 200 mg, 25 mg, 300 mg, 350 mg, 400 mg 450 mg or 500 mg. In another variation, the menaquinol derivative is administered at a dose of at least 500 mg, 600 mg, 700 mg, 800 mg, 900 mg or 1,000 mg or more. In another aspect of the above method, the mammal has diabetes.

In another aspect, the application discloses a pharmaceutical composition comprising a therapeutically effective amount of a menaquinol derivative (or also referred to as "a compound" or "disclosed compound(s)") as disclosed above, or a mixture thereof, and a pharmaceutically acceptable excipient, wherein the composition is effective for the treatment of a condition associated with vitamin K selected from for the treatment of osteoporosis and arteriosclerosis.

In another aspect, the present application discloses a method for the treatment of a disease in a mammal selected from the group consisting of neurodegenerative diseases, retinopathy, rheumatoid polyarthritis, atherosclerosis, amyotrophic lateral sclerosis, cerebral ischemia, cataracts, systemic infections, pathologies associated with cutaneous aging and with senescence in tissues, pathologies associated with mitochondrial dysfunction, cachexia associated with under nutrition, wherein the treatment is associated with the increase in the longevity of mammals, the method comprises the administration of a therapeutically effective amount of a compound or composition comprising a menaquinol compound as disclosed above, or a mixture thereof.

In another embodiment, there is provided a method for treating a mammal with a disease selected from the group consisting of vitamin K deficiency, osteoporosis, a proliferative disease, and a cardiovascular disease, comprising administering to the mammal a therapeutically effective amount of a compound as disclosed herein, or a mixture thereof. In another aspect of the method, the proliferative disease is selected from the group consisting of cancer, leukemia and an inflammatory disease.

In another embodiment, there is provided a method for the treatment or prevention of osteoporosis and/or osteopenia, the method comprising administering to a patient in need of treatment, a therapeutically effective amount of a composition comprising a compound as disclosed above, or a mixture thereof. The disclosed method for the administration of MK-7 and its fat-soluble hydroquinone derivatives, or combinations thereof, may be used in the treatment or reduction of vascular calcification, increase in bone mineral density and for the treatment, reduction or prevention of bone diseases, such as in patients with CKD.

In another embodiment, there is provided a method of treating, preventing, slowing the progression of, arresting, and/or reversing calciphylaxis in a mammal in need thereof, the method comprising administering to the mammal a therapeutically effective amount of a composition comprising substantially pure menaquinol compound as disclosed herein, and a pharmaceutically acceptable excipient, to prevent, slow the progression of, arrest, or reverse calciphylaxis. In one aspect of the method, the mammal has distal calciphylaxis and/or central calciphylaxis. In another aspect, the mammal has diabetes, chronic kidney disease or end stage renal disease. In another aspect, the mammal has stage 3, stage 4 or stage 5 chronic kidney disease. In another aspect of the method, the mammal is undergoing hemodialysis. In yet another aspect, the mammal is receiving non-warfarin-based anti-coagulant therapy.

In another aspect of the above method, the anti-coagulant therapy is oral anti-coagulation therapy. In another aspect, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban. In another aspect, the mammal has chronic obstructive pulmonary disease (COPD). In another aspect, the mammal has a calciphylaxis-related dermal lesion. In another aspect of the method, administration of the composition reduces the total surface area of the dermal lesion by at least 10%, 20%, 30%, 40%, 50%, 60%, 70%, 80%, 90% or 100%. In another aspect of the method, administration of the substantially pure compound as disclosed herein, to the mammal increases the mammal's serum T50 value by at least 10%, 20%, 30%, 40%, 50%, 60%, 70%, 80%, 90% or 100%) relative to the mammal's serum T50 value prior to administration of the disclosed compound. In another aspect, administration of the disclosed compound increases a ratio of a carboxylated to a non-carboxylated of a Vitamin K dependent protein in plasma of the mammal after administration of the composition is greater than prior to administration of the composition. In one aspect of the method, the increase of the ratio of a carboxylated to a non-carboxylated of a Vitamin K dependent protein in plasma of the mammal after administration of the composition is by at least 5%, 10%, 15%, 20%, 25%, 30%, 35%, 40%, 45% 50%, 55%, 60%, 65%, 70%, 75%, 80%, 85%, 90%, 95%, or 100% relative to the ratio prior to administration.

In certain embodiments of the above, the administration of the disclosed compounds decreases the amount of a non-carboxylated Vitamin K-dependent protein in the subject's plasma, for example, by at least 5%, 10%, 15%, 20%, 25%, 30%, 35%, 40%, 45% 50%, 55%, 60%, 65%, 70%, 75%, 80%, 85%, 90%, 95% or 100% relative to the amount prior to administration of the compounds. In certain variations, the Vitamin K-dependent protein is selected from Matrix Gla Protein (MGP), Growth Arrest Specific Gene 6 (Gas-6) protein, PIVKA-II protein, osteocalcin, activated Protein C, activated Protein S, factor II, factor VII, factor IX, and factor X.

In certain variation of the above methods, the administration of the compounds increases the plasma level of osteoprotegerin or Fetuin A, for example, by at least 5%, 10%, 15%, 20%, 25%, 30%, 35%, 40%, 45% 50%, 55%, 60%, 65%, 70%, 75%, 80%, 85%, 90%, 95%, or 100% relative to the plasma concentration of osteoprotegerin or Fetuin A prior to administration of the compounds. In other variations, the administration of the compounds decreases the plasma level of D-Dimer or Highly Sensitive C Reactive Peptide (hs-CRP), for example, by at least 5%, 10%, 15%, 20%, 25%, 30%, 35%, 40%, 45% 50%, 55%, 60%, 65%, 70%, 75%, 80%, 85%, 90%, 95% or 100% relative to the plasma concentration of D-Dimer or Highly Sensitive C Reactive Peptide (hs-CRP) prior to administration of the compounds.

In certain variations, the method may include administering from about 20 mg to about 750 mg of the compound to the subject per day. In other variations, the method may include administering from about 50 mg to about 750 mg of the compound to the subject per day. In other variations, the method may include administering from about 20 mg to about 500 mg of the compound to the subject per day. In other variations, the method may include administering from about 50 mg to about 500 mg of the compound to the subject per day. In certain variations, the method can include administering from about 20 mg to about 250 mg of the compound to the subject per day. In other variations, the method may include administering from about 5 mg to about 250 mg of the compound to the subject per day. In other variations, the method may include administering from about 20 mg to about 100 mg of the compound to the subject per day. In other variations, the method may include administering from about 50 mg to about 100 mg of the compound to the subject per day. In other variations, the method may include administering from about 5 mg to about 75 mg of the compound to the subject per day, for example, administering 5, 10, 25, 50, 75, 100, 200, 300, 400 or 500 mg of the compound to the subject per day.

In certain variations, the compound is administered to the subject for at least 2 weeks, 4 weeks, 6 weeks, 8 weeks, 3 months, 6 months, 1 year, or indefinitely as needed. If the subject is undergoing hemodialysis, the compound may be administered to the subject for a period that includes at least the duration of hemodialysis.

In another variation of the method for treatment of calciphylaxis, in addition to measuring the change/reduction in lesion size following administration of the disclosed compounds, pre- and post-drug dosing administration, a biopsy may be taken of the relevant lesions using von Kassa Staining to determine tissue levels of PTH and evidence of change in calcium and phosphate deposition in dermal arterioles.

As disclosed herein, the presence of a uremic oxidative blockade is determined by measuring increased plasma lipid peroxidation, e.g., by detection of increased F2 isoprostanes, increased isolevuglandin-plasma protein adducts; increased protein and amino acid oxidation, e.g., by detection of tyrosine residue oxidation, cysteine or methionine residue oxidation, lysine oxidation and threonine oxidation, thiol oxidation and carbonyl formation in plasma proteins; reactive aldehyde formation, e.g., by detecting glyoxal, methylglyoxal, acrolein, glycoaldehyde, and parahydroxy phenacetaldehyde; increased reactive carbonyl compounds, e.g., by measuring hydrazine formation after reaction with 2,4-dinitrophenyihydrazine; diminished plasma glutathione levels and glutathione peroxidase function; and increased ratio of oxidized to reduced thiols.

In another embodiment, there is provided a method of treating, preventing, slowing the progression of, arresting and/or reversing tissue calcification in a pre-diabetic mammal (or subject) with diabetes, chronic kidney disease or a combination thereof, and in need thereof, the method comprising administering to the mammal at least 2 mg of substantially pure compound as disclosed herein per day, to prevent, slow the progression of, and/or arrest tissue calcification, wherein the compound is administered in a pharmaceutical composition. In another aspect of the method, the mammal has diabetes. In yet another aspect, the mammal has type II diabetes; or the mammal has been diagnosed as pre-diabetic. In another aspect, the mammal has chronic kidney disease. In another aspect of the above method, the mammal has stage 4 or 5 chronic kidney disease/end stage renal disease. In yet another aspect, the mammal is undergoing hemodialysis. In another aspect, the mammal is receiving non-warfarin based anti-coagulant therapy. In another aspect, the anti-coagulant therapy is oral anti-coagulation therapy. In another aspect of the method, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban.

In another embodiment, there is provided a method of treating, preventing, slowing the progression of, arresting, and/or reversing tissue calcification in a mammal undergoing hemodialysis, and in need thereof, the method comprising administering to the mammal at least 2 mg of substantially pure compound as disclosed herein per day, thereby to prevent, slow the progression, arrest, and/or reverse tissue calcification, wherein the disclosed compound is administered in a pharmaceutical composition. In another aspect, the mammal has diabetes.

Vitamin K Metabolism: Development of vascular and soft tissue calcification following the failure to regenerate reduced forms of vitamin K: Vitamin K is an essential enzymatic co-factor that is required for posttranslational modifications of vitamin K dependent (VKD) proteins. While there are numerous VKD proteins many are clinically relevant to ESRD patients. They include central coagulation factors such as factors II, VII, IX and X as well as intercellular matrix proteins including Matrix GLA-1 and Osteocalcin. Under normal conditions, vitamin K is reduced to vitamin K hydroquinone ($KH_2$) by the enzyme NADPH oxidase. It is only the reduced form of vitamin K that is able to function as a co-factor for gamma glutamate carboxylase (GGCX) which catalyzes the carboxylation of vitamin K dependent proteins. Warfarin blocks the generation of vitamin K hydroquinone by acting as a reductive sink. The enzymatic carboxylation of glutamate residues results in further oxidation of vitamin KH2 to 2-3 epoxide vitamin K (FIG. 2). The final step of the vitamin k cycle requires the enzymatic oxidation of vitamin K 2-3 epoxide back to its native structure. This step is catalyzed by vitamin K oxidative reductase (VKOR) and is a component of the vitamin K cycle that is also blocked by the oxidative effects of Warfarin. The observation that Warfarin blocks both the generation of vitamin K hydroxyquinone (KH2) as well as the regeneration of Vitamin K2 2-3 epoxide helps to explains why the incidence of calciphylaxis and other forms of dystrophic calcification is higher among patients receiving Warfarin therapy.

In one variation, the administration or supplementation of the disclosed compounds and compositions reduces the risk for vascular and soft tissue calcification by increasing the formation of primary calciprotein particles (CPP) composed of Fetuin A and Carboxylated Matrix GLA-1 Proteins. Under normal physiologic conditions plasma calcium and phosphate concentrations are near supersaturation and thus would be expected to precipitate in blood vessels and soft tissue as crystalline hydroxyapatite. The observation that this process does not occur suggests the presence of potent chemical and biologic means for blocking pathologic calcification. Recent studies have shown that circulating calcium phosphate crystals are complexed with two calcification inhibiting proteins to form primary calciprotein particles (CPPs). These protein-mineral complexes are composed of primarily of Fetuin A; a liver derived protein that has been shown to prevent vascular calcification. A second protein in lower quantities is Matrix Gla-I protein that also functions to prevent pathologic calcification. Matrix Gla-1 is a vitamin K dependent protein and early work by Price et. al and others have shown that formation of the Fetuin-Matrix Gla-1 mineral nanoparticles (primary calciproteins CPP) is dependent upon the gamma carboxylation of Matrix Gla-1. Preclinical studies suggest that the calciprotein system functions as an alternative means for preventing pathologic calcification when humoral lines of defense such as pyrophosphate, magnesium and albumin are overwhelmed. The "absorption" of calcium-phosphate crystals by primary CCPs occurs in a coordinated and time-dependent process.

The time to 50% saturation ($T_{50}$) of primary CCPs is an accurate and highly sensitive means for determining the capacity of plasma to "sink" or "absorb" excess calcium phosphate crystals. Patients with a short $T_{50}$ times suggests a reduced capacity to absorb calcium phosphate crystals whereas patients with prolonged $T_{50}$ times are consistent with high capacities. Recent clinical studies have validated the $T_{50}$ test and confirmed that low $T_{50}$ times are associated with increased myocardial infarctions, heart failure and all-cause mortality. Thus, any clinical intervention that can increases the synthesis of circulating primary CCPs will improve the capacity to prevent pathologic calcification. It is noted that because patients with CKD and ESRD exhibits reduced levels of carboxylated Matrix Gla-1 protein and that this process is essential for the formation of primary CPP. Accordingly, supplementation or administration of the disclosed compounds and compositions in CKD or ESRD patients will reduce the risk for pathologic calcification and prevent the development of vascular and soft tissue calcification.

Supplementation or administration of the disclosed compounds or compositions may prevent or slow the development of soft tissue and vascular calcification in dermal tissues by restoring production of Carboxylated Matrix Gla-1 and GAS-6.

The regeneration of Vitamin K involves two key enzymes: vitamin K 2-3 epoxide oxidative reductase (VKOR) and NAD(P)H: quinone oxidoreductase (NQO1). As shown in the figure, VKOR reduces 2-3 Vitamin K epoxide to vitamin K quinone while NADPH reduces Vitamin K quinone to its hydroxyquinone form (KH2). Recent studies have shown that VKOR has two distinct isoforms exist (VKORC-1 and VKORC1-Like-1 [VKORC1-L1]) that differ in both enzymatic properties and tissue distribution. For example, Westhofen et. al has shown that compared to VKORC1, VKOCR-L1 has a 3-fold lower affinity for 2-3 epoxide vitamin K. Subsequent work supported the hypothesis that VKOR-L1 is a specialized isoform that protects against oxidant injury through the regeneration of vitamin K. When cultured HEK 293T cells were incubated with $H_2O_2$, VKOR-L1 expression was increased and evidence of membrane oxidant injury was reduced. The clinical observation that calciphylaxis and vitamin K-dependent vascular calcification are more common in the dermis raises the question of whether there is differential expression of VKOR enzymes in the skin. Casper et. al determined mRNA expression of key enzymes involved in regeneration of vitamin K. Moreover, expression of NADPH in the dermis was below the level of detection. These observations suggest that any condition or procedure (i.e., hemodialysis) that blocks re-constitution of vitamin K predisposes that tissue to pathologic calcification.

The oxidative properties of uremic plasma as well as the oxidative effects of dialysis itself results in a "metabolic block" and an accumulation of 2-3 epoxide vitamin K and a reduction in the intracellular levels of vitamin K2. The "down-stream" effects of this blockade include the inability to gamma carboxylate key proteins involved in preventing soft tissue and vascular calcification. The oxidative effects of hemodialysis exacerbate this effect which may explain in part the predilection of ESRD patients to develop calciphylaxis and vascular calcification.

The relationship between vitamin K and circulating vitamin K dependent proteins in CKD-ESRD Patients: It is widely recognized that despite dietary deficiencies, vitamin K levels among ESRD patients may not be reduced. For example, Holder et al. studied 172 stable dialysis patients and found that only 6% of patients exhibited a clinically significant deficiency in vitamin K. However, when patients were examined for the level of carboxylated osteocalcin, a full 60% of patients has reduced levels. To confirm that was a general effect of reduced vitamin K activity, the authors also measured PIVKA-II; another vitamin K dependent protein. Indeed, a full 90% of both CKD and ESRD patients were found to have reduced levels of carboxylated prothrombin. In a similar study, Pilkey et al. measured the vitamin K1 levels in 142 ESRD patients and found that the majority of patients had adequate vitamin K stores but 93% of patients had uncarboxylated osteocalcin levels that were greater than 20% of total levels. There was no correlation between total vitamin K1 and the levels of circulating of uncarboxylated osteocalcin. This unexpected finding is consistent with the hypothesis that in uremic patients, total vitamin K levels can be normal while generation of reduced forms are blocked by the oxidative properties of uremia.

In one variation, the administration or supplementation or administration of the disclosed compounds and compositions will reverse hemodialysis induced inhibition of vitamin K dependent proteins through normalization of functional reduced forms of vitamin K. The observation that oxidant conditions can disrupt the vitamin K cycle suggests that the oxidant load generated during hemodialysis could contribute to the high rates of vascular and soft tissue calcification observed within the ESRD population. Work by Himmelfarb et al. and others have confirmed that the simply delivery of hemodialysis can lead to the oxidation of numerous tissue proteins. For example, hydroxyl amino acid side chains be oxidized to oxidized to carbonyl groups. In a study of CKD and ESRD patients, Himmelfarb et al. demonstrated using carbonyl side chain oxidation as a measure of global oxidant burden, Himmelfarb et al. demonstrated that both CKD and ESRD patients exhibit a higher percentage (15-fold) (See FIG. 5) of carbonyl proteins compared to normal controls. The percentage of carbonyl proteins was even higher among patients receiving dialysis demonstrating that not only does dialysis reduce oxidant burden, it appears to contribute to it. As shown in FIG. 5, patients with uremia were found to have up to 15-fold higher levels of carbonylated proteins. Accordingly, the oxidative load generated by the delivery of hemodialysis leads to oxidation of the function vitamin K hydroquinone (KH2) to the non-functional native vitamin. The oxidation of $KH_2$ by hemodialysis block its ability to function as a co-factor for GGCX which down-stream leads to reduced gamma carboxylation of vitamin K dependent proteins.

To confirm that uremia and hemodialysis disrupts the vitamin K cycle, the ratio of vitamin K quinone to 2-3 epoxide vitamin K and vitamin K hydroxyquinone (KH2) may be determined in patients with normal renal function, CKD (Stage IV & V) and ESRD patients. To determine whether the very process of hemodialysis further disrupts the vitamin K cycle, we can measure the levels of oxidized vitamin K in immediately prior to hemodialysis, then at mid-dialysis (2 hrs) and 30 minutes post dialysis. Previous studies examining the interactions between Warfarin and vitamin K metabolism have shown that 2-3 Epoxide Vitamin K are readily measured. Compared to controls, patients with CKD and ESRD will have higher levels of 2-3 epoxide vitamin K and lower levels of vitamin hydroquinone (KH2). To determine whether a loss of reduced forms of Vitamin K (KH2) leads to a reduction in the carboxylation of vitamin K dependent proteins, we can measure the levels of the following biomarkers in control, CKD (Stage IV and V) and ESRD (Pre-Post hemodialysis). Matrix GLA-1 protein; Growth Arrest Specific Gene 6 (Gas-6) proteins; PIVAK-II protein; Osteocalcin; Protein C; Protein S; Fetuin A; and Osteoprotegerin (Dialysis Plasma Levels: 6.7±2.2 pmole/L. We extend these studies by including patients receiving stable 3x/week hemodialysis. The levels of carboxylated and uncarboxylated vitamin K dependent proteins in pre-dialysis serum may be compared to levels obtained at hour 2 and the end of a dialysis session. The oxidative effects of dialysis itself will lead to a reduction in the level of carboxylated Vitamin K dependent proteins. As referred to herein, the Vitamin K are Vitamin K2.

In one variation, the administration or supplementation with the disclosed compounds and compositions in ESRD patients with Calcific Uremic Arteriolopathy (Calciphylaxis) will reduce the time of wound healing by preventing calcification of new blood vessels and restoring blood flow: Skin Biopsies: To confirm that supplementation of the disclosed compounds and compositions prevents the development of small vessel calcification and dermal ischemia, we may identify patients with calciphylaxis confirmed by dermal skin biopsy and randomize patients to treatment with menaquinone-7 or placebo. Clinical Endpoints may include the following: 1) Time to Wound Vacuum therapy withdrawal and 2) time for wound healing defined as the time needed for a 50% reduction in collective the surface area of all calciphylaxis wounds.

In another variation, the administration or supplementation with the disclosed compounds and compositions provides a significant increase in the bioavailability of the compounds, including menaquinone-7/menaquinol-7, menaquinone-8/menaquinol-8, menaquinone-9/menaquinol-9 and menaquinone-10/menaquinol-10, and their respective mixtures, when compared to administration or supplementation. In one variation, the bioavailability increases by at least 5%, 10%, 15%, 20%, 30%, 40%, 50% or more, when compared to the administration or supplementation using menaquinone-7, menaquinone-8 and menaquinone-10.

In another variation, the administration or supplementation with the disclosed compounds and compositions provides a significant increase in the serum half life of the compounds, including menaquinone-7/menaquinol-7, menaquinone-8/menaquinol-8, menaquinone-9/menaquinol-9 and menaquinone-10/menaquinol-10, and their respective mixtures, when compared to administration or supplementation. In one variation, the serum half life increases by at least 5%, 10%, 15%, 20%, 30%, 40%, 50% or more, when compared to the administration or supplementation using menaquinone-7, menaquinone-8 and menaquinone-10.

Histopathologic Endpoints: Comparison of Diagnostic dermal biopsy with Protocol repeat dermal biopsy after 12 weeks of Menaquinone-7 therapy. Change in the level of interstitial calcium deposition defined as the change in Von Kossa staining, which may be quantified by digital image color analysis. We may use dermal biopsies to validate the biomarkers at the tissue level. This process allows confirmation of the preventive properties of the disclosed menaquinol derivatives on early vascular calcification. The validation of these biomarkers at the tissue will also enable clinicians to utilize the biomarkers as means to track clinical responsiveness. Calcification of microvasculature precedes development of CUA lesions. The level of calcification will be quantified by Von Kossa calcium staining in the peripheral tissue and normalized as calcium content per unit area. We may use the Von Kossa as a means of confirming the preventive properties of the disclosed menaquinol derivatives on the development of vascular calcification.

In one variation, the supplementation of the disclosed compounds and compositions in ESRD patients with Calcific Uremic Arteriolopathy (Calciphylaxis; CUA) will reduce the time of wound healing by normalizing carboxy Protein C levels in the dermis and preventing primary thrombosis of dermal blood vessels. Accordingly, in one variation, the supplementation or administration of the disclosed compounds or compositions in diabetic patients will prevent the development of vascular dementia by preventing calcification and development of small vessel vasculopathy.

In yet another embodiment, there is provided a fortified food or drink formulation comprising adding to the food or drink a composition comprising a compound of any one of the above compounds, or a mixture thereof.

Also included in the above embodiments, aspects and variations are salts of amino acids such as arginate and the like, gluconate, and galacturonate. Certain of the compounds of the present invention can exist in unsolvated forms as well as solvated forms, including hydrated forms, and are intended to be within the scope of the present invention. Also provided are pharmaceutical compositions comprising pharmaceutically acceptable excipients and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols, or water. Solid carriers include starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa.

The disclosed compounds and compositions may include a solubility enhancer or solubilizer selected from oleic acid, Kolliphor® EL (polyoxyl castor oil or Cremophor EL), Vitamin E TPGS (D-α-tocopherol polyethylene glycol-1000 succinate), PEPI (a polysarcosine-derived emulsifying agent), Maisine® CC (glyceryl monolinoleate), Gelucire® 44/14 (lauroyl polyoxyl-32 glycerides), Miglyol® 812N (esters of saturated coconut and palm kernel oil-derived caprylic fatty acids and glycerin), Plurol® Oleique (Polyglyceryl-6 Dioleate), Lauroglycol™ 90 (propylene glycol monolaurate (type II), Labrasol® (Caprylocaproyl polyoxyl-8 glycerides), Kolliphor® EL (polyoxyl castor oil), Captisol® (SBE-beta-cyclodextrin), Encapsin™ HPB (hydroxypropylbeta-cyclodextrin), Peceol™ (glycerol/glyceryl monooleate (type 40)), sodium deoxycholate, deoxycholic acid, Labrafil® M2125CS (linoleoyl Polyoxyl-6 glycerides) and medium-chain mono- and diglycerides.

In one variation, there is provided the compounds disclosed herein, or a pharmaceutically acceptable salt thereof, optionally in the form of a single stereoisomer or mixture of stereoisomers thereof; and compositions comprising the compounds.

In addition to the exemplary embodiments, aspects and variations described above, further embodiments, aspects and variations will become apparent by reference to the drawings and figures and by examination of the following descriptions.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustratived in the figures and drawings, and it is intended that the embodiments, aspects and variations, and the figures and drawings disclosed herein are to be considered illustrative and not limiting.

"Pharmaceutically acceptable salts" means salt compositions that is generally considered to have the desired pharmacological activity, is considered to be safe, non-toxic and is acceptable for veterinary and human pharmaceutical applications. Such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like.

"Therapeutically effective amount" means an amount of a compound or drug that elicits any of the biological effects listed in the specification.

EXPERIMENTAL

Figure 1:
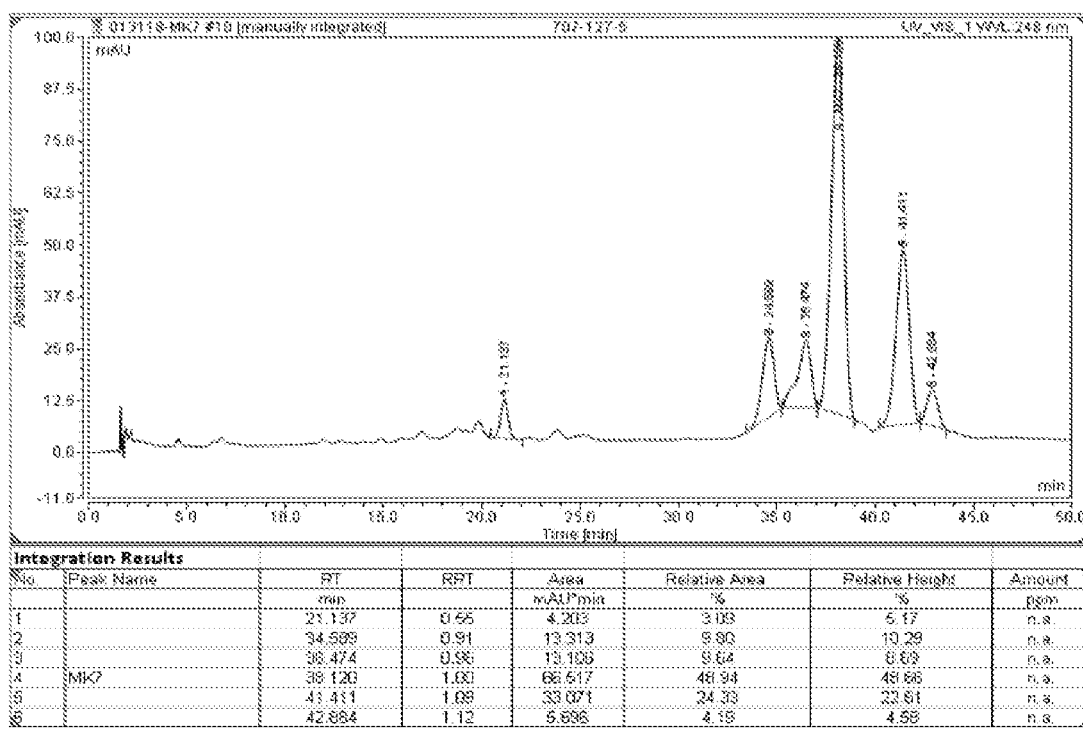
FIG. 1 is a representation of a chromatogram of menaquinone-7 and its regioisomer shown with a ratio of 3:1, as determined by $^1$H NMR.
Figure 2:
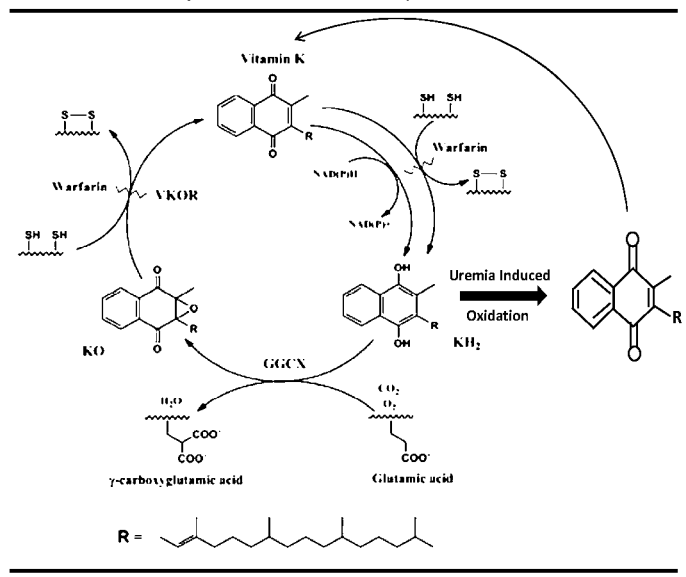
FIG. 2 is a scheme showing the uremia and dialysis induced oxidation of KH2 functional carboxylation of vitamin K dependent proteins.
Figure 3:
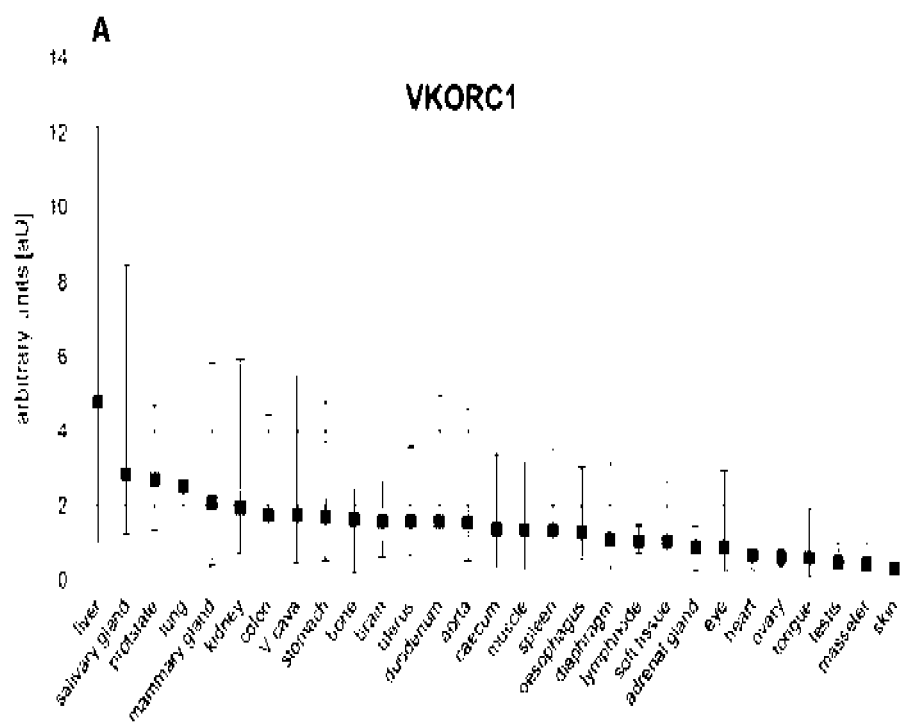
FIG. 3 is graph showing the VKORC1 in arbitrary units and specific tissues.
Figure 4:
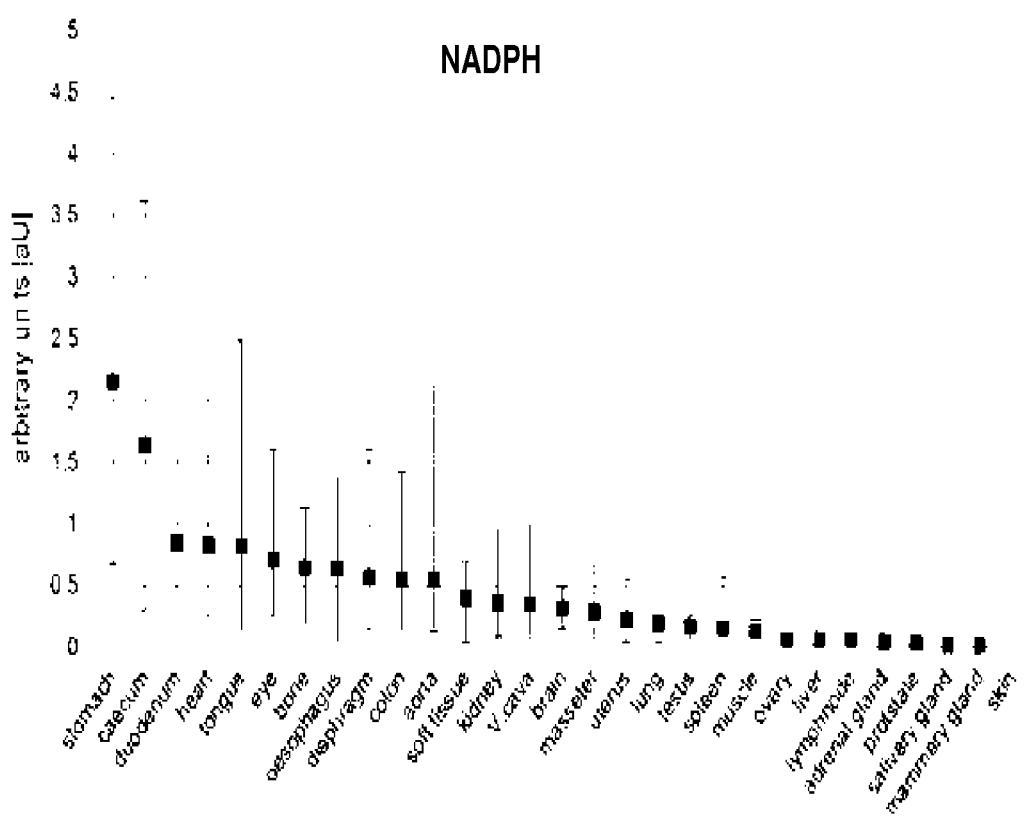
FIG. 4 is a graph showing the NADPH in arbitrary units and specific tissues.
Figure 5:
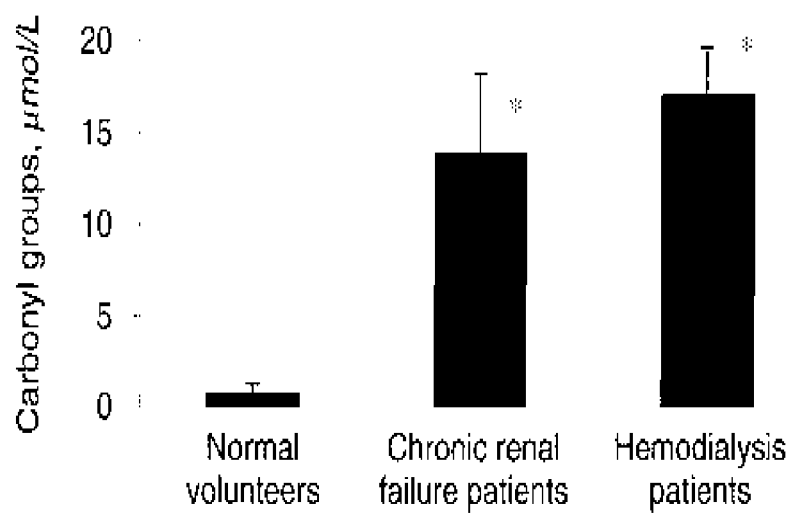
FIG. 5 is a graph showing CKD and ESRD patients exhibit a higher percentage of carbonyl proteins compared to normal controls.

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

Preparation of Menaquinol Derivatives:

Sodium salt of Menaquinol-7: 4.0 g (6.16 mmol) of MK-7 and 60 ml of ethanol is added into a 250 ml 3-N RBF equipped with a magnetic stirrer, and the resulting mixture was stirred at 0° C. for 1 hour under nitrogen. Sodium hydroxide (0.246 g, 1.0 mole equiv) dissolved in water (15 ml) was added dropwise (or slowly titrated in) to the solution over a period of 15 minutes. The resulting mixture was stirred at 0° C. for another hour and slowly warmed to RT. The solvent was removed by rotoevaporation at 35° C. under reduced pressure to afford the isolated menaquinol compound I, where M=$Na^+$ (x is 0), Y is 1, D is – and Z is 0, as an off-white powder.

Sodium salt of Menaquinol-7: 4.0 g (6.16 mmol) of MK-7 and 60 ml of ethanol is added into a 250 ml 3-N RBF equipped with a magnetic stirrer, and the resulting mixture was stirred at 0° C. for 1 hour under nitrogen. Sodium hydroxide (0.495 g, 2.01 mole equiv) dissolved in water (15 ml) was added dropwise (or slowly titrated in) to the solution over a period of 15 minutes. The resulting mixture was stirred at 0° C. for another hour and slowly warmed to RT. The solvent was removed by rotoevaporation at 35° C. under reduced pressure to afford the isolated menaquinol compound I, where M=$Na^+$ (x is 0), Y is 1, D and E are both – and Z is 0, as an off-white powder.

Potassium salt of Menaquinol-7: 4.0 g (6.16 mmol) of MK-7 and 60 ml of ethanol is added into a 250 ml 3-N RBF equipped with a magnetic stirrer, and the resulting mixture was stirred at 0° C. for 1 hour under nitrogen. Potassium hydroxide (0.346 g, 1.0 mole equiv) dissolved in water (15 ml) was added dropwise (or slowly titrated in) to the solution over a period of 15 minutes. The resulting mixture was stirred at 0° C. for another hour and slowly warmed to RT. The solvent was removed by rotoevaporation at 35° C. under reduced pressure to afford the isolated menaquinol compound I, where M=$K^+$ (x is 0), Y is 1, D is – and Z is 0, as an off-white powder.

Calcium salt of Menaquinol-7: 4.0 g (6.16 mmol) of MK-7 and 60 ml of ethanol is added into a 250 ml 3-N RBF equipped with a magnetic stirrer, and the resulting mixture was stirred at 0° C. for 1 hour under nitrogen. Calcium hydroxide (0.228 g, 0.5 mole equiv) dissolved in water (15 ml) was added dropwise (or titrated in) to the solution over a period of 15 minutes. The resulting mixture was stirred at 0° C. for another hour and slowly warmed to RT. The solvent was removed by rotoevaporation at 35° C. under reduced pressure to afford the isolated menaquinol compound I, where M=$Ca^{+2}$ (x is 1), Y is 2, D is – and Z is 0, as an off-white powder.

Calcium salt of Menaquinol-7: 4.0 g (6.16 mmol) of MK-7 and 60 ml of ethanol is added into a 250 ml 3-N RBF equipped with a magnetic stirrer, and the resulting mixture was stirred at 0° C. for 1 hour under nitrogen. Calcium hydroxide (0.456 g, 1.0 mole equiv) dissolved in water (15 ml) was added dropwise (or titrated in) to the solution over a period of 15 minutes. The resulting mixture was stirred at 0° C. for another hour and slowly warmed to RT. The solvent was removed by rotoevaporation at 35° C. under reduced pressure to afford the isolated menaquinol compound I, where M=$Ca^{+2}$ (x is 1), Y is 1, D and E are both – and Z is 1, as an off-white powder.

The menaquinol derivatives, such as the menaquinol-7 derivatives may be prepared according to the general methods as described below. Such acylated linked compounds may be symmetrical, wherein both hydroxyl groups of the menaquinol are acylated and linked to another menaquinol molecule, or only one of the two hydroxyl groups, either the 5-position or the 8-position, are acylated and linked to another menaquinol molecule, and the other remaining as the free hydroxyl group of the menaquinol.

Accordingly, the menaquinone, such as MK-7, may be contacted with a metal, such as zinc, in an acid, such as acetic acid or dilute HCl, for a sufficient time under conditions to form the corresponding menaquinol intermediate. The menaquinol may be isolated before taking the acylation reaction, or the menaquinol may be acylated in situ with an (di)acid halide (X=Cl, Br, I) such as succinoyl dichloride, or dibromide, an acid anhydride such as succinic anhydride, maleic anhydride, malonic anhydride, or an acylating agent such as an acid anhydride in a solvent to form, under the acidic conditions, an initial mono-ester acid, followed by the corresponding dimer of the formula II, III or IV. The acylation reactions may also be performed directly upon reduction of MK-7 upon treatment with one or more equivalents of succinoyl halide in a solvent and a base such as $Et_3N$, DMAP and di-isopropylethylamine.

Similarly, the carbonates of the formula IV, V, VI VII or VIII may be prepared from a carbonylation reaction using a dicarbonate such as dimethylcarbonate (or di-alkyl carbonates), 1,1'-carbonyldiimidazole (CDI), disuccinimidyl carbonate (DSC), a phosgene equivalent such as diphosgene (trichloromethyl chloroformate, $CCl_3OC(O)Cl$), triphosgene (hexachloromethyl carbonate, or bis(trichloromethyl) carbonate ($Cl_3COC(O)OCCl_3$) in a solvent to form the corresponding mono- or di-carbonate menaquinol derivative(s).

To a round-bottom flask is added menaquinol-7 (MK-7, 0.15 g, 0.23 mmol, 1 equiv), zinc powder (0.1 g, 1.5 mmol, 6.5 equiv), and acetic acid (0.2 mL) in methanol (1 mL). The reaction is stirred at room temperature. After the reaction is complete, the reaction is concentrated by exposure to high vacuum to remove all volatiles, and then diluted with pyridine (1 mL). To this mixture is then added the acylating agent such as succinic anhydride (0.5 equiv) and the mixture is allowed to stir at rt until the hydroquinone is consumed. The reaction mixture is then diluted with hexanes and filtrated through Celite. The solution is then washed with a 1M HCl aqueous solution (2×20 mL) and then saturated aqueous $Na_2CO_3$ solution. The organic layer is dried over anhydrous $MgSO_4$, filtered and concentrated in vacuo to yield the acylated product. Further purification could be accomplished via recrystallization or column chromatography.

To a round-bottom flask was added MK-7 (0.15 g, 0.23 mmol, 1 equiv), zinc powder (0.1 g, 1.5 mmol, 6.5 equiv) and pyridine (0.8 mL, 9.9 mmol, 43 equiv) in acetic anhydride (3 mL, 138 equiv). The reaction was stirred for 0.5 h at room temperature (at t=0 h, MK-7 is poorly soluble and the mixture is yellow; after completion, the product is well dispersed and the solution is brown). The reaction was diluted with hexanes (40 mL) and filtrated through Celite. The organic layer was washed in succession with a 1M HCl aqueous solution (2×20 mL) and saturated $Na_2CO_3$ aqueous solution. The organic layer was dried over anhydrous $MgSO_4$, filtered and concentrated in vacuo to yield a pale yellow oil (915 mg, 91%). $R_f$=0.46 (9:1 hexanes/$Et_2O$). $^1H$ NMR and $^{13}C$ NMR (500 MHz, $CDCl_3$) shows that the structure is consistent with the desired product.

Reduction of menaquinone with Pd/C and hydrogen formate: In a two neck round bottom flask fitted with a condenser, a nitrogen purge tube and a magnetic bar is added 10 mL of methanol and toluene mixture (70:30) and 0.93 g ammonium formate dissolved in 1 mL water. Pd-carbon (10%) 100 mg was added after stirring for 15 min under nitrogen followed by the menaquinone (10 mmol) after about 30 seconds. The mixture is stirred for 4 h at room temperature. The catalyst is removed by filtration through a sintered disk under suction and the filtrate evaporated under reduced pressure to give about 2 g of crude solid product. The residue is extracted with dichloromethane and the extract may be used in the acylation step without further purification or isolation.

Depending on the reaction conditions and stoichiometry of the acylating reagent relative to the menaquinol, the formation of the di-acylated product, such as II, III or IV, may be prepared selectively.

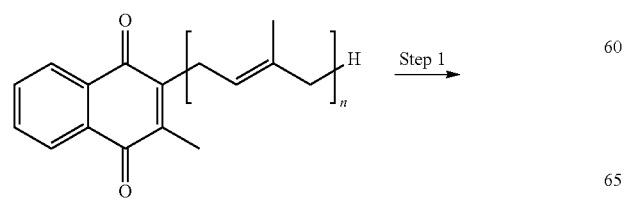

Step 1

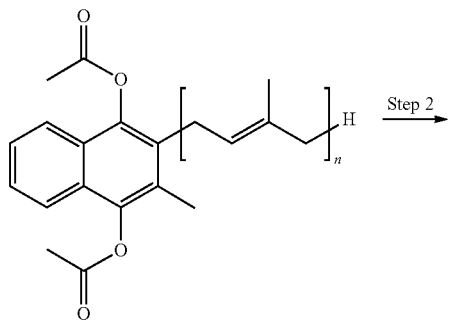

IXa

Step 2

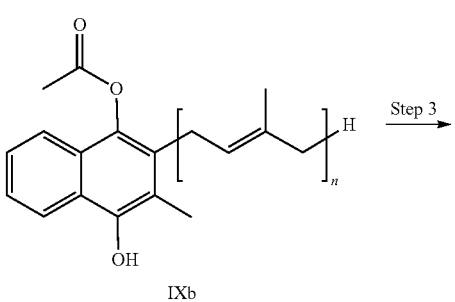

IXb

Step 3

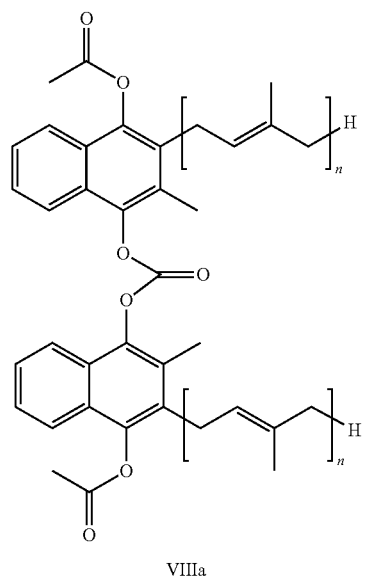

VIIIa

Preparation of Carbonate Dimer VIIIa:

Step-I: Preparation of acetic acid 4-acetoxy-3-((2E,6E,10E,14E,18E,22E)-3,7,11,15,19,23,27-heptamethyl-octacosa-2,6,10,14,18,22,26-heptaenyl)-2-methyl-naphthalen-1-yl ester IXa, where n=7, from 2-((2E,6E,10E,14E,18E,22E)-3,7,11,15,19,23,27-heptamethyl-octacosa-2,6,10,14,18,22,26-heptaenyl)-3-methyl-[1,4]naphthoquinone (MK-7), where n=7

Step-2: Preparation of Acetic acid 2-((2E,6E,10E,14E,18E,22E)-3,7,11,15,19,23,27-heptamethyl-octacosa-2,6,10,14,18,22,26-heptaenyl)-4-hydroxy-3-methyl-naphthalen-1-yl ester IXb (n=7) from acetic acid 4-acetoxy-3-((2E,6E,10E,14E,18E,22E)-3,7,11,15,19,23,27-heptamethyl-octacosa-2,6,10,14,18,22,26-heptaenyl)-2-methyl-naphthalen-1-yl ester IXa (n=7)

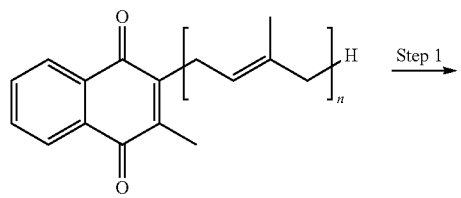

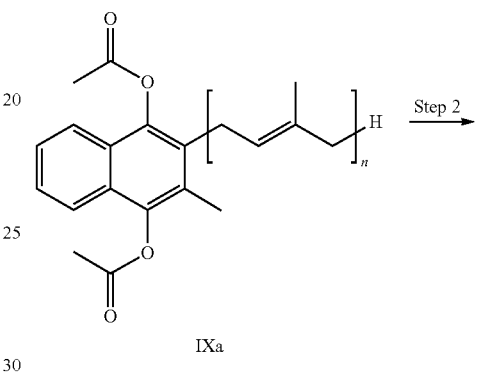

IXa

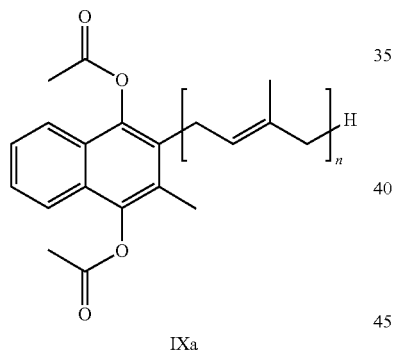

IXa

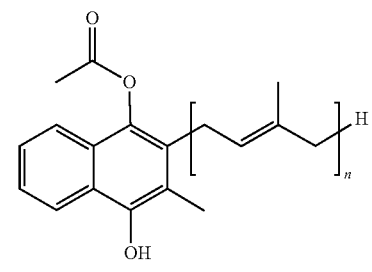

IXb

Figure 6:
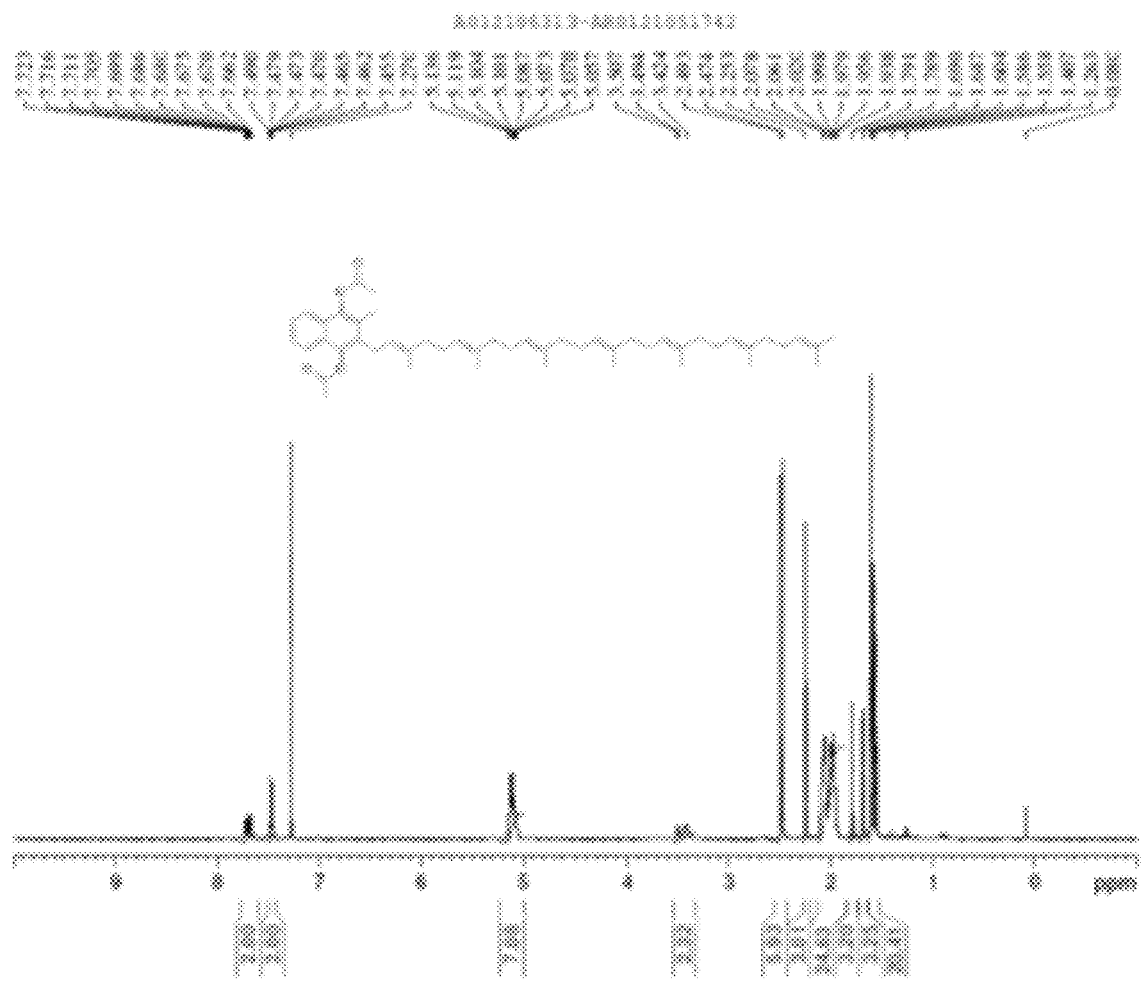
FIG. 6 shows that the H1 nmr obtained was consistent with the product.

To a stirring solution of MK-7 (5.0 g, 7.7 mmol) in pyridine (10 mL, 2V) were added acetic anhydride (75 mL, 15V) and Zn dust (3.2 g, 50 mmol) at room temperature (25-30° C.). The reaction mixture was stirred at RT for 2 h. The reaction completion was monitored by TLC (15% ethyl acetate/hexane). The reaction mixture was filtered through celite and washed with ethyl acetate (10 mL), filtrate was diluted with ethyl acetate (250 mL) and washed with water (2×100 mL), separated organic layer was concentrated and crude obtained was purified by column chromatography (3-4% ethyl acetate/hexane) to yield the compound IXa as a pale yellow liquid (4.2 g, 75%). The $H^1$ nmr obtained was consistent with the product, as shown in FIG. 6.

Figure 7:
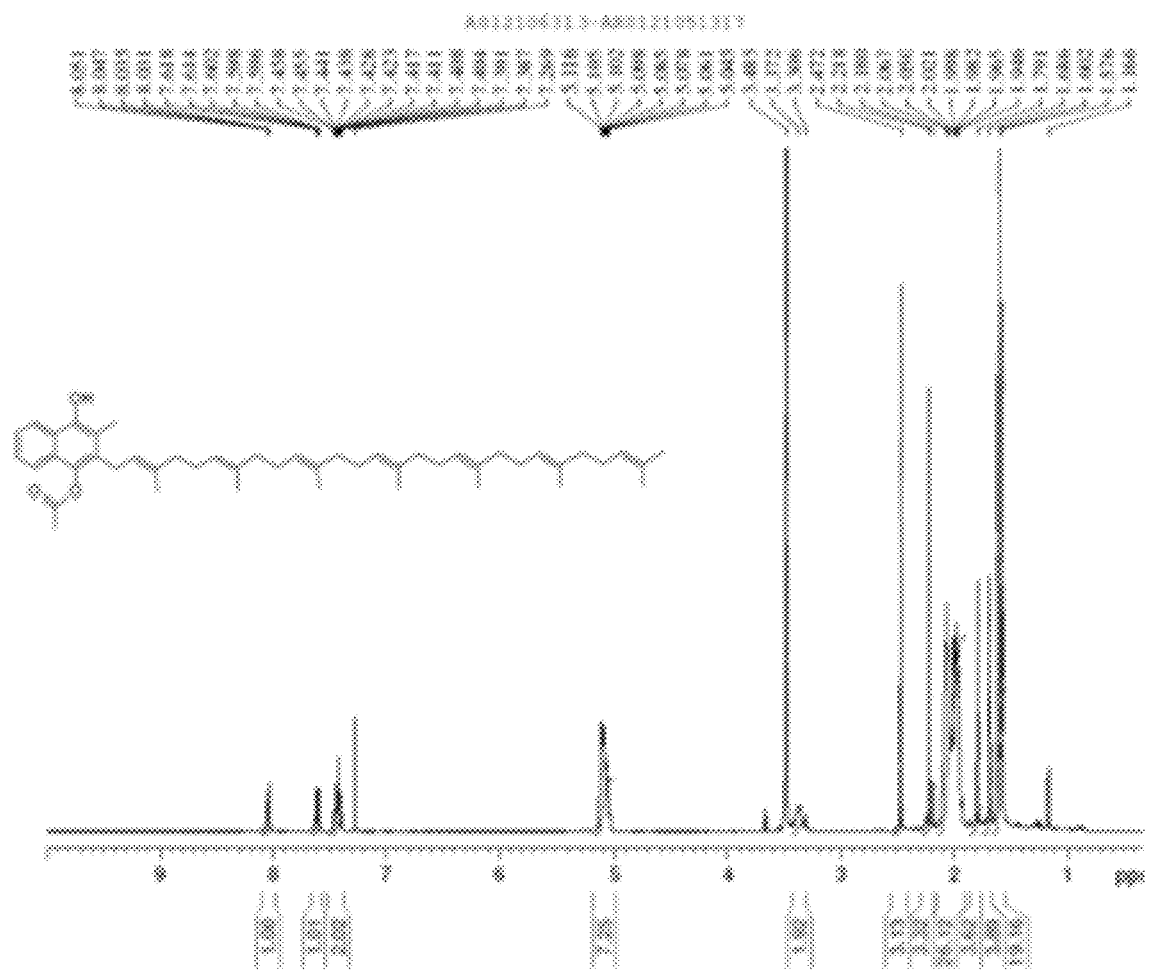
FIG. 7 shows that the H1 nmr obtained was consistent with the product.

To a stirring solution of compound IXa (2.2 g, 3.0 mmol) in methanol (22 mL, 10V) and MTBE (11 mL, 5V) was added tert-butylamine (1.29 mL, 12 mmol) at room temperature (25-30° C.) and stirred for 12-16 at same temperature. The reaction completion was monitored by TLC (10% ethyl acetate/hexane). The reaction mixture was concentrated (to remove methanol), diluted with ethyl acetate (200 mL) and washed with water (2×100 mL). The organic layer was separated and washed with brine solution (50 mL) then dried over sodium sulfate and concentrated. Crude product obtained was purified by column chromatography (3-4% ethyl acetate/hexane) to yield compound IXb, n=7, as a pale brown thick liquid (0.45 g, 22%). The $H^1$ nmr obtained was consistent with the product, as shown in FIG. 7.

Step-3: Preparation of 4-[({[4-(acetyloxy)-3-[(2E,6E,10E,14E,18E,22E)-3,7,11,15,19,23,27-heptamethyloctacosa-2,6,10,14,18,22,26-heptaen-1-yl]-2-methylnaphthalen-1-yl]oxy}carbonyl)oxy]-2-[(2E,6E,10E,14E,18E,22E)-3,7,11,15,19,23,27-heptamethyloctacosa-2,6,10,14,18,22,26-heptaen-1-yl]-3-methylnaphthalen-1-yl acetate, VIIIa (n=7), from acetic acid 2-((2E,6E,10E,14E,18E,22E)-3,7,11,15,19,23,27-heptamethyl-octacosa-2,6,10,14,18,22,26-heptaenyl)-4-hydroxy-3-methyl-naphthalen-1-yl ester IXb (n=7)

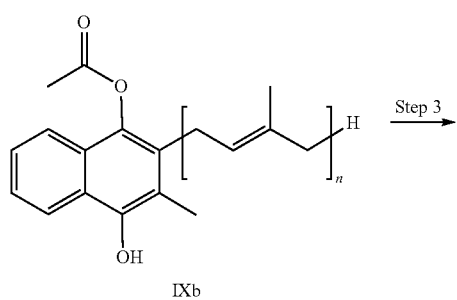

IXb

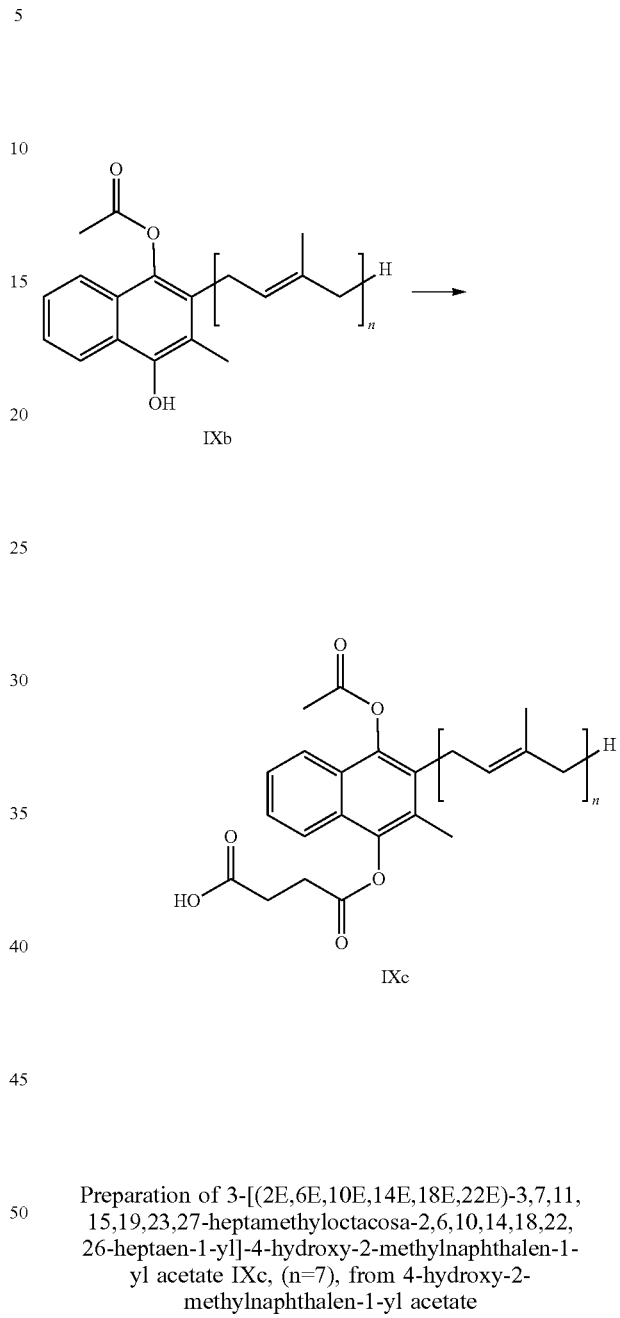

Figure 8:
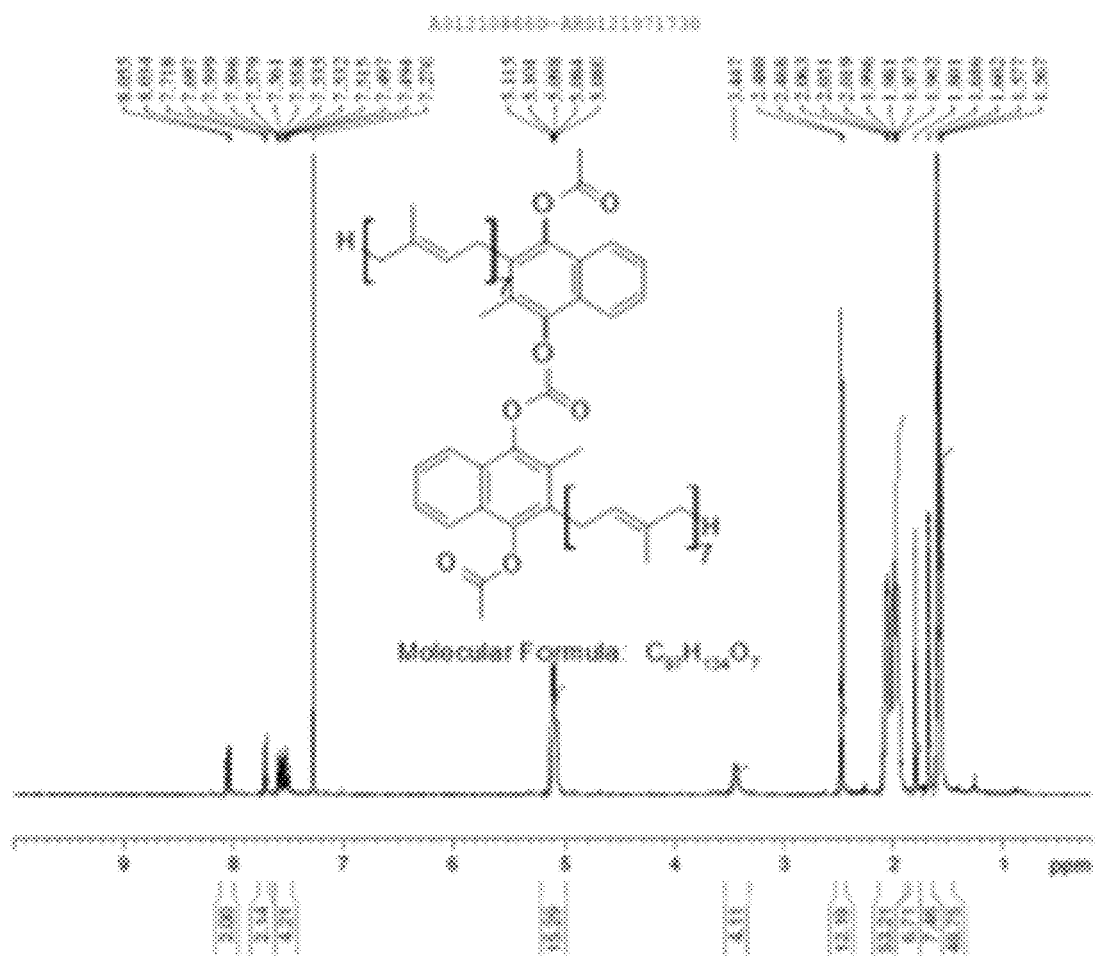
FIG. 8 shows that the H1 nmr obtained was consistent with the product.

To a stirring solution of compound IXb (1.0 g, 14.4 mol) in DCM (10 mL, 10 V) was added TEA (0.4 mL, 28.8 mmol) and phosgene (0.42 mL, 8.6 mmol, 0.6 eq.) at room temperature and stirred for 30 min. The reaction completion was monitored by TLC (15% ethyl acetate/hexane). The reaction mixture was diluted with ethyl acetate (200 mL) and washed with water (2×100 mL). The organic layer was separated and washed with brine solution (50 mL) then dried over sodium sulfate and concentrated. Crude product obtained was purified by column chromatography (10% ethyl acetate/hexane) to yield MK-7-carbonate dimer VIIIa (n=7), as a waxy solid (0.36 g, 40%). The H$^1$ nmr obtained was consistent with the product, as shown in FIG. 8.

Preparation of Carbonate VIIIb

Preparation of 3-[(2E,6E,10E,14E,18E,22E)-3,7,11,15,19,23,27-heptamethyloctacosa-2,6,10,14,18,22,26-heptaen-1-yl]-4-hydroxy-2-methylnaphthalen-1-yl acetate IXc, (n=7), from 4-hydroxy-2-methylnaphthalen-1-yl acetate

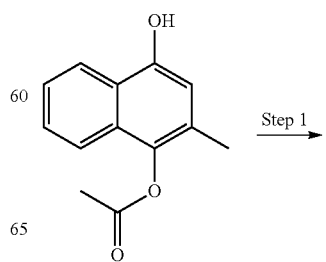

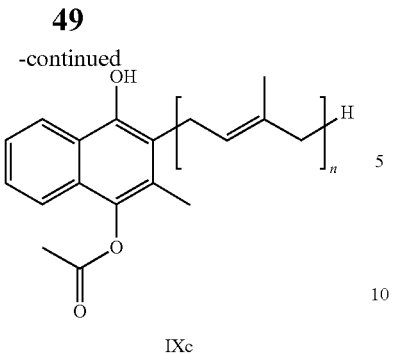

IXc

The overall process provides chemo- or regioselective alkylation of the prenoidal side chain (n=7, 8 or 10) to the desired position in >99% selectivity and provides a single isomer. The mono-acetate in step 1, 4-hydroxy-2-methyl-naphthalen-1-yl acetate, may be prepared by the reduction and subsequent di-acylation of 2-methyl-1,4-naphthoquinone using Pd/C, acetic anhydride, ethyl acetate and DMAP to form the diacylated quinol, which is then selectively de-acylated in methanol and ter-butylamine to provide the desired product, 4-hydroxy-2-methylnaphthalen-1-yl acetate.

To a stirring solution of 4-hydroxy-2-methylnaphthalen-1-yl acetate (10.0 g, 46.3 mmol) in toluene (100 mL, 10V) were added heptaprenol (16.0 g, 37.0 mmol, 0.8 eq.) and benzene sulfonic acid (0.64 g, 4.63 mmol) at room temperature (25-30° C.). The reaction mixture was stirred at RT for 16-24 h. The reaction completion was monitored by TLC (15% ethyl acetate/hexane). The reaction mixture was diluted with ethyl acetate (500 mL) and washed with water (2×250 mL). The organic layer was separated and washed with brine solution (200 mL) then dried over sodium sulfate and concentrated. Crude product obtained was purified by column chromatography (2-3% ethyl acetate/hexane) and crystallized from ethanol to yield IXc (n=7) as an off white solid (4.0 g, 13%).

Figure 9:
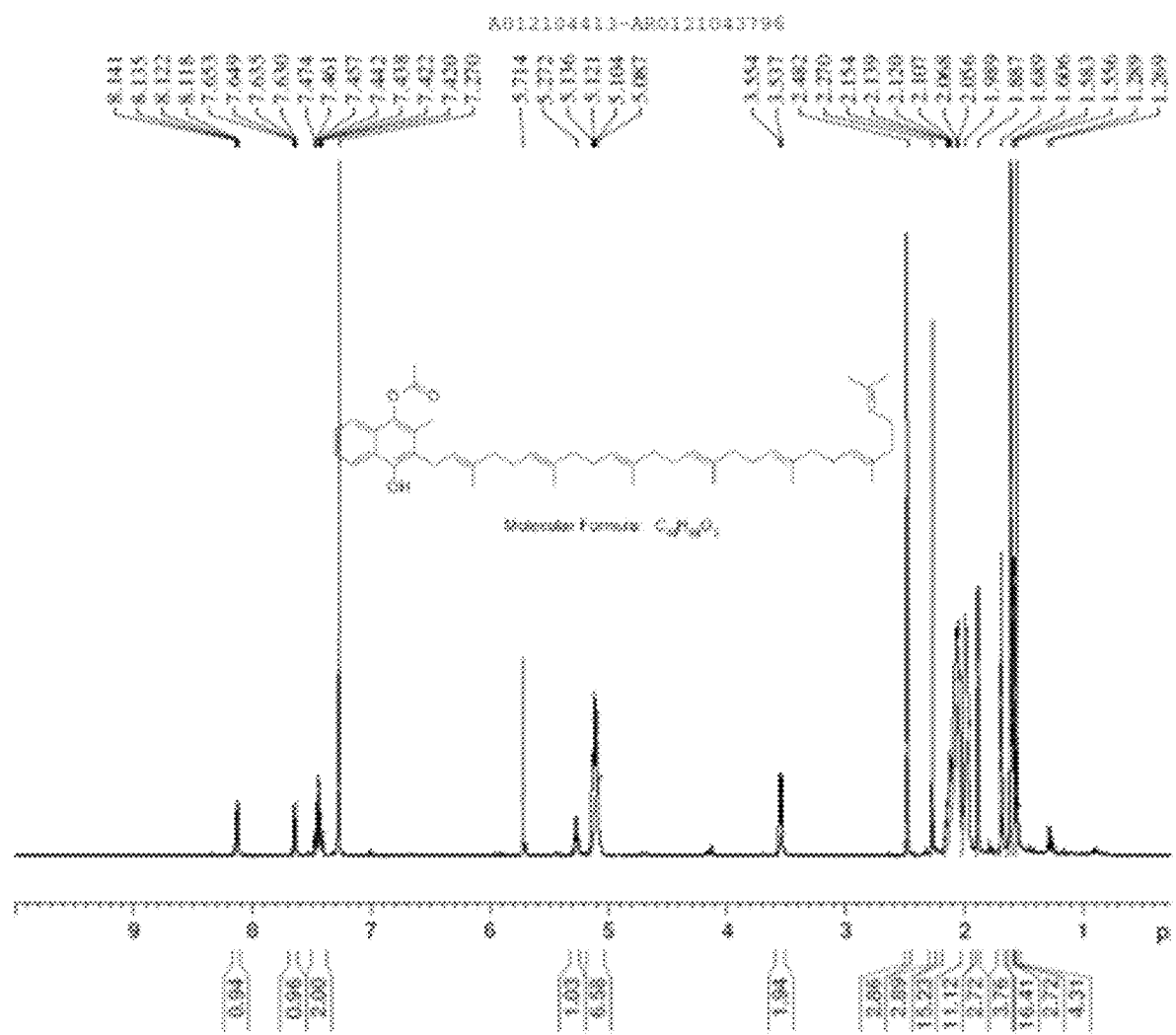
FIG. 9 shows that the crude product obtained was purified by column chromatography (2-3% ethyl acetate/hexane) and crystallized from ethanol to yield IXc (n=7) as an off white solid (4.0 g, 13%).

Step-1-H-NMR, as shown in FIG. 9

Step-2: Preparation of 4-[({[4-(acetyloxy)-2-[(2E, 6E,10E,14E,18E,22E)-3,7,11,15,19,23,27-heptamethyloctacosa-2,6,10,14,18,22,26-heptaen-1-yl]-3-methylnaphthalen-1-yl]oxy}carbon yl)oxy]-3-[(2E, 6E,10E,14E,18E,22E,26E)-2,6,10,14,18,22,26-heptamethyloctacosa-2,6,10,14,18,22,26-heptaen-1-yl]-2-methylnaphthalen-1-yl acetate from 3-[(2E,6E, 10E,14E,18E,22E)-3,7,11,15,19,23,27-heptamethyloctacosa-2,6,10,14,18,22,26-heptaen-1-yl]-4-hydroxy-2-methylnaphthalen-1-yl acetate VIIIb (n=7)

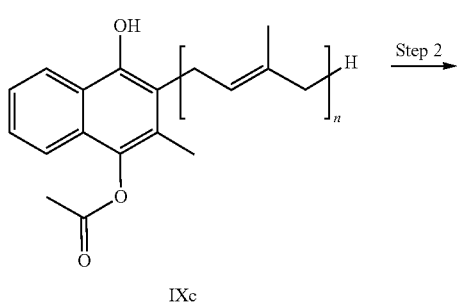

IXc

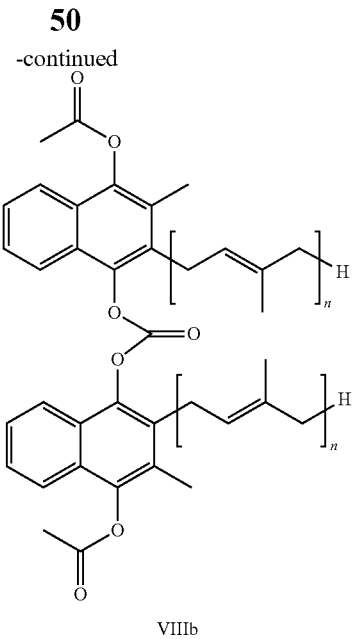

VIIIb

Figure 10:
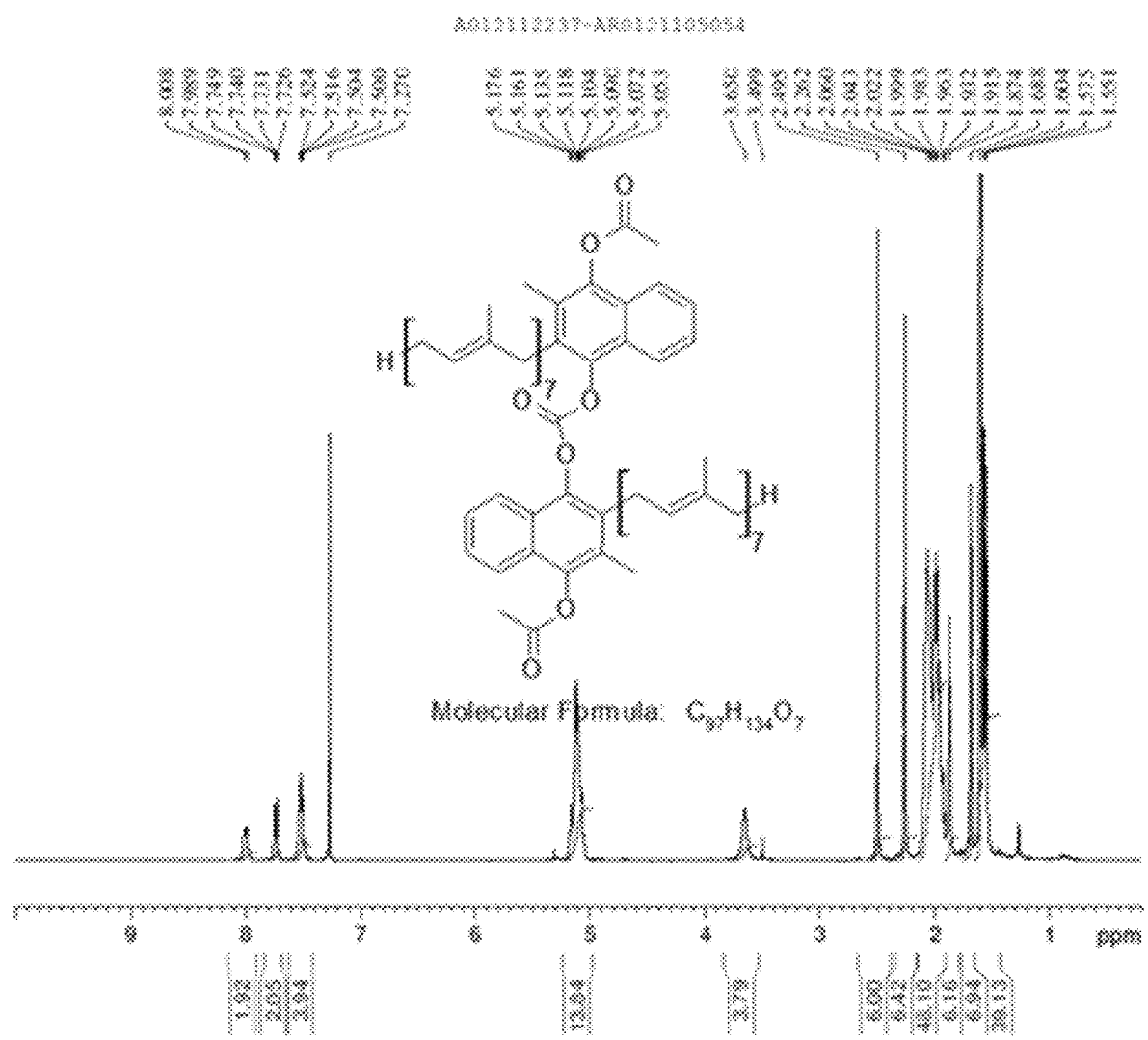
FIG. 10 shows that the crude product obtained was purified by column chromatography (10% ethyl acetate/hexane) to yield MK-7-carbonate-2 dimer VIIIb (n=7), as a sticky solid (0.51 g, 50%).

To a stirring solution of IXc (n=7), (1.0 g, 14.4 mol) in DCM (10 mL, 10 V) was added TEA (0.4 mL, 28.8 mmol) and phosgene (0.42 mL, 8.6 mmol, 0.6 eq.) at room temperature and stirred for 30 min. The reaction completion was monitored by TLC (15% ethyl acetate/hexane). The reaction mixture was diluted with ethyl acetate (200 mL) and washed with water (2×100 mL). The organic layer was separated and washed with brine solution (50 mL) then dried over sodium sulfate and concentrated. Crude product obtained was purified by column chromatography (10% ethyl acetate/hexane) to yield MK-7-carbonate-2 dimer VIIIb (n=7), as a sticky solid (0.51 g, 50%), as shown in FIG. 10.

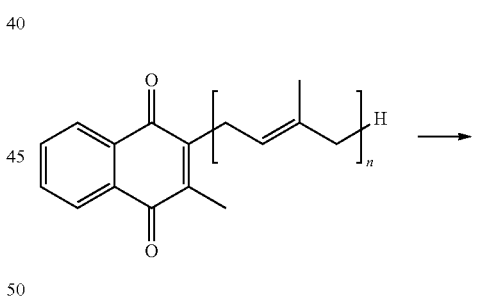

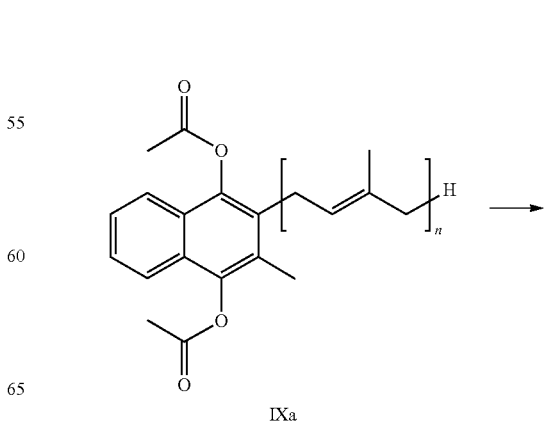

IXa

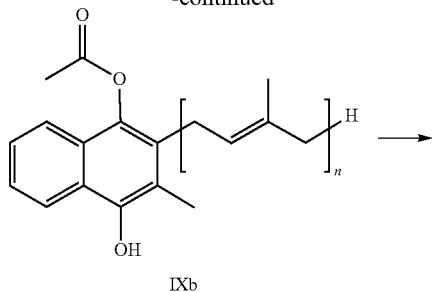

IXb

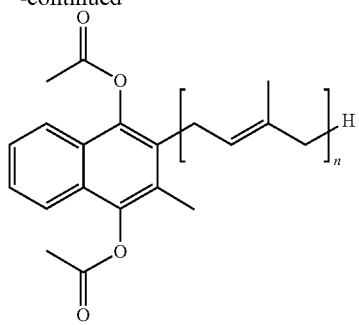

IXa

Step-1: Preparation of acetic acid 4-acetoxy-3-((2E, 6E,10E,14E,18E,22E)-3,7,11,15,19,23,27-heptamethyl-octacosa-2,6,10,14,18,22,26-heptaenyl)-2-methyl-naphthalen-1-yl ester IXa (n=7), from 2-((2E,6E,10E,14E,18E,22E)-3,7,11,15,19,23,27-heptamethyl-octacosa-2,6,10,14,18,22,26-heptaenyl)-3-methyl-[1,4]naphthoquinone (MK-7)

Figure 11A:
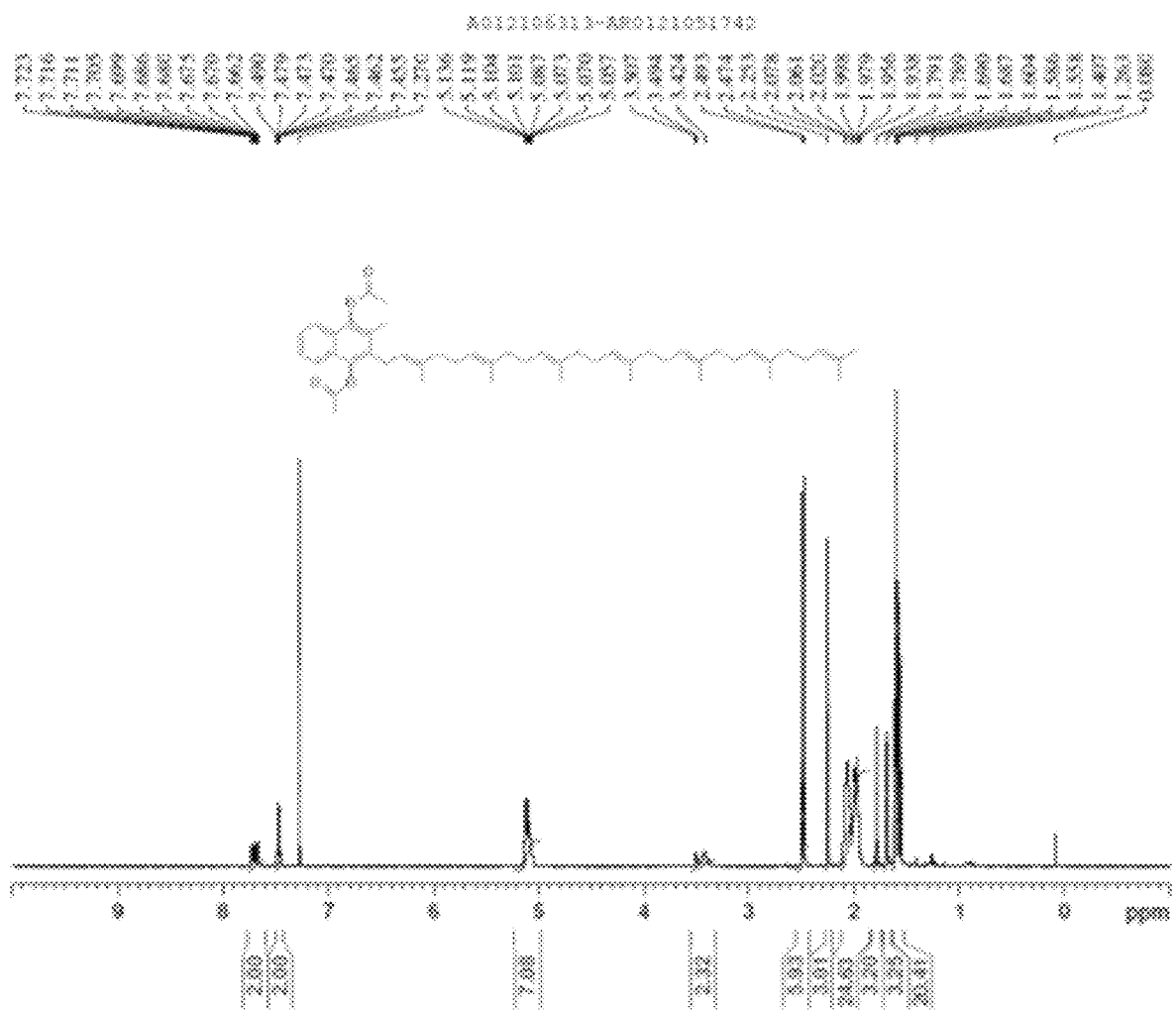
FIGS. 11A and 11B show that the reaction mixture was concentrated and crude obtained was purified by column chromatography (3-4% ethyl acetate/hexane) to yield IXa as a pale yellow liquid (4.2 g, 75%).
Figure 11B:
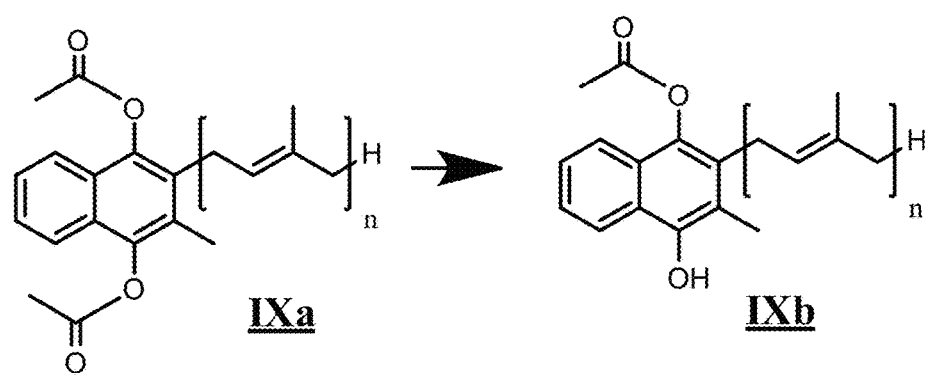

To a stirring solution of MK-7 (5.0 g, 7.7 mmol) in pyridine (10 mL, 2V) were added acetic anhydride (75 mL, 15V) and Zn dust (3.2 g, 50 mmol) at room temperature (25-30° C.). The reaction mixture was stirred at RT for 2 h. The reaction completion was monitored by TLC (15% ethyl acetate/hexane). The reaction mixture was concentrated and crude obtained was purified by column chromatography (3-4% ethyl acetate/hexane) to yield IXa as a pale yellow liquid (4.2 g, 75%), as shown in FIGS. 11A and 11B.

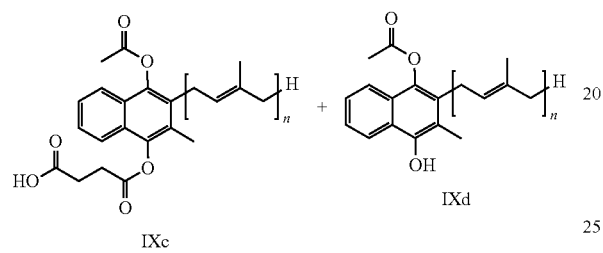

IXc       IXd

↓

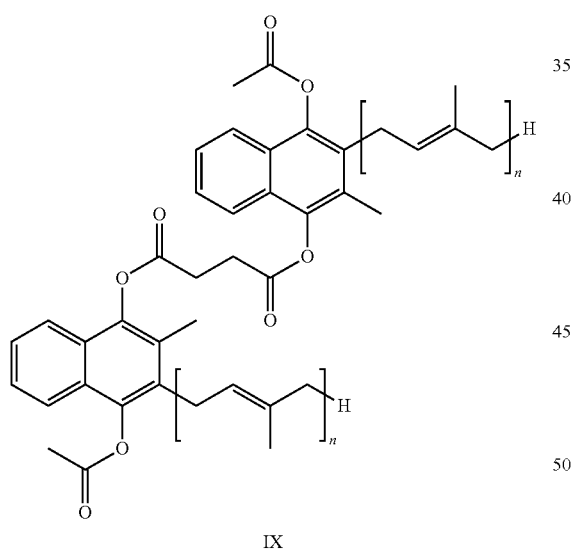

IX

Preparation of Succinate IX (n=7)

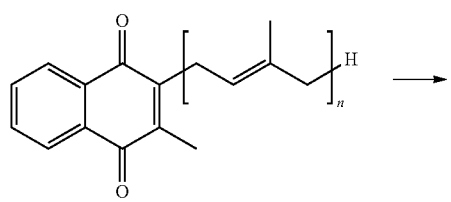

Step 2: Preparation of acetic acid 2-((2E,6E,10E, 14E,18E,22E)-3,7,11,15,19,23,27-heptamethyl-octacosa-2,6,10,14,18,22,26-heptaenyl)-4-hydroxy-3-methyl-naphthalen-1-yl ester IXb, n=7, from acetic acid 4-acetoxy-3-((2E,6E,10E,14E,18E,22E)-3,7,11, 15,19,23,27-heptamethyl-octacosa-2,6,10,14,18,22, 26-heptaenyl)-2-methyl-naphthalen-1-yl ester IXa, (n=7)

Figure 12A:
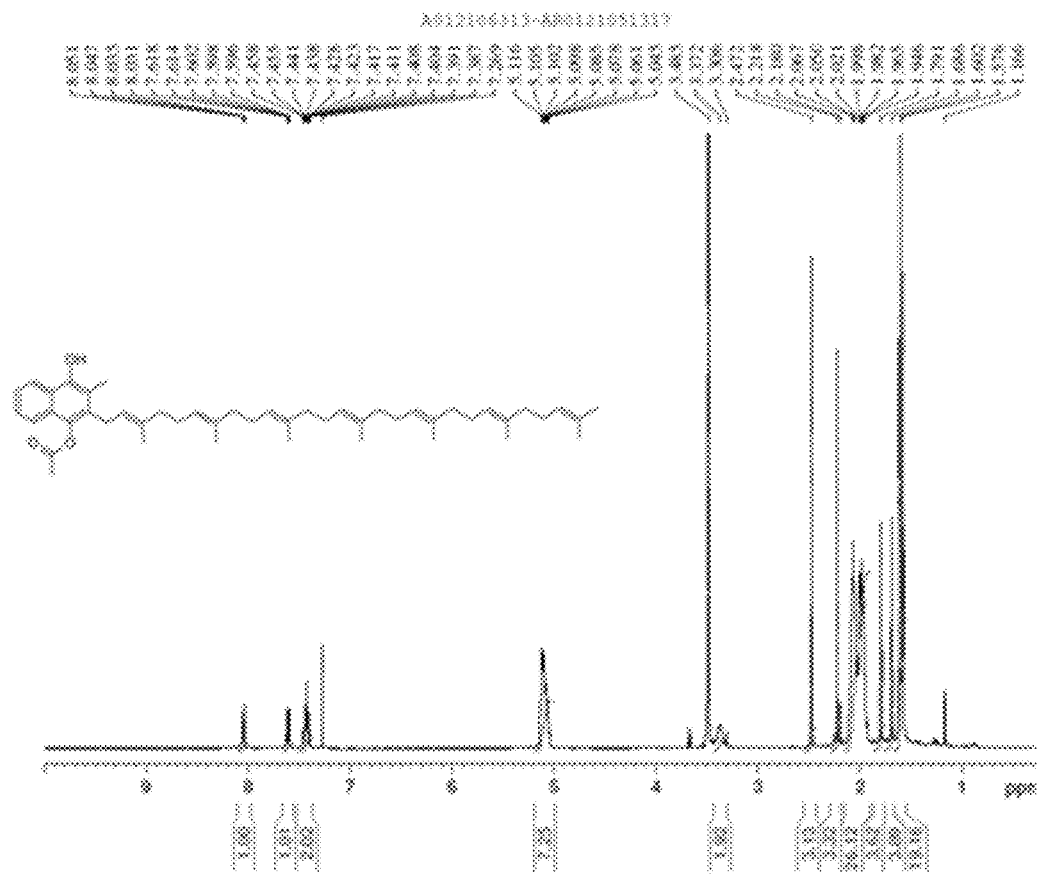
FIGS. 12A and 12B show that the crude product obtained was purified by column chromatography (3-4% ethyl acetate/hexane) to yield IXb as a brown liquid (0.45 g, 22%).
Figure 12B:
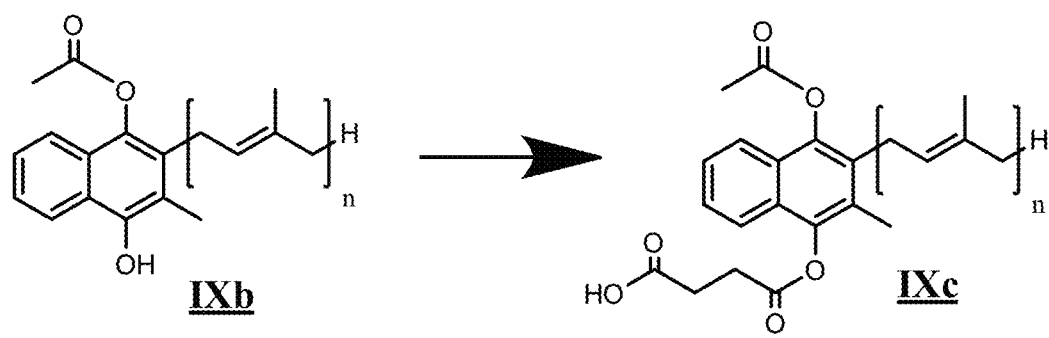

To a stirring solution of IXa (2.2 g, 3.0 mmol) in methanol (22 mL, 10V) and MTBE (11 mL, 5V) was added tert-butylamine (1.29 mL, 12 mmol) at room temperature (25-30° C.) and stirred for 12-16 at same temperature. The reaction completion was monitored by TLC (10% ethyl acetate/hexane). The reaction mixture was concentrated (to remove methanol), diluted with ethyl acetate (200 mL) and washed with water (2×100 mL). The organic layer was separated and washed with brine solution (50 mL) then dried over sodium sulfate and concentrated. Crude product obtained was purified by column chromatography (3-4% ethyl acetate/hexane) to yield IXb as a brown liquid (0.45 g, 22%), as shown in FIGS. 12A and 12B.

Step 3: Preparation of 4-{[4-(acetyloxy)-3-[(2E,6E, 10E,14E,18E,22E)-3,7,11,15,19,23,27-heptamethyl-octacosa-2,6,10,14,18,22,26-heptaen-1-yl]-2-methyl-naphthalen-1-yl]oxy}-4-oxobutanoic acid IXc (n=7) from acetic acid 2-((2E,6E,10E,14E,18E,22E)-3,7, 11,15,19,23,27-heptamethyl-octacosa-2,6,10,14,18, 22,26-heptaenyl)-4-hydroxy-3-methyl-naphthalen-1-yl ester I (n=7)

Figure 13A:
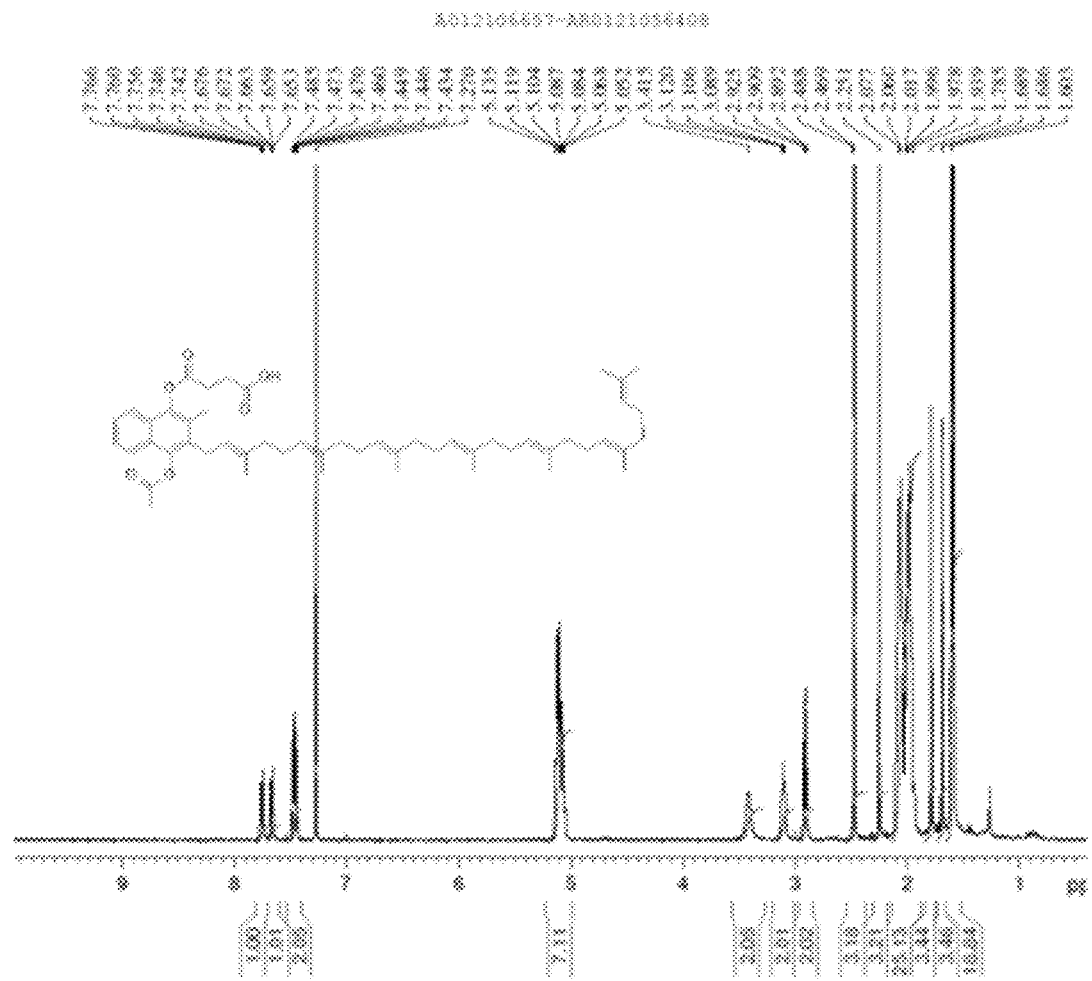
FIGS. 13A and 13B show that the crude product obtained was purified by column chromatography (40% ethyl acetate/hexane) to yield IXc as an off white low melting solid (0.2 g, 70%).
Figure 13B:
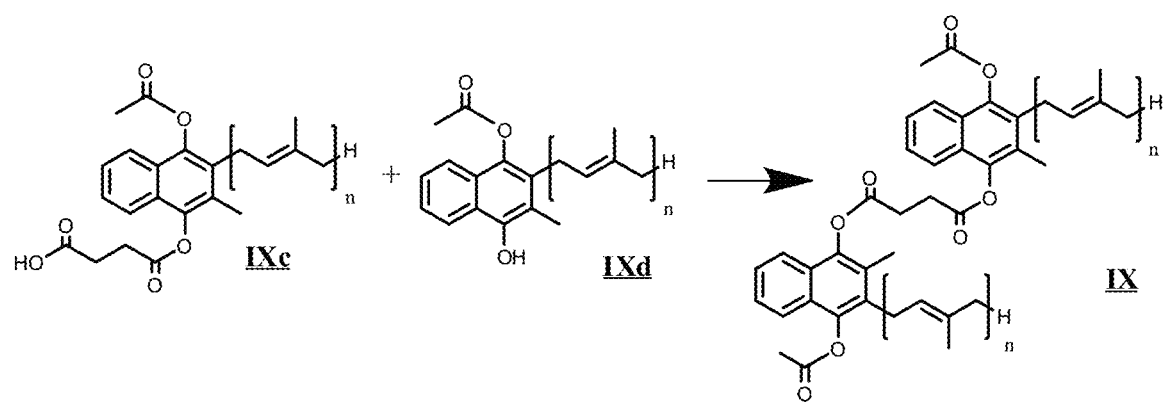

To a stirring solution of IXb (0.25 g, 0.36 mmol) in DCM (2.5 mL, 10V) were added succinic anhydride (0.054 g, 0.54 mmol) and DMAP (0.023 g, 0.18 mmol) at 25-30° C. and stirred for 1-2 at same temperature. The reaction completion was monitored by TLC (80% ethyl acetate/hexane). The reaction mixture was diluted with DCM (100 mL) and washed with water (2×50 mL). The organic layer was separated and washed with brine solution (30 mL) then dried over sodium sulfate and concentrated. Crude product obtained was purified by column chromatography (40% ethyl acetate/hexane) to yield IXc as an off white low melting solid (0.2 g, 70%), as shown in FIGS. 13A and 13B.

Step 4: Preparation of bis[4-(acetyloxy)-3-[(2E,6E, 10E,14E,18E,22E)-3,7,11,15,19,23,27-heptamethyl-octacosa-2,6,10,14,18,22,26-heptaen-1-yl]-2-methyl-naphthalen-1-yl] butanedioate IX (n=7), from 4-{[4-(acetyloxy)-3-[(2E,6E,10E,14E,18E,22E)-3,7,11, 15,19,23,27-heptamethyloctacosa-2,6,10,14,18,22, 26-heptaen-1-yl]-2-methylnaphthalen-1-yl]oxy}-4-oxobutanoic acid IXc, n=7

Figure 14:
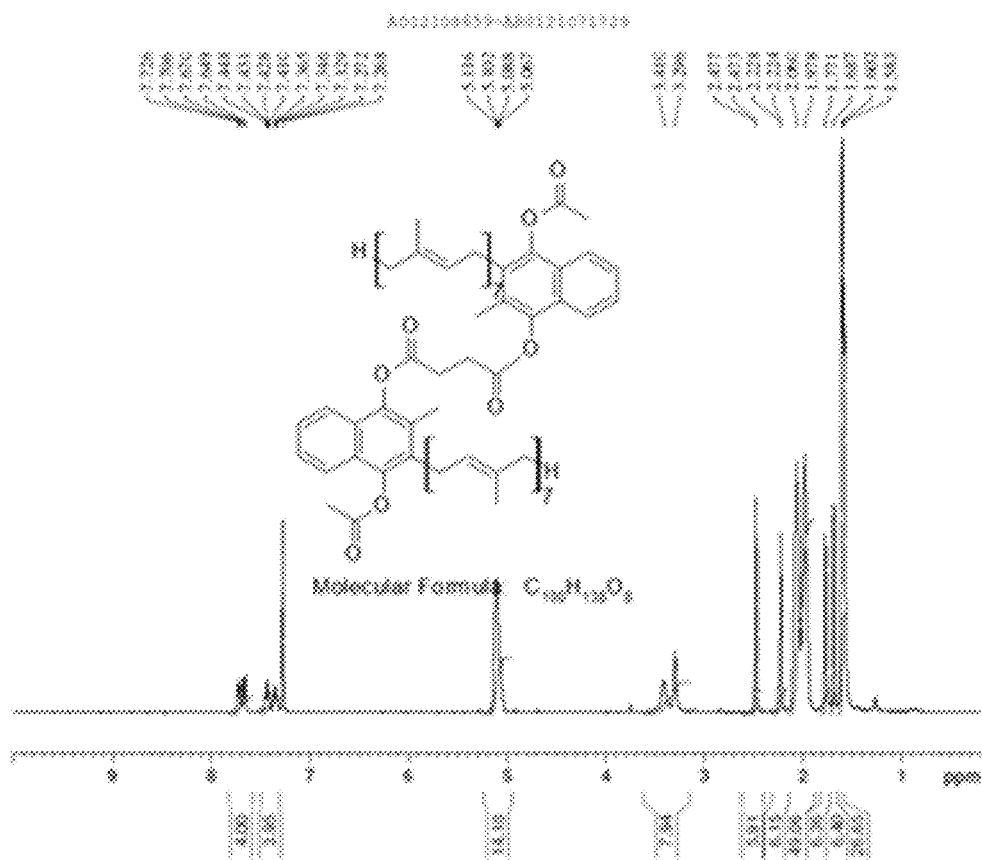
FIG. 14 shows that the crude product obtained was purified by column chromatography (10% ethyl acetate/hexane) to yield MK-7-succinate-1 dimer IX (n=7), as an off white sticky solid (0.44 g, 38%).

To a stirring solution of IXc (n=7), (0.62 g, 0.78 mmol) in DCM (6.2 mL, 10V) was added EDCI (0.176 g, 1.17 mmol) and DMAP (0.09 g, 0.78 mmol) at 0-5° C. and stirred for 10 min at same temperature. To the above reaction mixture IXd (n=7), (0.52 g, 0.78 mmol) in DCM (4.0 mL) was added at 0-5° C. and stirred for 1-2 at 25-30° C. Reaction completion was monitored by TLC (15% ethyl acetate/hexane). The reaction mixture was diluted with ethyl acetate (200 mL) and washed with water (2×100 mL). The organic layer was separated and washed with brine solution (50 mL) then dried over sodium sulfate and concentrated. Crude product obtained was purified by column chromatography (10% ethyl acetate/hexane) to yield MK-7-succinate-1 dimer IX (n=7), as an off white sticky solid (0.44 g, 38%), shown in FIG. 14.

Preparation of MK-7 Succinate Dimer X

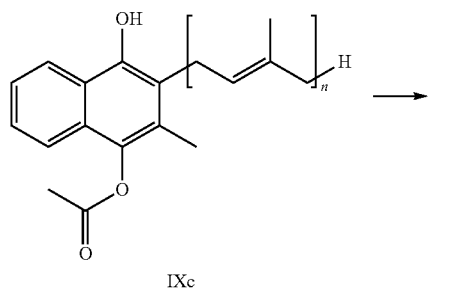

IXc

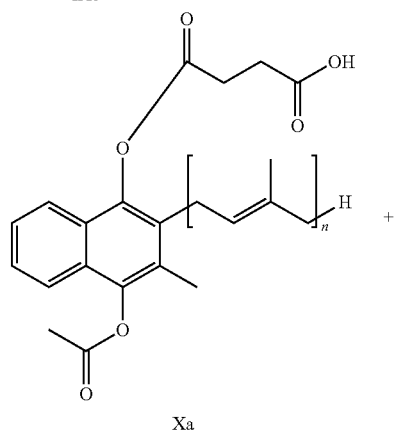

Xa

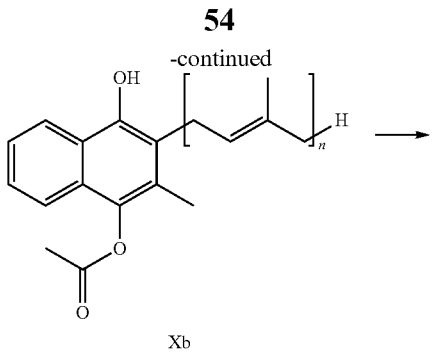

Xb

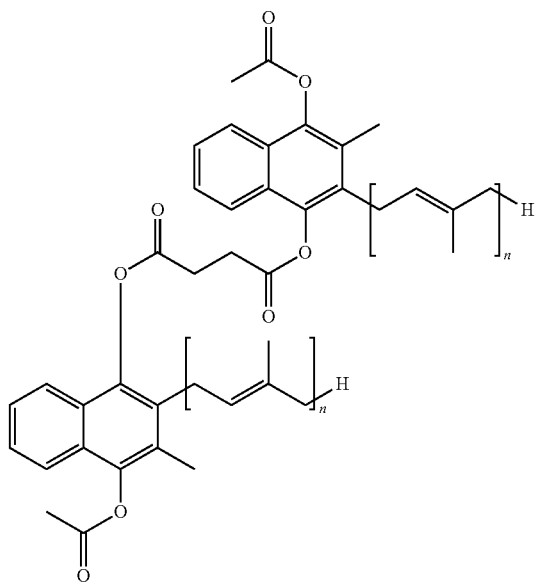

X

NOTE: For the above process, step 1 is in common with the preparation of the carbonate, as described above.

Step 1: Preparation of 3-[(2E,6E,10E,14E,18E, 22E)-3,7,11,15,19,23,27-heptamethyloctacosa-2,6, 10,14,18,22,26-heptaen-1-yl]-4-hydroxy-2-methyl-naphthalen-1-yl acetate IXc, (n=7), from 4-hydroxy-2-methylnaphthalen-1-yl acetate

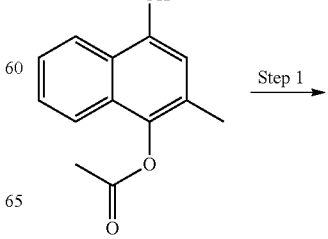

-continued

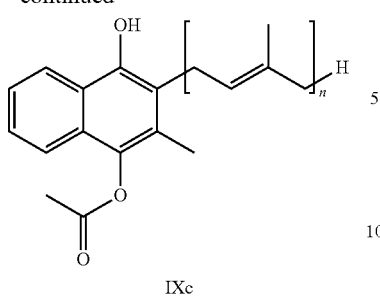

IXc

To a stirring solution of 4-hydroxy-2-methylnaphthalen-1-yl acetate (10.0 g, 46.3 mmol) in toluene (100 mL, 10V) were added heptaprenol (16.0 g, 37.0 mmol, 0.8 eq.) and benzene sulfonic acid (0.64 g, 4.63 mmol) at room temperature (25-30° C.). The reaction mixture was stirred at RT for 16-24 h. The reaction completion was monitored by TLC (15% ethyl acetate/hexane). The reaction mixture was diluted with ethyl acetate (500 mL) and washed with water (2×250 mL). The organic layer was separated and washed with brine solution (200 mL) then dried over sodium sulfate and concentrated. Crude product obtained was purified by column chromatography (2-3% ethyl acetate/hexane) and crystallized from ethanol to yield IXc (n=7) as an off white solid (4.0 g, 13%).

Step 2: Preparation of 4-{[4-(acetyloxy)-2-[(2E,6E,10E,14E,18E,22E)-3,7,11,15,19,23,27-heptamethyl-octacosa-2,6,10,14,18,22,26-heptaen-1-yl]-3-methyl-naphthalen-1-yl]oxy}-4-oxobutanoic acid Xa (n=7), from 3-[(2E,6E,10E,14E,18E,22E)-3,7,11,15,19,23,27-heptamethyloctacosa-2,6,10,14,18,22,26-heptaen-1-yl]-4-hydroxy-2-methylnaphthalen-1-yl acetate IXc (n=7)

Figure 15:
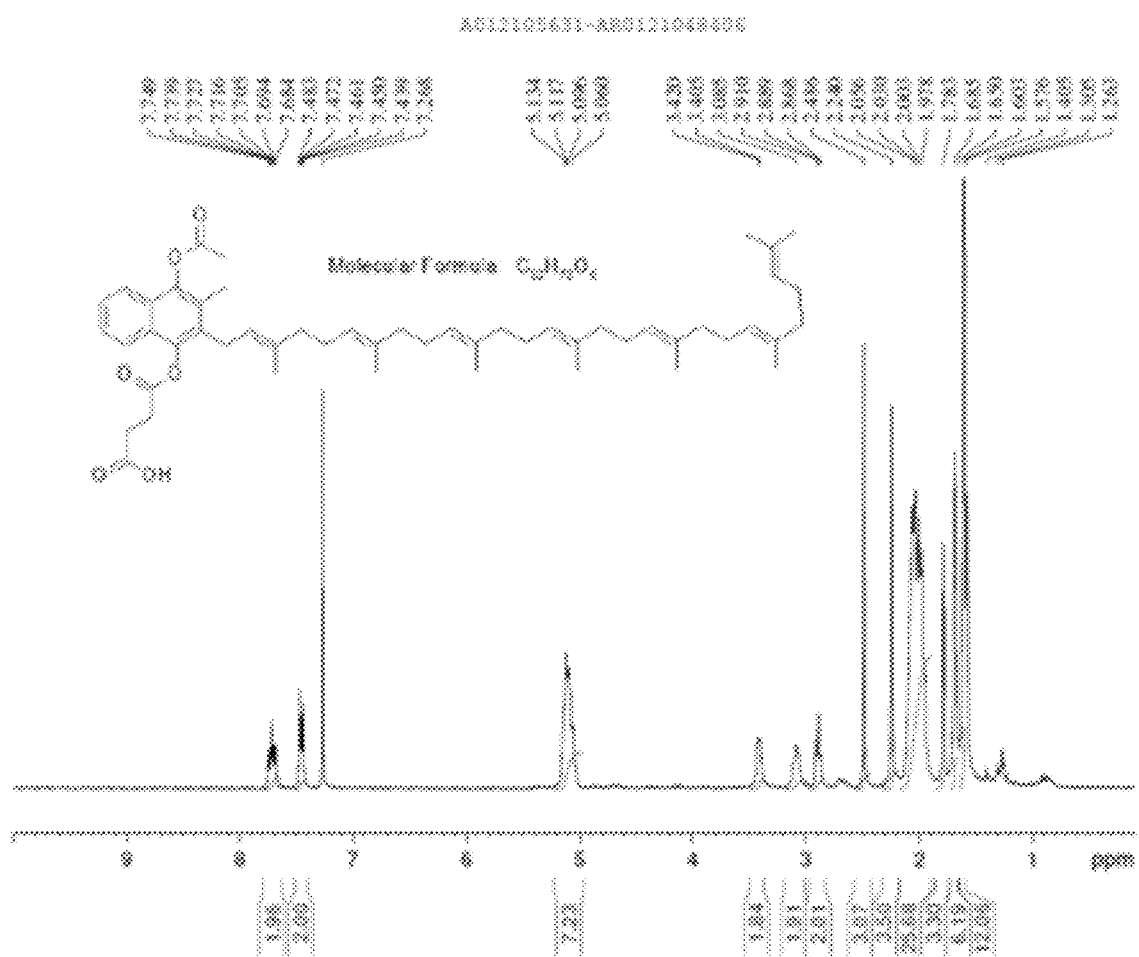
FIG. 15 shows that the crude product obtained was purified by column chromatography (40% ethyl acetate/hexane) to yield Xa as an off white low melting solid (0.2 g, 70%).

To a stirring solution of IXc (0.25 g, 0.36 mmol) in DCM (2.5 mL, 10V) were added succinic anhydride (0.054 g, 0.54 mmol) and DMAP (0.023 g, 0.18 mmol) at 25-30° C. and stirred for 1-2 at same temperature. The reaction completion was monitored by TLC (80% ethyl acetate/hexane). The reaction mixture was diluted with DCM (100 mL) and washed with water (2×50 mL). The organic layer was separated and washed with brine solution (30 mL) then dried over sodium sulfate and concentrated. Crude product obtained was purified by column chromatography (40% ethyl acetate/hexane) to yield Xa as an off white low melting solid (0.2 g, 70%), as shown in FIG. 15.

Step 3: Preparation of bis[4-(acetyloxy)-2-[(2E,6E,10E,14E,18E,22E)-3,7,11,15,19,23,27-heptamethyl-octacosa-2,6,10,14,18,22,26-heptaen-1-yl]-3-methyl-naphthalen-1-yl] butanedioate X from 4-{[4-(acetyloxy)-2-[(2E,6E,10E,14E,18E,22E)-3,7,11,15,19,23,27-heptamethyloctacosa-2,6,10,14,18,22,26-heptaen-1-yl]-3-methylnaphthalen-1-yl]oxy}-4-oxobutanoic acid Xa (n=7)

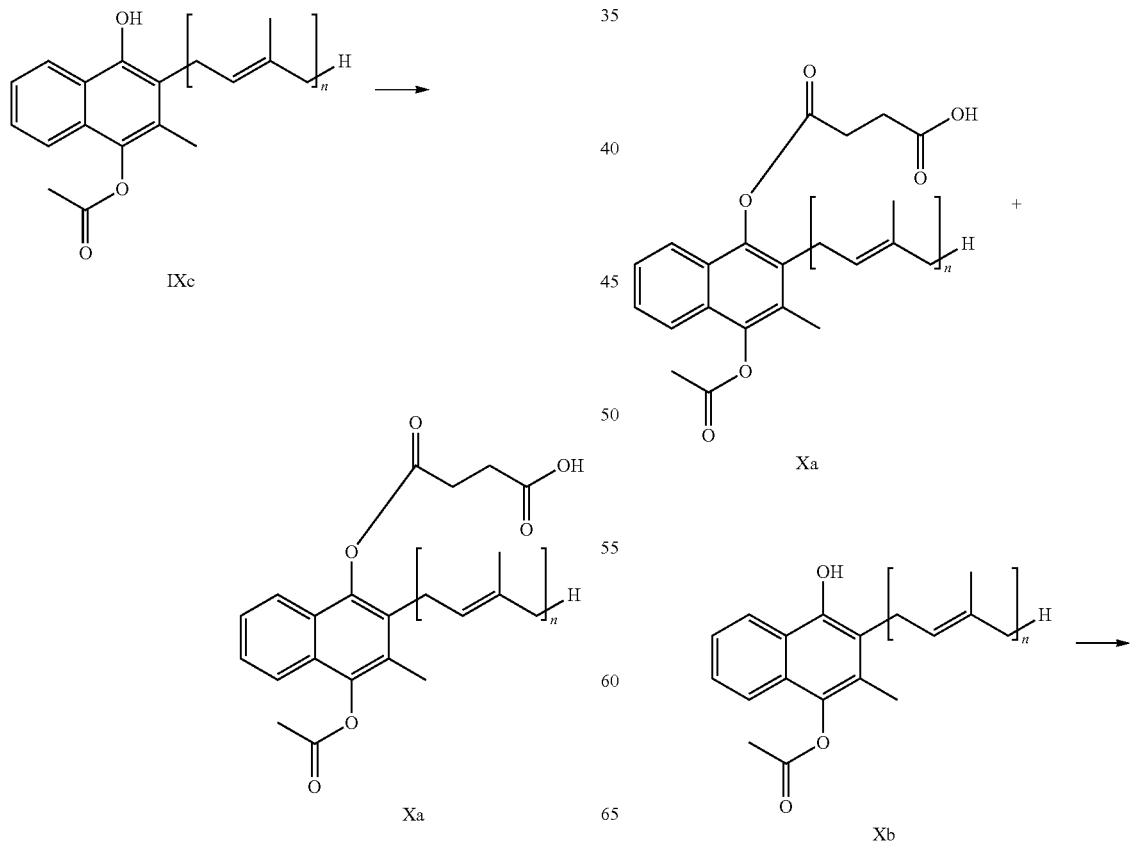

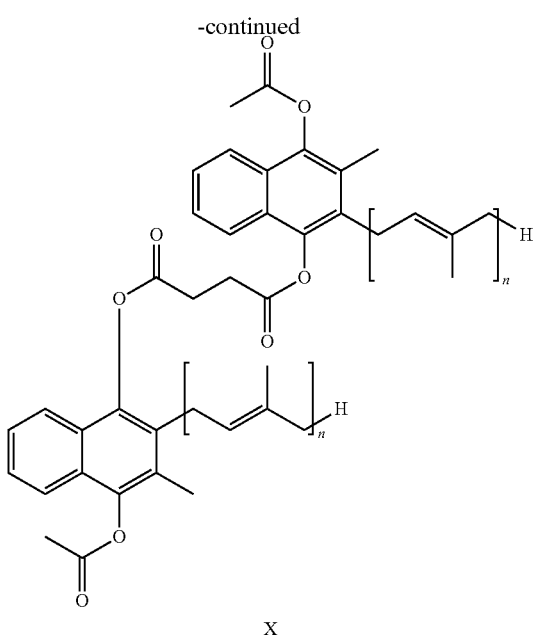

X

Figure 16:
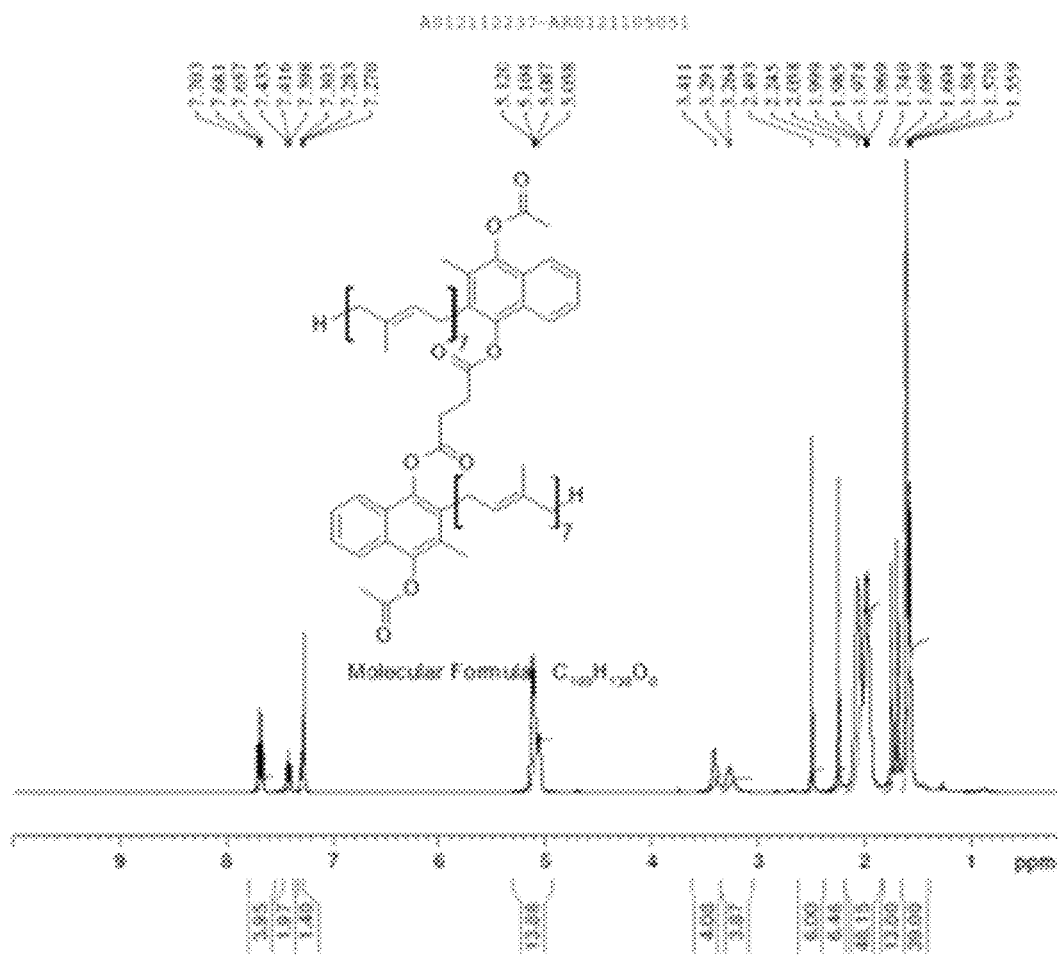
FIG. 16 shows that the crude product obtained was purified by column chromatography (10% ethyl acetate/hexane) to yield MK-7-succinate dimer X, n=7, as a waxy solid (0.44 g, 38%).

To a stirring solution of Xa, n=7, (0.62 g, 0.78 mmol) in DCM (6.2 mL, 10V) was added EDCI (0.176 g, 1.17 mmol) and DMAP (0.09 g, 0.78 mmol) at 0-5° C. and stirred for 10 min at same temperature. To the above reaction mixture Xb, n=7, (0.52 g, 0.78 mmol) in DCM (4.0 mL) was added at 0-5° C. and stirred for 1-2 at 25-30° C. Reaction completion was monitored by TLC (15% ethyl acetate/hexane). The reaction mixture was diluted with ethyl acetate (200 mL) and washed with water (2×100 mL). The organic layer was separated and washed with brine solution (50 mL) then dried over sodium sulfate and concentrated. Crude product obtained was purified by column chromatography (10% ethyl acetate/hexane) to yield MK-7-succinate dimer X, n=7, as a waxy solid (0.44 g, 38%), as shown in FIG. 16.

Preparation of MK-7 via α-Allylation and Retro-Diels-Alder Reaction

α-Allylation. To a 20 mL oven-dried scintillation vial was added freshly prepared heptaprenyl bromide (1.7 g, 3.05 mmol, 2.44 equiv) and a stir bar. The di-ketone (298 mg, 1.25 mmol, 1.00 equiv) was then added and allowed to disperse with gentle stirring. Sodium t-butoxide (300 mg, 3.13 mmol, 2.50 equiv) was removed from a glove box in a 1-dram vial and added in one addition to the stirring reaction mixture at RT resulting in a red reaction mixture. The vial was then sealed and stirred rapidly (900 RPM) at RT. After 1 h, the reaction was deemed complete by TLC. The entire reaction mixture was then taken up in $Et_2O$ and dried onto Celite. The crude reaction was then loaded onto a packed silica column (25 mm×152 mm) and filtered through the silica using two column volumes of hexanes, 1 column volume of 3.5% $Et_2O$/hexanes, and four column volumes of 7% $Et_2O$/hexanes, the latter of which was collected. The organics were then evaporated into a 20 mL scintillation vial resulting in 869 mg of the α-allylated product, as a golden yellow oil which was carried over directly to the retro-Diels-Alder reaction.

Retro-Diels-Alder Reaction: The vial containing the α-allylated product was then placed under high vacuum (<15 torr pressure) and heated in a 20 mL scintillation aluminum heating block to 85° C. internal temperature neat with no stirring. The reaction was allowed to heat until a constant mass was observed from loss of cyclopentadiene, as well as completion by TLC. The resulting golden oil was then purified by flash chromatography (4% $Et_2O$/hexanes) and dried under high vacuum resulting in a yellow solid (648 mg, 80% yield over two steps). $R_f$=0.60 (1:9 $Et_2O$/hexanes).

Administration of the Compounds in Subjects at Risk for Development of Calciphylaxis:

This example describes the administration of the compounds of the present application to subjects at risk for development of calciphylaxis, but who have not yet developed the characteristic skin lesions of calciphylaxis. Risk factors to be considered include, but are not limited to, diabetes mellitus, obesity, hemodialysis, and prior treatment with warfarin (Nigwekar et al. (2016) "A Nationally Representative Study of Calcific Uremic Arteriolopathy Risk Factors," J. Am. Soc. Nephrol. 27(11):3421-9). The administration of these compounds can result in protection of the

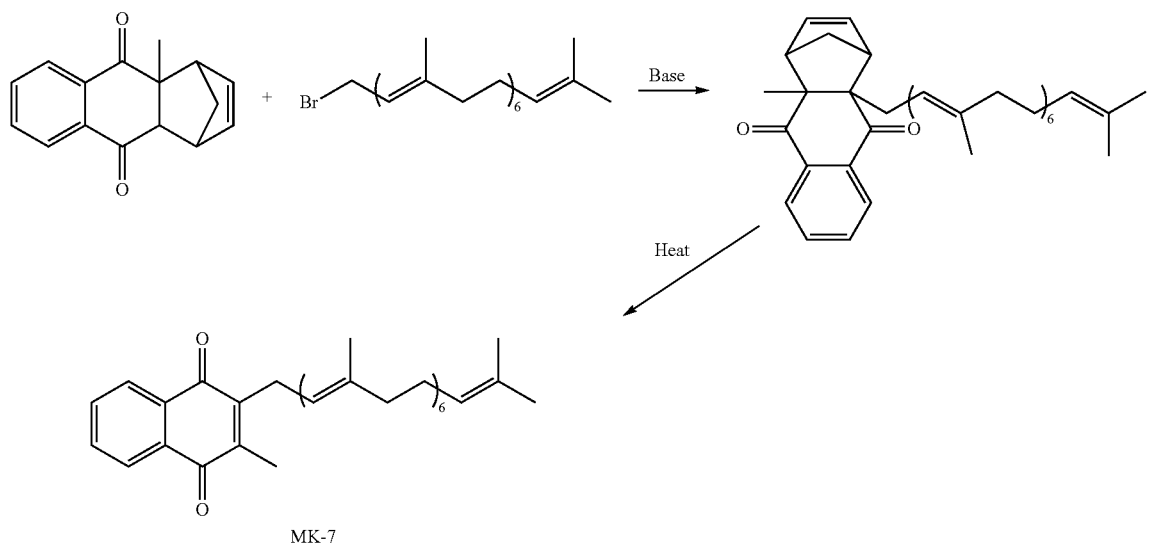

MK-7 subjects from skin lesions and a change in certain biomarker levels indicative of the prevention of the development of calciphylaxis.

Subjects at risk of development of calciphylaxis orally receive a selected compound of the present application at 5 mg, 10 mg, 20 mg, 30 mg, 50 mg or 100 mg once daily for at least 2 weeks, 4 weeks, 6 weeks, 8 weeks, 3 months, 6 months, 1 year, or indefinitely. The dosage form is a 5 mg, 10 mg, 20 mg, 50 mg or 100 mg soft-gel capsule. Two 50 mg capsules are be administered once daily to the 100 mg dosage cohort. It should be noted that not all subjects with elevated risk factors for calciphylaxis will develop the characteristic skin lesions of calciphylaxis. The intent of treating with the compound of the present application proactively (prior to a clinical diagnosis of calciphylaxis) is the prevention of lesion appearance. Thus, a drop in frequency of, or elimination of lesion appearances is contemplated to be a successful treatment.

Several biomarkers can be assessed to determine the efficacy of the compound to be administered at the three dose levels. Exemplary biomarkers include PIVKA-II; uncarboxylated and total Matrix Gla Protein (MGP); uncarboxylated, carboxylated and total osteocalcin protein; uncarboxylated, carboxylated and total Protein C, osteoprotegerin, Fetuin A and hs-CRP. Blood samples are obtained to measure the biomarkers according to the following schedule. Blood sampling can occur during treatment on a weekly or monthly basis. It is contemplated that administration of the disclosed compounds will result in (i) an increase in PIVKA-II, which is indicative of slowing the progression of, arresting, or reversing, calciphylaxis, (ii) a decrease in uncarboxylated MGP, uncarboxylated osteocalcin, and/or uncarboxylated Protein C, which is indicative of slowing the progression of, arresting, or reversing calciphylaxis. Further, pulse wave velocity (PWV) can be measured to assess arterial compliance. Improved vascular compliance will be indicative of slowing the progression of, arresting, or reversing calciphylaxis.

Administration of the Disclosed Compounds of the Application in Subjects Diagnosed with Calciphylaxis:

This example describes the administration of the disclosed compounds to subjects diagnosed with calciphylaxis. Typical symptoms include presentation of characteristic painful skin lesions (Nigwekar et al. (2015) Calciphylaxis: Risk Factors, Diagnosis, and Treatment. Am. J. Kidney Dis. 66:133-46). Definitive diagnosis of calciphylaxis is achieved via skin biopsy. Further conditions need to be considered for correct diagnosis.

Subjects diagnosed with calciphylaxis orally receive the disclosed compound at 5 mg, 10 mg, 25 mg, 50 mg or 100 mg once daily for at least 2 weeks, 4 weeks, 6 weeks, 8 weeks, 3 months, 6 months, 1 year, or indefinitely. The dosage form is a 5 mg, 10 mg, 25 mg, 50 mg or 100 mg soft-gel capsule. Two 50 mg capsules are administered once daily to the 100 mg dosage cohort.

The arrest of, or decreases in lesion size and frequency is contemplated to be an indication of successful treatment. The administration of the disclosed compounds according to the foregoing will result in the arrest of, or decrease in lesion size and frequency. Additionally, because calciphylaxis has a considerable mortality risk, increased overall survival time of diagnosed subjects will be an indication of treatment success. Furthermore, the administration of the disclosed compounds according to the foregoing will result in an increased overall survival time of diagnosed subjects.

Administration of the Disclosed Compounds in Subjects with End Stage Renal Disease (ESRD) to Reverse or Slow the Progression of Tissue Calcification:

This example describes the administration of the disclosed compounds to a subject with ESRD and on stable hemodialysis. The administration of the disclosed compounds will result in a change in aortic compliance (via plethysmography), vascular calcification and certain biomarker levels indicative of slowing the progression of, arresting, or reversing tissue calcification.

ESRD subjects on stable hemodialysis orally receive the disclosed compounds at 5 mg, 10 mg, 25 mg, 50 mg, 100 mg, 200 mg, 300, mg, 400 mg or 500 mg once daily for least 2 weeks, 4 weeks, 6 weeks, 8 weeks, 3 months, 6 months, 1 year, or indefinitely. The dosage form is a 5 mg, 10 mg, 25 mg, 50 mg, 75 mg or 100 mg soft-gel capsule. Two 50 mg capsules are administered once daily to the 100 mg dosage cohort.

A 50 y.o., 65 kg male patient diagnosed with the typical symptoms associated with moderate calciphylaxis is treated with 100 mg of the compound of the formula I wherein M is $Ca^{2+}$, Y is 2 and m is 7, for a period of 8 weeks. After the treatment period, the patient is admitted and evaluated. The patient is found to have a significant change in the examined biomarker levels suggesting about a 10% reduction in vascular calcification, and is also shown to have a 10% reduction in tissue calcification.

A 65 y.o., 45 kg female patient diagnosed with the typical symptoms associated with moderate calciphylaxis is treated with 20 mg of the compound of the formula I wherein M is $Ca^2$, Y is 2 and m is 7, for a period of 10 weeks. After the treatment period, the patient is admitted and evaluated. The patient is found to have a significant change in the examined biomarker levels suggesting about a 20% reduction in vascular calcification, and is also shown to have a 15% reduction in tissue calcification.

A 55 y.o., 70 kg male patient diagnosed with the typical symptoms associated with moderate calciphylaxis is treated with 50 mg of the compound of the formula I wherein M is $K^+$, Y is 1 and m is 7, for a period of 3 months. After the treatment period, the patient is admitted and evaluated. The patient is found to have a significant change in the examined biomarker levels suggesting about a 25% reduction in vascular calcification, and is also shown to have a 20% reduction in tissue calcification.

Coronary arterial calcium scores (CAC) are used to estimate the extent of calcification of thoracic arteries. A high CAC score is indicative of calcification, and treatment has the aim of arresting the long-term increase in CAC score, or reversing it, or slowing the rate of increase.

Aortic plethysmography also is used to measure arterial compliance, which decreases as calcification increases. Pulse wave velocity (PWV) also is measured to assess arterial compliance. The foregoing measures are useful in estimating the utility of treatments intended to prevent, slow the progression of, arrest or reverse vascular calcification. These measurements are used pre- and post-treatment with the disclosed compounds to assess treatment value.

Several biomarkers are assessed to determine the efficacy of the disclosed compounds at the three dose levels. Exemplary biomarkers include PIVKA-II; uncarboxylated and total Matrix Gla Protein (MGP); uncarboxylated, carboxylated and total osteocalcin protein; uncarboxylated, carboxylated and total Protein C, and hs-CRP. Blood samples are obtained to measure the biomarkers, most conveniently during patient visits for hemodialysis.

The administration of the disclosed compounds can result in (i) an increase in PIVKA-II, which is indicative of slowing the progression of, arresting or reversing tissue calcification, (ii) a decrease in uncarboxylated MGP, uncarboxylated osteocalcin, and/or uncarboxylated Protein C, which is indicative of slowing the progression of, arresting or reversing tissue calcification, and/or (iii) a decrease in hs-CRP, which is indicative of slowing the progression of, arresting or reversing tissue calcification and/or reduced inflammation. Following the daily administration of 5 mg, 10 mg, 25 mg, 50 mg, 75 mg, 100 mg, 150 mg, 200 mg, 300 mg, 400 mg or 500 mg or more, of the disclosed compounds and compositions, at least one of PIVKA-II, under-carboxylated Matrix Gla Protein (MGP), under-carboxylated osteocalcin protein, will show a change indicative of slowing the progression of, arresting or reversing tissue calcification.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

References: 1) Rachel M. Holden et al. Vitamins K and D Status in Stages 3-5 Chronic Kidney Disease; *Clin J Am Soc Nephrol* 5: 590-597, 2010. 2) Pilkey, R. M. M D et al. Subclinical Vitamin K Deficiency in Hemodialysis Patients Am J Kidney Dis 49:432-439, 2007. 3) Westhofen P et al. Human vitamin K 2,3-epoxide reductase complex subunit 1-like 1 (VKORC1L1) mediates vitamin K-dependent intracellular antioxidant function. J Biol Chem 2011; 286: 15085-94. 4) Caspers, M. et al., Two enzymes catalyze vitamin K 2,3-epoxide reductase activity in mouse: VKORC1 is highly expressed in exocrine tissues while VKORC1L1 is highly expressed in brain. Thrombosis Research 135:977-983, 2015. 5) Himmelfarb, J. et al., Plasma protein thiol oxidation and carbonyl formation in chronic renal failure. *Kidney International*, Vol. 58: 2571-2578 2000. 6) Price, P. A. et al., Discovery of a High Molecular Weight Complex of Calcium, Phosphate, Fetuin, and Matrix-Carboxyglutamic Acid Protein in the Serum of Etidronate-treated Rats. J Biol Chem. 277 (6): 3926-3934, 2002. 7) Pasch, A. et al. Nanoparticle-Based Test Measures Overall Propensity for Calcification in Serum J Am Soc Nephrol 23: 1744-1752, 2012. 8) Nigwekar, S. U. et al. Vitamin K-Dependent Carboxylation of Matrix Gla Protein Influences the Risk of Calciphylaxis. J Am Soc Nephrol 28: 1717-1722, 2017.

What is claimed is:

1. A biologically active menaquinol derivative of the formula:

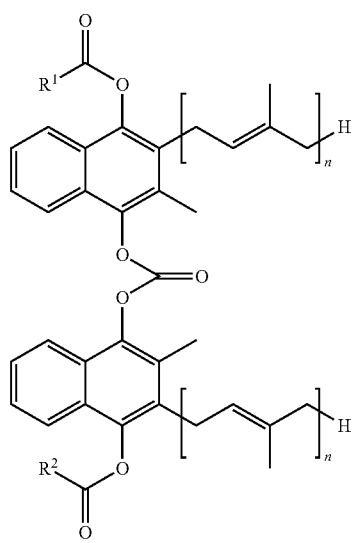

VIIIa.1

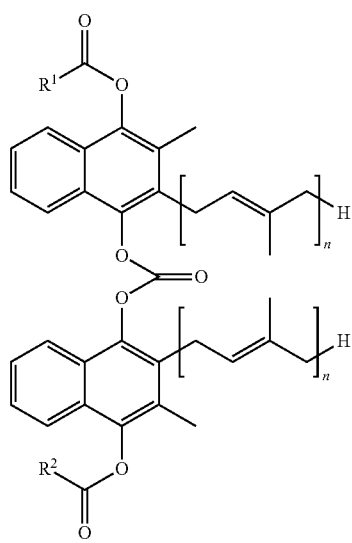

VIIIb.1

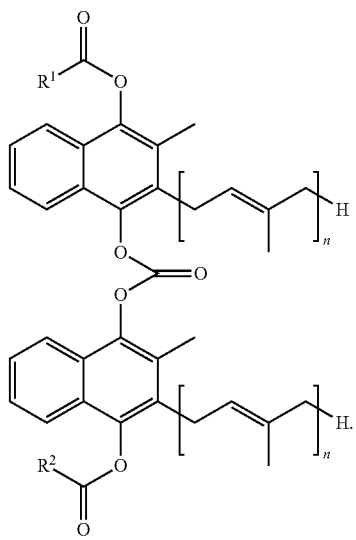
VIIIc.1
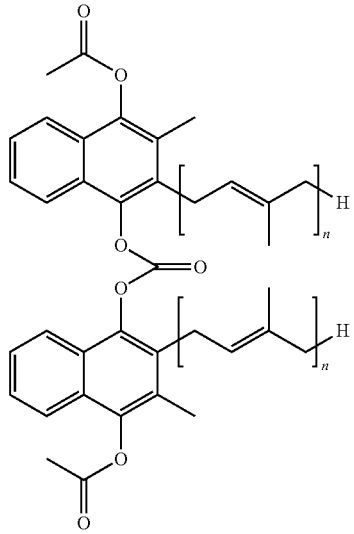
VIIIb
wherein:
each n is independently 7, 8 or 10; and
each $R^1$ and $R^2$ is independently $C_1$-$C_6$alkyl.
2. The menaquinol derivative of claim 1 selected from the group consisting of:
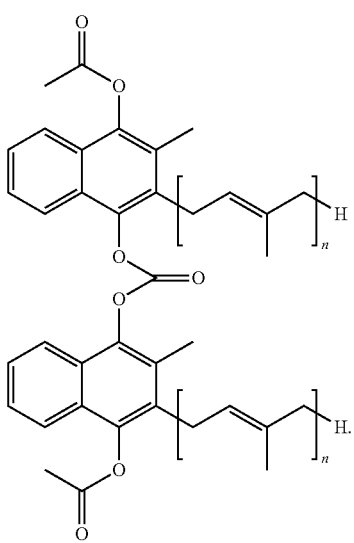
VIIIc 3. A biologically active menaquinol derivative of the formula:
XI.0
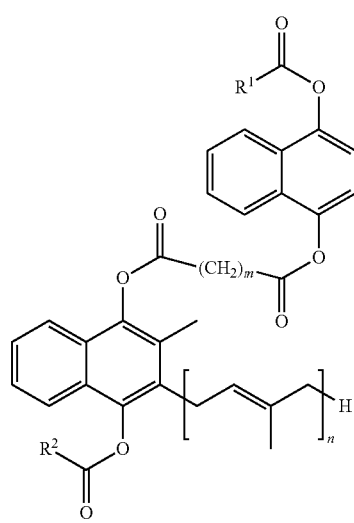
XI.1
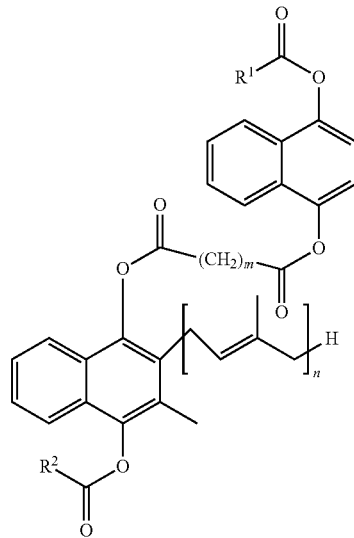
XI.2
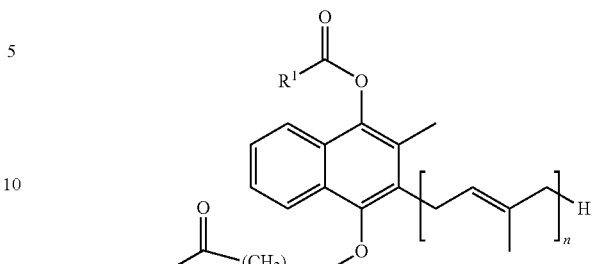
XI.3
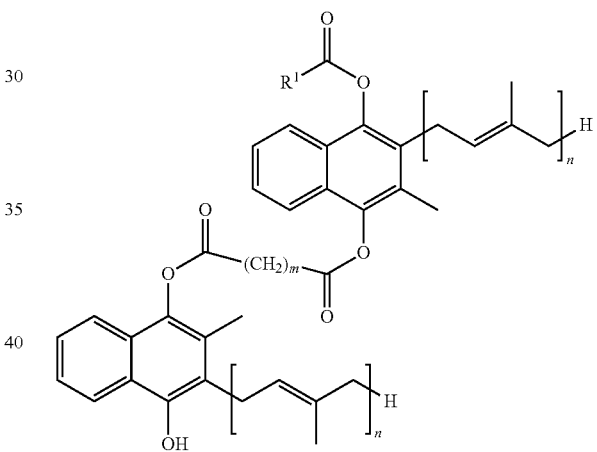
XI.4
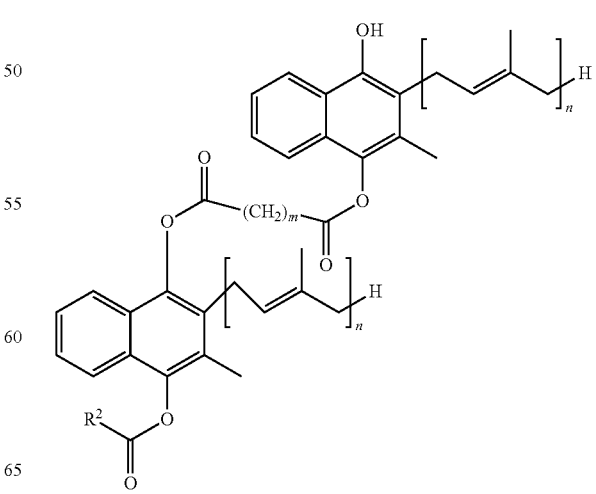

-continued
XI.5
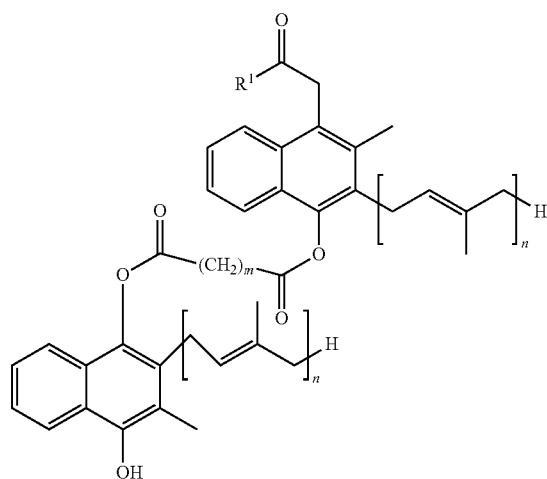
XI.6
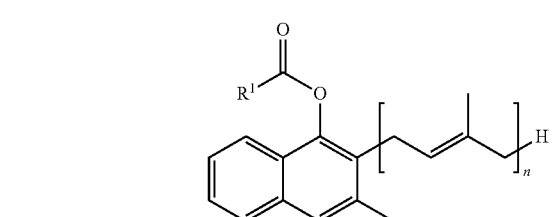
XI.7
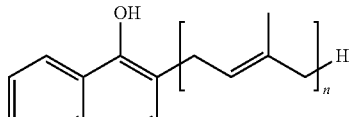
XI.8
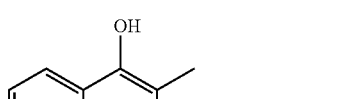
wherein:
m is 1, 2, 3, 4 or 5;
each n is independently 7, 8 or 10; and
each $R^1$ and $R^2$ is independently $C_1$-$C_6$alkyl.

4. The menaquinol derivative of claim 3 selected from the group consisting of:

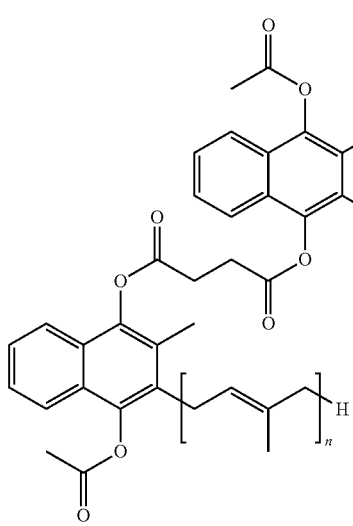

IX

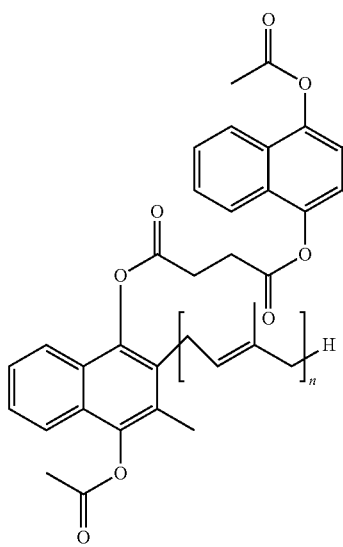

IX.01

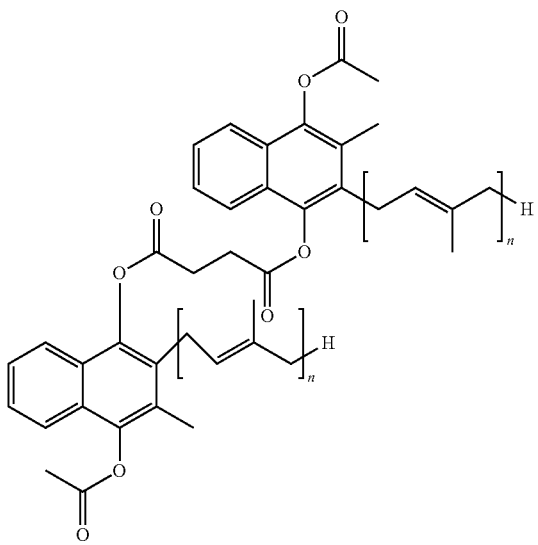

IX.0a wherein each n is independently 7, 8 or 10.

5. A pharmaceutical composition comprising a therapeutically effective amount of a menaquinol derivative of claim 1, or a mixture thereof; and a pharmaceutically acceptable excipient, wherein the composition is effective for the treatment of a condition associated with vitamin K selected from the treatment of osteoporosis, arteriosclerosis, calciphylaxis or tissue calcification.

6. A method for increasing the tissue concentration of menaquinol as a co-factor for gamma glutamate carboxylase (GGCX) for catalyzing the carboxylation of vitamin K dependent proteins that is associated with the treatment or prevention of osteoporosis, arteriosclerosis, calciphylaxis or tissue calcification in a patient in need thereof, the method comprising an administration of a therapeutically effective amount of a menaquinol derivative of claim 1 or a pharmaceutical composition comprising an effective amount of a menaquinol derivative of claim 1, or a mixture thereof, to said patient.

* * * * *